US011851474B2

(12) United States Patent
Maas et al.

(10) Patent No.: US 11,851,474 B2
(45) Date of Patent: Dec. 26, 2023

(54) MODIFIED SERPINS FOR THE TREATMENT OF BRADYKININ-MEDIATED DISEASE

(71) Applicant: Preclinics Gesellschaft für präklinische Forschung mbH, Potsdam (DE)

(72) Inventors: Coen Maas, Utrecht (NL); Steven de Maat, Utrecht (NL)

(73) Assignee: PRECLINICS GESELLSCHAFT FÜR PRÄKLINISCHE FORSCHUNG MBH, Potsdam (DE)

( * ) Notice: Subject to any disclaimer, the term of this patent is extended or adjusted under 35 U.S.C. 154(b) by 546 days.

(21) Appl. No.: 16/487,858

(22) PCT Filed: Feb. 23, 2018

(86) PCT No.: PCT/EP2018/054490
§ 371 (c)(1),
(2) Date: Aug. 22, 2019

(87) PCT Pub. No.: WO2018/054044
PCT Pub. Date: Aug. 30, 2018

(65) Prior Publication Data
US 2020/0010533 A1     Jan. 9, 2020

(30) Foreign Application Priority Data
Feb. 23, 2017   (EP) ..................... 17157527

(51) Int. Cl.
C07K 14/81     (2006.01)
A61K 38/00     (2006.01)
A61K 48/00     (2006.01)

(52) U.S. Cl.
CPC .......... C07K 14/8125 (2013.01); A61K 38/00 (2013.01); A61K 48/00 (2013.01)

(58) Field of Classification Search
CPC ..... C07K 14/8125; A61K 38/00; A61K 48/00
See application file for complete search history.

(56) References Cited

U.S. PATENT DOCUMENTS

2007/0259809 A1* 11/2007 Bock ....................... A61K 38/57
                                                           435/7.8
2011/0288005 A1* 11/2011 Silverman .......... C07K 14/7155
                                                           530/380
2016/0311887 A1* 10/2016 Huntington ............. A61P 43/00

FOREIGN PATENT DOCUMENTS

| EP | 2238984 A1 | 10/2010 |
| WO | WO01/35965 A1 | 5/2001 |
| WO | WO2006/090282 A2 | 8/2006 |
| WO | WO2015/086854 A1 | 6/2015 |

OTHER PUBLICATIONS

Felber, FEBS Journal, vol. 273, No. 11, Jun. 1, 2006. (Year: 2006).*
Felber, FEBS Journal, vol. 273, No. 11, Jun. 1, 2006 (Jun. 1, 2006), pp. 2505-2514 (cited on IDS filed Aug. 22, 2019) (Year: 2006).*
Felber et al., 2006, Mutant recombinant serpins as highly specific inhibitors of human kallikrein 14, FEBS Journal, 273: 2505-2514.*
Filion et al., 2004, Full or Partial Substitution of the Reactive Center Loop of alpha-1-Proteinase Inhibitor by that of Heparin Cofactor II: P1 Arg is Required for Maximal Thrombin Inhibition, Biochemistry, 43: 14864-14872.*
Kurachi et al., 1981, Cloning and sequence of cDNA coding for alpha1-antitrypsin, PNAS, 78(11): 6826-6830.*
Felber Loyse M et al.: Mutant recombinant serpins as highly specific inhibitors of human kallikrein 14, Fees Journal, Wiley-Blackwell Publishing Ltd, vol. 273, No. 11, Jun. 1, 2006 (Jun. 1, 2006), pp. 2505-2514, Table 1 ,3 and Discussion.
Caliezi et al: "CI-Esterase inhibitor: an anti-inflammatory agent and its potential use in the treatment of disease other than hereditary angioedema", Pharmacological Reviews, American Society for Pharmacology and Experimental Therapeutics, US, vol. 52, No. 1, Jan. 1, 2000 (Jan. 1, 2000), pp. 91-112, the whole document.
Ruby Law et al "An overview of the serpin superfamily". Genome biology, Jan. 1, 2006 (Jan. 1, 2006), pp. 216-216.
Ostergaard Henrik et al: "Inhibitory serpins from wheat grain with reactive centers resembling glutamine-rich repeats of prolamin storage proteins. Cloning and characterization of five major molecular forms", Journal of Biological Chemistry, American Society for Biochemistry and Molecular Biology, vol. 275, No. 43, Oct. 27, 2000 pp. 33272-33279.

(Continued)

*Primary Examiner* — Amber D Steele
(74) *Attorney, Agent, or Firm* — Knobbe Martens Olson & Bear LLP

(57) ABSTRACT

The present invention relates to modified serpins for use in the treatment of bradykinin-mediated diseases. The modified serine protease inhibitors (serpins) have mutations in one or more of the P4, P3, P2, P1 and P1' residues of their reactive center loop, which mutations increase the serpin's inhibition of plasma kallikrein (PK) as compared to the corresponding unmodified serpin. The mutations in the modified serpins of the invention further ensure that serpins display substantially no inhibition of at least thrombin and activated protein C. A modified serpin of the invention further preferably shows increased inhibition of at least one of an active form of Factor XII (FXII) and plasmin as compared to the corresponding unmodified serpin, and, preferably, the serpin inhibits at least one of an active form of FXII and PK stronger than they are inhibited by C1 esterase inhibitor. Preferably the modified serpin is a modified α1-antitrypsin. The invention further pertains to nucleic acid molecule encoding the modified serpins of the invention, e.g. a gene therapy vector, and to pharmaceutical compositions comprising the modified serpins of the invention or such gene therapy vectors.

17 Claims, 7 Drawing Sheets

Specification includes a Sequence Listing.

(56) References Cited

OTHER PUBLICATIONS

De Maat, et al. "Plasmin is a natural trigger for bradykinin production in patients with hereditary angioedema with factor XII mutations." Journal of Allergy and Clinical Immunology 138.5 (2016): 1414-1423.

Oschatz, et al. "Mast cells increase vascular permeability by heparin-initiated bradykinin formation in vivo." Immunity 34.2 (2011): 258-268.

Sala-Cunnill et al. "Plasma contact system activation drives anaphylaxis in severe mast cell-mediated allergic reactions." Journal of Allergy and Clinical Immunology 135.4 (2015): 1031-1043.

Scott, et al. "Alpha-1-antitrypsin-Pittsburgh. A potent inhibitor of human plasma factor XIa, kallikrein, and factor XIIf." The Journal of clinical investigation 77.2 (1986): 631-634.

Heeb, et al. "Inhibition of activated protein C by recombinant alpha 1-antitrypsin variants with substitution of arginine or leucine for methionine358." Journal of Biological Chemistry 265.4 (1990): 2365-2369.

Cicardi, M., et al. "Novelties in the diagnosis and treatment of angioedema." J Investig Allergol Clin Immunol 26.4 (2016): 212-221.

Van Doorn, Martijn BA, et al. "A phase I study of recombinant human C1 inhibitor in asymptomatic patients with hereditary angioedema." Journal of allergy and clinical immunology 116.4 (2005): 876-883.

Archibald, Alan L., et al. "High-level expression of biologically active human alpha 1-antitrypsin in the milk of transgenic mice." Proceedings of the National Academy of Sciences 87.13 (1990): 5178-5182.

Cugno, M., A. Tedeschi, and J. Nussberger. "Bradykinin in idiopathic non-histaminergic angioedema." Clinical & Experimental Allergy 47.1 (2017): 139-140.

\* cited by examiner

MODIFIED SERPINS FOR THE TREATMENT OF BRADYKININ-MEDIATED DISEASE

The present application is being filed along with a Sequence Listing in electronic format. The Sequence Listing is provided as a file entitled 56296762_1.TXT, created and last modified on Sep. 15, 2022, which is 91.3 Kb in size. The information in the electronic format of the Sequence Listing is incorporated herein by reference in its entirety.

FIELD OF THE INVENTION

The present invention relates to the field of medicine and pharmacy, in particular to the field of biopharmaceuticals for use in the treatment of bradykinin-mediated disease. More specifically, the invention relates to serine protease inhibitors (serpin) molecules modified to have increased specificity for bradykinin-generating proteases of the plasma contact system, particularly plasma kallikrein (PK) and active forms of factor XII (FXII) and/or plasmin.

BACKGROUND ART

α1-antitrypsin (α1AT) is a naturally occurring serine protease inhibitor (serpin) in human blood. Its natural function is to inhibit amongst others the inflammatory enzyme leucocyte elastase. To execute this function, it acts as a molecular mouse-trap: the serpin contains a loop with a specific amino acid sequence that is recognized and cleaved by elastase. This generates a stable (SDS and reduction resistant) complex between α1AT and elastase that renders the latter inactive. This inactivation mechanism is a common feature of serpins and the specific amino acid sequence of a serpin's reactive center loop (RCL) determines which serine protease enzyme recognizes the specific serpin and is inhibited by it.

In hereditary angioedema (HAE), overproduction of the inflammatory peptide bradykinin causes painful and dangerous attacks of tissue swelling. Bradykinin is produced by enzymes of the plasma contact system (FXIIa, PK). These enzymes are controlled by the serpin C1-esterase inhibitor (C1INH). Hence, in HAE, congenital deficiency in C1INH leads to uncontrolled bradykinin production. In a similar manner, neutralizing antibodies against C1INH cause acquired angioedema.

We recently identified plasmin as an new player in the bradykinin forming cascade (de Maat et al. J Allergy Clin Immunol. 2016 Apr. 6. pii: 80091-6749(16)30006-9). In addition, the pathological consequences of excessive bradykinin production extend beyond angioedema: in severe allergic reactions, bradykinin is a critical disease mediator (Oschatz et al. Immunity. 2011 Feb. 25; 34(2):258-68; Sala-Cunill et al. J Allergy Clin Immunol. 2015 April; 135(4):1031-43).

It has been previously described that the α1AT Pittsburgh variant has a single point mutation (M358R, numbering based upon mature protein sequence of natural occurring α1AT) that significantly alters its specificity (Scott et al. J Clin Invest. 1986 February; 77(2):631-4). From an inhibitor of elastase and trypsin, it has now become a strong inhibitor of the contact system enzymes but also of activated protein C (APC) (Heeb et al 1990 J Biol Chem February 5; 265(4):2365-9) and thrombin, the latter causing bleeding in patients carrying this variant.

WO2006/090282 discloses variants of α1AT that are modified for increased substrate specificity towards the human tissue kallikrein 14 (hK14) protease, a kallikrein the expression of which is correlated with poor prognosis for breast and prostate cancers.

For HAE, protein re-supplementation therapy (plasma purified or recombinant C1INH) is the golden standard (Cicardi et al. J. Invest. Allergol Clin Immunol 2016 January; 1; 26 (4):212-22). This therapy is not ideal because of the relatively short circulating half-life of C1INH (Caliezi et al Pharmacol Rev 2000 March; 52(1):91-112). For example, plasma derived C1INH has a half-life time of 32.7 hours (Bernstein et al Ann Allergy Asthma Immunol. 2010 August; 105(2):149-54) and the only recombinant C1INH currently available, Ruconest®, has a half-life of only three hours (van Doorn et al J Allergy Clin Immunol 2005 October; 116(4): 876-83) whereas for example α1AT has a half-life of 4-5 days (Archibald et al Proc. Natl, Acad Sci 1990 87; 5178-5182). Furthermore, on a molecular basis, C1 INH is a kinetically unfavorable serpin. It has weak inhibitory properties towards contact system enzymes (Scott et al J Clin Invest 1986 February; 77(2):631-4).

This becomes clear in the clinic: the large majority patients (>95%) that suffer from angioedema are without C1 INH deficiency (idiopathic angioedema). There is no therapy for these patients, but bradykinin is strongly implicated as disease mediator (Cugno et al 2017 Clin Exp Allergy. 2017 January; 47(1):139-140). In these patients, C1INH is not able to maintain in control of the contact system.

It is an object of the present invention to provide for novel modified serpins that are useful in the treatment of bradykinin-mediated diseases and that address the shortcomings of C1INH.

SUMMARY OF THE INVENTION

In a first aspect the invention relates to a modified serpin that has mutations in one or more of the P4, P3, P2, P1, and P1' residues of its reactive center loop (RCL), which mutations increase the inhibition of plasma kallikrein (PK) as compared to the corresponding unmodified serine protease inhibitors (serpin). Preferably the modified serpin more strongly inhibits PK than the serpin inhibits thrombin, and also preferably, the modified serpin more strongly inhibits PK than the serpin inhibits activated protein C (APC). The modified serpin preferably is for use in the treatment of a bradykinin-mediated disease.

Preferably in a modified serpin of the invention, the mutations increase the inhibition of at least one of an active form of Factor XII and plasmin as compared to the corresponding unmodified serpin, and wherein, preferably, the serpin inhibits at least one of an active form of FXII and PK as strong or stronger than they are inhibited by 01 esterase inhibitor. A modified serpin of the invention is preferably characterized in that the minimal amount of the serpin that inhibits PK activity by at least 50%, is an amount that inhibits thrombin activity by no more than 15%. More preferably, the minimal amount of the serpin that inhibits PK activity by at least 50%, is an amount that inhibits at least one of: a) plasmin by at least 15%; b) an active form of FXII by at least 15%; and, c) APC by no more than 15%.

A modified serpin of the invention, preferably is a serpin comprising an RCL wherein the P1 residue is lysine (K) or arginine (R), the P2 residue is not proline (P) and wherein the P4 residue is serine (S). More preferably, the serpin comprises an RCL wherein the residues P4-P1 of the RCL have an amino acid sequence selected from the group consisting of SMTR (SEQ ID NO: 12), SGQR (SEQ ID NO:

13), SVTR (SEQ ID NO: 14), SATR (SEQ ID NO: 15), SFNR (SEQ ID NO: 16), SWKK (SEQ ID NO: 17), SEAR (SEQ ID NO: 18), SVVK (SEQ ID NO: 19), SDYK (SEQ ID NO: 20), SVRK (SEQ ID NO: 21), SPRR (SEQ ID NO: 22), SMDR (SEQ ID NO: 23), SLGR (SEQ ID NO: 24), SKGR (SEQ ID NO: 25), SGNR (SEQ ID NO: 26), SMHR (SEQ ID NO: 27) and SLLR (SEQ ID NO: 28). A modified serpin of the invention further preferably has a mutation whereby the P1' residue of its reactive center loop (RCL) is selected from the group consisting of: Q, F, H, R, K, C, L, Y, N, I, D, W, E, V, M, A, T and P, of which K, L, Y, I, D, E, A, T, M, R and V are preferred, and I and V are most preferred. A particularly preferred modified serpin of the invention is a serpin wherein the residues P4-P1 of the RCL have the amino acid sequence SLLR (SEQ ID NO: 28) and wherein the P1' residue is selected from the group consisting of: Q, F, H, R, K, C, L, Y, N, I, D, W, E, V, M, A, T and P, of which K, L, Y, I, D, E, A, T, M, R and V are preferred, and I and V are most preferred.

A modified serpin according to the invention preferably is a serpin comprising an amino acid sequence that has at least 70% sequence identity to the sequence of a wild-type serpin and wherein preferably, the wild type serpin is selected from the group consisting of α1-antitrypsin (α1AT) (SERPINA1), α1-antichymotrypsin (SERPINA3), C1-esterase inhibitor (SERPING1), α2-antiplasmin (SERPINF2), antithrombin (ATIII) (SERPINC1), heparin cofactor II (HCII) (SERPIND1), protein C inhibitor (PCI) (SERPINA5), Kallistatin (SERPINA4), Plasminogen activator inhibitor (SERPINE1), Protease nexin 1 (SERPINE2) and Protein Z-dependent protease inhibitor (SERPINA10), of which α1AT is most preferred. A modified serpin of the invention, further preferably is a serpin that has been modified to reduce the susceptibility to oxidation.

In a second aspect, the invention relates to a modified serpin of the invention for use in the treatment of a bradykinin-mediated disease. Preferably, the serpin is for use in the treatment of a bradykinin-mediated disease selected from the group consisting of hereditary angioedema, idiopathic angioedema, rheumatoid arthritis, Crohn's disease, ulcerative colitis, lupus, Alzheimer's disease, septic shock, burn injury, brain ischemia/reperfusion injury, cerebral edema, diabetic retinopathy, diabetic nephropathy, macular edema, vasculitis, arterial or venous thrombosis, thrombosis associated with ventricular assist devices or stents, heparin-induced thrombocytopenia with thrombosis, thromboembolic disease, and coronary heart disease with unstable angina pectoris, edema, eye disease, gout, intestinal bowel disease, oral mucositis, neuropathic pain, inflammatory pain, spinal stenosis-degenerative spine disease, post-operative ileus, aortic aneurysm, osteoarthritis, hereditary angioedema, pulmonary embolism, stroke, head trauma or peri-tumor brain edema, sepsis, acute middle cerebral artery (MCA) ischemic event (stroke), restenosis (e.g., after angioplasty), systemic lupus erythematosis nephritis, an autoimmune disease, an inflammatory disease for example (chronic) auto-inflammatory urticaria, a cardiovascular disease, a neurological disease, a disease associated with protein misfolding, a disease associated with angiogenesis, hypertensive nephropathy and diabetic nephropathy, allergic and respiratory diseases (e.g. anaphylaxis, asthma, chronic obstructive pulmonary disease, acute respiratory distress syndrome, cystic fibrosis, persistent, rhinitis) and tissue injuries (e.g. burn or chemical injury).

In a third aspect, the invention relates to a gene therapy vector comprising a nucleotide sequence encoding a modified serpin according to the invention. Preferably the gene therapy vector is for use in the treatment of a bradykinin-mediated disease, wherein, preferably, the bradykinin-mediated disease is selected from the group consisting of hereditary angioedema, idiopathic angioedema, rheumatoid arthritis, Crohn's disease, ulcerative colitis, lupus, Alzheimer's disease, septic shock, burn injury, brain ischemia/reperfusion injury, cerebral edema, diabetic retinopathy, diabetic nephropathy, macular edema, vasculitis, arterial or venous thrombosis, thrombosis associated with ventricular assist devices or stents, heparin-induced thrombocytopenia with thrombosis, thromboembolic disease, and coronary heart disease with unstable angina pectoris, edema, eye disease, gout, intestinal bowel disease, oral mucositis, neuropathic pain, inflammatory pain, spinal stenosis-degenerative spine disease, post-operative ileus, aortic aneurysm, osteoarthritis, hereditary angioedema, pulmonary embolism, stroke, head trauma or peri-tumor brain edema, sepsis, acute middle cerebral artery (MCA) ischemic event (stroke), restenosis (e.g., after angioplasty), systemic lupus erythematosis nephritis, an autoimmune disease, an inflammatory disease for example (chronic) auto-inflammatory urticaria, a cardiovascular disease, a neurological disease, a disease associated with protein misfolding, a disease associated with angiogenesis, hypertensive nephropathy and diabetic nephropathy, allergic and respiratory diseases (e.g. anaphylaxis, asthma, chronic obstructive pulmonary disease, acute respiratory distress syndrome, cystic fibrosis, persistent, rhinitis) and tissue injuries (e.g. burn or chemical injury).

In a fourth aspect, the invention pertains to a nucleic acid molecule comprising a nucleotide sequence encoding a modified serpin according to invention.

In a fifth aspect, the invention relates to a vector comprising a nucleotide sequence encoding a modified serpin according to invention. Preferably, the vector is a gene therapy vector.

In a sixth aspect, the invention pertains to a host cell comprising the vector of the invention, which host cell preferably expresses a modified serpin of the invention encoded by a nucleotide sequence in the vector.

In a seventh aspect, the invention relates to a pharmaceutical composition. The pharmaceutical composition comprises a pharmaceutically acceptable excipient and a modified serpin of the invention, a nucleic acid molecule of the invention, gene therapy vector of the invention or a host cell of the invention comprising the nucleic acid molecule.

DESCRIPTION OF THE INVENTION

Definitions

The terms "homology", "sequence identity" and the like are used interchangeably herein. Sequence identity is herein defined as a relationship between two or more amino acid (polypeptide or protein) sequences or two or more nucleic acid (polynucleotide) sequences, as determined by comparing the sequences. In the art, "identity" also means the degree of sequence relatedness between amino acid or nucleic acid sequences, as the case may be, as determined by the match between strings of such sequences. "Similarity" between two amino acid sequences is determined by comparing the amino acid sequence and its conserved amino acid substitutes of one polypeptide to the sequence of a second polypeptide. "Identity" and "similarity" can be readily calculated by known methods.

"Sequence identity" and "sequence similarity" can be determined by alignment of two peptide or two nucleotide sequences using global or local alignment algorithms, depending on the length of the two sequences. Sequences of similar lengths are preferably aligned using a global alignment algorithms (e.g. Needleman Wunsch) which aligns the sequences optimally over the entire length, while sequences of substantially different lengths are preferably aligned using a local alignment algorithm (e.g. Smith Waterman). Sequences may then be referred to as "substantially identical" or "essentially similar" when they (when optimally aligned by for example the programs GAP or BESTFIT using default parameters) share at least a certain minimal percentage of sequence identity (as defined below). GAP uses the Needleman and Wunsch global alignment algorithm to align two sequences over their entire length (full length), maximizing the number of matches and minimizing the number of gaps. A global alignment is suitably used to determine sequence identity when the two sequences have similar lengths. Generally, the GAP default parameters are used, with a gap creation penalty=50 (nucleotides)/8 (proteins) and gap extension penalty=3 (nucleotides)/2 (proteins). For nucleotides the default scoring matrix used is nwsgapdna and for proteins the default scoring matrix is Blosum62 (Henikoff & Henikoff, 1992, PNAS 89, 915-919). Sequence alignments and scores for percentage sequence identity may be determined using computer programs, such as the GCG Wisconsin Package, Version 10.3, available from Accelrys Inc., 9685 Scranton Road, San Diego, CA 92121-3752 USA, or using open source software, such as the program "needle" (using the global Needleman Wunsch algorithm) or "water" (using the local Smith Waterman algorithm) in EmbossWIN version 2.10.0, using the same parameters as for GAP above, or using the default settings (both for 'needle' and for 'water' and both for protein and for DNA alignments, the default Gap opening penalty is 10.0 and the default gap extension penalty is 0.5; default scoring matrices are Blossum62 for proteins and DNAFull for DNA). When sequences have a substantially different overall lengths, local alignments, such as those using the Smith Waterman algorithm, are preferred.

Alternatively percentage similarity or identity may be determined by searching against public databases, using algorithms such as FASTA, BLAST, etc. Thus, the nucleic acid and protein sequences of the present invention can further be used as a "query sequence" to perform a search against public databases to, for example, identify other family members or related sequences. Such searches can be performed using the BLASTn and BLASTx programs (version 2.0) of Altschul, et al. (1990) J. Mol. Biol. 215:403-10. BLAST nucleotide searches can be performed with the NBLAST program, score=100, wordlength=12 to obtain nucleotide sequences homologous to oxidoreductase nucleic acid molecules of the invention. BLAST protein searches can be performed with the BLASTx program, score=50, wordlength=3 to obtain amino acid sequences homologous to protein molecules of the invention. To obtain gapped alignments for comparison purposes, Gapped BLAST can be utilized as described in Altschul et al., (1997) Nucleic Acids Res. 25(17): 3389-3402. When utilizing BLAST and Gapped BLAST programs, the default parameters of the respective programs (e.g., BLASTx and BLASTn) can be used. See the homepage of the National Center for Biotechnology Information on the World-Wide Web at ncbi.nlm.hih.gov.

Optionally, in determining the degree of amino acid similarity, the skilled person may also take into account so-called "conservative" amino acid substitutions, as will be clear to the skilled person. Conservative amino acid substitutions refer to the interchangeability of residues having similar side chains. Examples of classes of amino acid residues for conservative substitutions are given in the Tables below.

| | |
|---|---|
| Acidic Residues | Asp (D) and Glu (E) |
| Basic Residues | Lys (K), Arg (R), and His (H) |
| Hydrophilic Uncharged Residues | Ser (S), Thr (T), Asn (N), and Gln (Q) |
| Aliphatic Uncharged Residues | Gly (G), Ala (A), Val (V), Leu (L), and Ile (I) |
| Non-polar Uncharged Residues | Cys (C), Met (M), and Pro (P) |
| Aromatic Residues | Phe (F), Tyr (Y), and Trp (W) |

Alternative conservative amino acid residue substitution classes.

| | | | |
|---|---|---|---|
| 1 | A | S | T |
| 2 | D | E | |
| 3 | N | Q | |
| 4 | R | K | |
| 5 | I | L | M |
| 6 | F | Y | W |

Alternative Physical and Functional Classifications of Amino Acid Residues.

| | |
|---|---|
| Alcohol group-containing residues | S and T |
| Aliphatic residues | I, L, V, and M |
| Cycloalkenyl-associated residues | F, H, W, and Y |
| Hydrophobic residues | A, C, F, G, H, I, L, M, R, T, V, W, and Y |
| Negatively charged residues | D and E |
| Polar residues | C, D, E, H, K, N, Q, R, S, and T |
| Positively charged residues | H, K, and R |
| Small residues | A, C, D, G, N, P, S, T, and V |
| Very small residues | A, G, and S |
| Residues involved in turn formation | A, C, D, E, G, H, K, N, Q, R, S, P and T |
| Flexible residues | Q, T, K, S, G, P, D, E, and R |

Nucleotide sequences encoding modified serpins of the invention may also be defined by their capability to hybridize with the nucleotide sequences of encoding modified serpins as exemplified herein, under moderate, or preferably under stringent hybridization conditions. Stringent hybridization conditions are herein defined as conditions that allow a nucleic acid sequence of at least about 25, preferably about 50 nucleotides, 75 or 100 and most preferably of about 200 or more nucleotides, to hybridise at a temperature of about 65° C. in a solution comprising about 1 M salt, preferably 6×SSC or any other solution having a comparable ionic strength, and washing at 65° C. in a solution comprising about 0.1 M salt, or less, preferably 0.2×SSC or any other solution having a comparable ionic strength. Preferably, the hybridization is performed overnight, i.e. at least for 10 hours and preferably washing is performed for at least one hour with at least two changes of the washing solution. These conditions will usually allow the specific hybridization of sequences having about 90% or more sequence identity.

Moderate conditions are herein defined as conditions that allow a nucleic acid sequences of at least 50 nucleotides, preferably of about 200 or more nucleotides, to hybridise at a temperature of about 45° C. in a solution comprising about 1 M salt, preferably 6×SSC or any other solution having a comparable ionic strength, and washing at room temperature in a solution comprising about 1 M salt, preferably 6×SSC or any other solution having a comparable ionic strength.

Preferably, the hybridization is performed overnight, i.e. at least for 10 hours, and preferably washing is performed for at least one hour with at least two changes of the washing solution. These conditions will usually allow the specific hybridization of sequences having up to 50% sequence identity. The person skilled in the art will be able to modify these hybridization conditions in order to specifically identify sequences varying in identity between 50% and 90%.

A "nucleic acid construct" or "nucleic acid vector" is herein understood to mean a man-made nucleic acid molecule resulting from the use of recombinant DNA technology. The term "nucleic acid construct" therefore does not include naturally occurring nucleic acid molecules although a nucleic acid construct may comprise (parts of) naturally occurring nucleic acid molecules. The terms "expression vector" or expression construct" refer to nucleotide sequences that are capable of affecting expression of a gene in host cells or host organisms compatible with such sequences. These expression vectors typically include at least suitable transcription regulatory sequences and optionally, 3' transcription termination signals. Additional factors necessary or helpful in effecting expression may also be present, such as expression enhancer elements. The expression vector will be introduced into a suitable host cell and be able to effect expression of the coding sequence in an in vitro cell culture of the host cell. The expression vector will be suitable for replication in the host cell or organism of the invention.

As used herein, the term "promoter" or "transcription regulatory sequence" refers to a nucleic acid fragment that functions to control the transcription of one or more coding sequences, and is located upstream with respect to the direction of transcription of the transcription initiation site of the coding sequence, and is structurally identified by the presence of a binding site for DNA-dependent RNA polymerase, transcription initiation sites and any other DNA sequences, including, but not limited to transcription factor binding sites, repressor and activator protein binding sites, and any other sequences of nucleotides known to one of skill in the art to act directly or indirectly to regulate the amount of transcription from the promoter. A "constitutive" promoter is a promoter that is active in most tissues under most physiological and developmental conditions. An "inducible" promoter is a promoter that is physiologically or developmentally regulated, e.g. by the application of a chemical inducer.

The term "selectable marker" is a term familiar to one of ordinary skill in the art and is used herein to describe any genetic entity which, when expressed, can be used to select for a cell or cells containing the selectable marker. The term "reporter" may be used interchangeably with marker, although it is mainly used to refer to visible markers, such as green fluorescent protein (GFP). Selectable markers may be dominant or recessive or bidirectional.

As used herein, the term "operably linked" refers to a linkage of polynucleotide elements in a functional relationship. A nucleic acid is "operably linked" when it is placed into a functional relationship with another nucleic acid sequence. For instance, a transcription regulatory sequence is operably linked to a coding sequence if it affects the transcription of the coding sequence. Operably linked means that the DNA sequences being linked are typically contiguous and, where necessary to join two protein encoding regions, contiguous and in reading frame.

The terms "protein" or "polypeptide" are used interchangeably and refer to molecules consisting of a chain of amino acids, without reference to a specific mode of action, size, 3-dimensional structure or origin.

The term "gene" means a DNA fragment comprising a region (transcribed region), which is transcribed into an RNA molecule (e.g. an mRNA) in a cell, operably linked to suitable regulatory regions (e.g. a promoter). A gene will usually comprise several operably linked fragments, such as a promoter, a 5' leader sequence, a coding region and a 3' non-translated sequence (3' end) comprising a polyadenylation site. "Expression of a gene" refers to the process wherein a DNA region which is operably linked to appropriate regulatory regions, particularly a promoter, is transcribed into an RNA, which is biologically active, i.e. which is capable of being translated into a biologically active protein or peptide.

The term "homologous" when used to indicate the relation between a given (recombinant) nucleic acid or polypeptide molecule and a given host organism or host cell, is understood to mean that in nature the nucleic acid or polypeptide molecule is produced by a host cell or organisms of the same species, preferably of the same variety or strain. If homologous to a host cell, a nucleic acid sequence encoding a polypeptide will typically (but not necessarily) be operably linked to another (heterologous) promoter sequence and, if applicable, another (heterologous) secretory signal sequence and/or terminator sequence than in its natural environment. It is understood that the regulatory sequences, signal sequences, terminator sequences, etc. may also be homologous to the host cell. When used to indicate the relatedness of two nucleic acid sequences the term "homologous" means that one single-stranded nucleic acid sequence may hybridize to a complementary single-stranded nucleic acid sequence. The degree of hybridization may depend on a number of factors including the amount of identity between the sequences and the hybridization conditions such as temperature and salt concentration as discussed later.

The term "heterologous" when used with respect to a nucleic acid (DNA or RNA) or protein refers to a nucleic acid or protein that does not occur naturally as part of the organism, cell, genome or DNA or RNA sequence in which it is present, or that is found in a cell or location or locations in the genome or DNA or RNA sequence that differ from that in which it is found in nature. Heterologous nucleic acids or proteins are not endogenous to the cell into which it is introduced, but has been obtained from another cell or synthetically or recombinantly produced. Generally, though not necessarily, such nucleic acids encode proteins that are not normally produced by the cell in which the DNA is transcribed or expressed. Similarly exogenous RNA encodes for proteins not normally expressed in the cell in which the exogenous RNA is present. Heterologous nucleic acids and proteins may also be referred to as foreign nucleic acids or proteins. Any nucleic acid or protein that one of skill in the art would recognize as heterologous or foreign to the cell in which it is expressed is herein encompassed by the term heterologous nucleic acid or protein. The term heterologous also applies to non-natural combinations of nucleic acid or amino acid sequences, i.e. combinations where at least two of the combined sequences are foreign with respect to each other.

The phrases "pharmaceutical or pharmacologically acceptable" refers to molecular entities and compositions that do not produce or produce acceptable adverse, allergic or other untoward reaction when administered to an animal, such as, for example, a human, as appropriate. Whether certain adverse effects are acceptable is determined based on the severity of the disease. The preparation of a pharmaceutical composition that contains at least one chimeric polypeptide or additional active ingredient will be known to those of skill in the art in light of the present disclosure, as exemplified by Remington's Pharmaceutical Sciences, 18th Ed. Mack Printing Company, 1990, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the therapeutic or pharmaceutical compositions is contemplated.

Any reference to nucleotide or amino acid sequences accessible in public sequence databases herein refers to the version of the sequence entry as available on the filing date of this document.

DESCRIPTION OF EMBODIMENTS

The present invention seeks to provide modified serpin molecules wherein the modifications of residues within the reactive center loop (RCL) increase the specificity for bradykinin-generating proteases of the plasma contact system, particularly at least one of active forms of factor XII (FXII), plasma kallikrein (PK) and plasmin. These modified serpin molecules may be useful in therapy, for example for the treatment of bradykinin-mediated disease.

In a first aspect, the invention relates to a modified serpin molecule wherein one or more of residues of the positions P4, P3, P2, P1, P1', P2', P3' and P4' in the reactive center loop (RCL) of the serpin are mutated as compared to corresponding unmodified serpin (i.e. the corresponding wild-type serpin without the mutation). Preferably, the invention relates to a modified serpin molecule wherein one or more of residues of the positions P4, P3, P2, P1 and P1' in the reactive center loop (RCL) of the serpin are mutated as compared to corresponding unmodified serpin (i.e. the corresponding wild-type serpin without the mutation). The mutations preferably increase the inhibition of one or more of proteases selected from PK, plasmin and an active form of FXII, as compared to the corresponding unmodified serpin. The mutation preferably at least increase the inhibition of PK, as compared to the corresponding unmodified (i.e. wild-type) serpin. More preferably, the mutations at least increase the inhibition of PK and plasmin, or the mutations at least increase the inhibition of PK and an active form of FXII, both as compared to the corresponding unmodified serpin. Most preferably, the mutations at least increase the inhibition of all three of PK, plasmin and an active form of FXII, as compared to the corresponding unmodified serpin.

A thus modified serpin of the invention further preferably more strongly inhibits PK than the serpin inhibits thrombin. More preferably the modified serpin also more strongly inhibits PK than the serpin inhibits activated protein C (APC). A preferred modified serpin thus more strongly inhibits PK than the serpin inhibits either one of thrombin and APC.

It is further preferred that a modified serpin of the invention inhibits at least one of PK and an active form of FXII at least as strong as or preferably more strongly than that they are inhibited by C1 esterase inhibitor (C1INH). Preferably, the second-order inactivation rate constant ($M^{-1}$ $s^{-1}$) of the modified serpin for PK is increased by at least a factor 1.1, 1.2, 1.5, 2, 3, 4, 5, 10, 20, 50 or 100 as compared to inactivation rate constant of C1 esterase inhibitor for PK, and, the second-order inactivation rate constant of the modified serpin for an active form of FXII is increased by at least a factor 1.1, 1.2, 1.5, 2, 3, 4, 5, 6, 7, 8, 10, 20, 50 or 100 as compared to inactivation rate constant of C1 esterase inhibitor for an active form of FXII. Active forms of FXII are as described below. Second-order inactivation rate constants of serpins can be determined and calculated as e.g. described by Scott et al. (1986 J Clin Invest. 77(2):631-4).

A modified serpin of the invention may have one or more mutations in its reactive center loop (RCL). For example, the modified serpin may have at least one, two, three, four, five, six, seven, eight or nine mutations in its RCL. In particular, the modified serpin may have at least more than four mutations in its RCL. Alternatively, the modified serpin may have at most one, two, three, four, five, six, seven, eight, nine, ten, eleven, twelve, thirteen, fourteen, fifteen, sixteen, seventeen, eighteen, nineteen, or twenty mutations in its RCL.

The modified serpin of the invention preferably that has mutations in one or more of the P4, P3, P2, P1, P1', P2', P3' and P4' residues of its reactive center loop (RCL). Preferably, the residues at one, two, three or all four of positions P1, P2, P3, and P4 are mutated. For example, the residues at one or both of positions P1 and P2 and optionally P3 and/or P4 may be mutated. Preferably, at least position P1 is mutated, more preferably at least positions P1 and P2 are mutated, and most preferably at least positions P1, P2 and P4 are mutated. The RCL of the modified serpin may thus have mutations at position P1, P2, P3, or P4, at positions P1 and P2, P1 and P3, P1 and P4, P2 and P3, P2 and P4 or P3 and P4, at positions P1, P2 and P3, P1, P2 and P4, P1 P3 and P4 or P2, P3 and P4, or at all four positions P1, P2, P3 and P4. In one embodiment, the one or more mutations in P1, P2, P3 and/or P4 are the only mutations in the RCL of the modified serpin.

In another embodiment, other positions in the RCL may in addition be mutated, such as e.g. one or more of positions P1', P2', P3', and P4'. Preferably therefore, in addition to the above mutations at positions P1-P4, the residues at one, two, three or all four of positions P1', P2', P3', and P4' are mutated. For example, the residues at one or both of positions P1' and P2' and optionally P3' and/or P4' may be mutated. Preferably, at least position P1' is mutated, more preferably at least positions P1' and P2' are mutated, and most preferably at least positions P1', P2' and P3' are mutated. The RCL of the modified serpin may thus have mutations at position P1', P2', P3', or P4', at positions P1' and P2', P1' and P3', P1' and P4', P2' and P3', P2' and P4' or P3' and P4', at positions P1', P2' and P3', P1', P2' and P4', P1', P3' and P4' or P2', P3' and P4', or at all four positions P1', P2', P3' and P4'. The residues at other positions in the RCL may be unmutated wild-type residues.

RCL residues are numbered herein according to the Schechter-Berger nomenclature for substrates and inhibitors of serine proteases (Schechter & Berger 1967). This standard nomenclature allows the residue at specific positions in the RCL, such as positions P4, P3, P2 and/or P1, to be easily identified in any serpin sequence. The reactive center loop (RCL) of a serpin is typically about 27 residues in length and contains the scissile P1-P1' bond that is cleaved by the target protease (Crowther et al., 1992 Curr Opin Biotechnol August; 3(4):399-407). The RCL extends from strand 5 of beta sheet A to strand 1 of beta sheet C of the serpin. Residues P17 Glu, P15 Gly and P14 Thr are conserved in serpins. For example, the RCL of a serpin may comprise the consensus sequence P17 E, P16 E/K/R, P15 G, P14 T/S, P12-P9 (A/G/S) 4 (Hopkins et al., 1993; Irving et al. 2000). The RCL starts at residue P17 and usually ends at residue P5'. RCLs may be extended in some serpins, such as PCI and α1AT, by additional residues on the P' side. For example, the RCL of α1-antitrypsin consists of residues P17-P10' and the RCL of PCI consists of residues P17-P6'.

In one embodiment, the modified serpin comprises an RCL wherein preferably the P1 residue is lysine (K) or arginine (R). The modified serpin further preferably comprises an RCL wherein the P2 residue is not proline (P). A preferred modified serpin comprises an RCL wherein the P4 residue is serine (S). More preferably, the modified serpin comprises an RCL wherein the P1 residue is lysine (K) or arginine (R), wherein the P2 residue is not proline (P) and wherein the P4 residue is serine (S).

In one embodiment, a modified serpin of the invention preferably is a serpin of which the minimal amount of the serpin that inhibits PK activity by at least 50, 55, 60, 65, 70, 75, 80, 85, 90, 92, 94, 95, 96, 97, 98 or 99%, is an amount that inhibits thrombin activity by no more than 15, 12, 10, 7, 6, 5, 4, 3, 2 or 1%. Examples of modified serpins with this inhibition profile include serpins comprising an RCL wherein the residues P4-P1 of the RCL have an amino acid sequence selected from the group consisting of SMTR (SEQ ID NO: 12), SGQR (SEQ ID NO: 13), SVTR (SEQ ID NO: 14), SATR (SEQ ID NO: 15), SFNR (SEQ ID NO: 16), SWKK (SEQ ID NO: 17), SEAR (SEQ ID NO: 18), SVVK (SEQ ID NO: 19), SDYK (SEQ ID NO: 20), SVRK (SEQ ID NO: 21), SPRR (SEQ ID NO: 22), SMDR (SEQ ID NO: 23), SLGR (SEQ ID NO: 24), SKGR (SEQ ID NO: 25), SGNR (SEQ ID NO: 26), and SMHR (SEQ ID NO: 27), as well as serpins comprising an RCL wherein the residues P4-P1 of the RCL have the amino acid sequence SLLR (SEQ ID NO: 28) and wherein the P1' residue is selected from the group consisting of: Q, F, H, R, K, C, L, Y, N, I, D, W, E, V, M, A, T and P, of which K, L, Y, I, D, E, A, T, M, R and V are preferred, and I and V are most preferred.

In one embodiment, a modified serpin of the invention preferably is a serpin of which the minimal amount of the serpin that inhibits PK activity by at least 50, 55, 60, 65, 70, 75, 80, 85, 90, 92, 94, 95, 96, 97, 98 or 99%, is an amount that inhibits the activities of both thrombin and APC by no more than 15, 12, 10, 7, 6, 5, 4, 3, 2 or 1%. Examples of modified serpins with this inhibition profile include serpins comprising an RCL wherein the residues P4-P1 of the RCL have an amino acid sequence selected from the group consisting of SGQR (SEQ ID NO: 13), SATR (SEQ ID NO: 15), SFNR (SEQ ID NO: 16), SWKK (SEQ ID NO: 17), SEAR (SEQ ID NO: 18), SVVK (SEQ ID NO: 19), SDYK (SEQ ID NO: 20), SVRK (SEQ ID NO: 21), SPRR (SEQ ID NO: 22), SMDR (SEQ ID NO: 2), SLGR (SEQ ID NO: 24), SKGR (SEQ ID NO: 25), and SGNR (SEQ ID NO: 26), as well as serpins comprising an RCL wherein the residues P4-P1 of the RCL have the amino acid sequence SLLR (SEQ ID NO: 28) and wherein the P1' residue is selected from the group consisting of: Q, F, H, R, K, C, L, Y, N, I, D, W, E, V, M, A, T and P, of which K, L, Y, I, D, E, A, T, M, R and V are preferred, and I and V are most preferred.

In one embodiment, a modified serpin of the invention preferably is a serpin of which the minimal amount of the serpin that inhibits PK activity by at least 50, 55, 60, 65, 70, 75, 80, 85, 90, 92, 94, 95, 96, 97, 98 or 99%, is an amount that inhibits thrombin activity by no more than 15, 12, 10, 7, 6, 5, 4, 3, 2 or 1% and that further inhibits plasmin by at least 15, 19, 20, 30, 35, 40, 45, 50, 55, 60, 65, 70, 75, 80, 85, 90, 92, 94, 95, 96, 97, 98 or 99%. Examples of modified serpins with this inhibition profile include serpins comprising an RCL wherein the residues P4-P1 of the RCL have an amino acid sequence selected from the group consisting of SMTR (SEQ ID NO: 12), SVTR (SEQ ID NO: 14), SWKK (SEQ ID NO: 17), SVVK (SEQ ID NO: 19), SVRK (SEQ ID NO: 21), SPRR (SEQ ID NO: 22), SMDR (SEQ ID NO: 23) and SKGR (SEQ ID NO: 25), as well as serpins comprising an RCL wherein the residues P4-P1 of the RCL have the amino acid sequence SLLR (SEQ ID NO: 28) and wherein the P1' residue is selected from the group consisting of: Q, F, H, R, K, C, L, Y, N, I, D, W, E, V, M, A, T and P, of which K, L, Y, I, D, E, A, T, M, R and V are preferred, and I and V are most preferred.

In one embodiment, a modified serpin of the invention preferably is a serpin of which the minimal amount of the serpin that inhibits PK activity by at least 50, 55, 60, 65, 70, 75, 80, 85, 90, 92, 94, 95, 96, 97, 98 or 99%, is an amount that inhibits the activities of both thrombin and APC by no more than 15, 12, 10, 7, 6, 5, 4, 3, 2 or 1% and that further inhibits plasmin by at least 15, 19, 20, 30, 35, 40, 45, 50, 55, 60, 65, 70, 75, 80, 85, 90, 92, 94, 95, 96, 97, 98 or 99%. Examples of modified serpins with this inhibition profile include serpins comprising an RCL wherein the residues P4-P1 of the RCL have an amino acid sequence selected from the group consisting of SWKK (SEQ ID NO: 17), SVVK (SEQ ID NO: 19), SVRK (SEQ ID NO: 21), SPRR (SEQ ID NO: 22), SMDR (SEQ ID NO: 23) and SKGR (SEQ ID NO: 25), as well as serpins comprising an RCL wherein the residues P4-P1 of the RCL have the amino acid sequence SLLR (SEQ ID NO: 28) and wherein the P1' residue is selected from the group consisting of: Q, F, H, R, K, C, L, Y, N, I, D, W, E, V, M, A, T and P, of which K, L, Y, I, D, E, A, T, M, R and V are preferred, and I and V are most preferred.

In one embodiment, a modified serpin of the invention preferably is a serpin of which the minimal amount of the serpin that inhibits PK activity by at least 50, 55, 60, 65, 70, 75, 80, 85, 90, 92, 94, 95, 96, 97, 98 or 99%, is an amount that inhibits thrombin activity by no more than 15, 12, 10, 7, 6, 5, 4, 3, 2 or 1% and that further inhibits an active form of FXII by at least 15, 19, 20, 30, 35, 40, 45, 50, 55, 60, 65, 70, 75, 80, 85, 90, 92, 94, 95, 96, 97, 98 or 99%. Examples of modified serpins with this inhibition profile include serpins comprising an RCL wherein the residues P4-P1 of the RCL have an amino acid sequence selected from the group consisting of SMTR (SEQ ID NO: 12), SVTR (SEQ ID NO: 14), SATR (SEQ ID NO: 15), SLGR (SEQ ID NO: 24) and SKGR (SEQ ID NO: 25), as well as serpins comprising an RCL wherein the residues P4-P1 of the RCL have the amino acid sequence SLLR (SEQ ID NO: 28) and wherein the P1' residue is selected from the group consisting of: Q, F, H, R, K, C, L, Y, N, I, D, W, E, V, M, A, T and P, of which K, L, Y, I, D, E, A, T, M, R and V are preferred, and I and V are most preferred.

In one embodiment, a modified serpin of the invention preferably is a serpin of which the minimal amount of the serpin that inhibits PK activity by at least 50, 55, 60, 65, 70, 75, 80, 85, 90, 92, 94, 95, 96, 97, 98 or 99%, is an amount that inhibits the activities of both thrombin and APC by no more than 15, 12, 10, 7, 6, 5, 4, 3, 2 or 1% and that further inhibits an active form of FXII by at least 15, 19, 20, 30, 35, 40, 45, 50, 55, 60, 65, 70, 75, 80, 85, 90, 92, 94, 95, 96, 97, 98 or 99%. Examples of modified serpins with this inhibition profile include serpins comprising an RCL wherein the residues P4-P1 of the RCL have an amino acid sequence selected from the group consisting of SATR (SEQ ID NO: 15), SLGR (SEQ ID NO: 24) and SKGR (SEQ ID NO: 25), as well as serpins comprising an RCL wherein the residues P4-P1 of the RCL have the amino acid sequence SLLR (SEQ ID NO: 28) and wherein the P1' residue is selected from the group consisting of: Q, F, H, R, K, C, L, Y, N, I, D, W, E, V, M, A, T and P, of which K, L, Y, I, D, E, A, T, M, R and V are preferred, and I and V are most preferred.

In a preferred embodiment, a modified serpin of the invention preferably is a serpin of which the minimal amount of the serpin that inhibits PK activity by at least 50, 55, 60, 65, 70, 75, 80, 85, 90, 92, 94, 95, 96, 97, 98 or 99%, is an amount that inhibits thrombin activity by no more than 15, 12, 10, 7, 6, 5, 4, 3, 2 or 1%, that further inhibits plasmin by at least 15, 19, 20, 30, 35, 40, 45, 50, 55, 60, 65, 70, 75, 80, 85, 90, 92, 94, 95, 96, 97, 98 or 99% and that further inhibits an active form of FXII by at least 15, 19, 20, 30, 35, 40, 45, 50, 55, 60, 65, 70, 75, 80, 85, 90, 92, 94, 95, 96, 97, 98 or 99%. Examples of modified serpins with this inhibition profile include serpins comprising an RCL wherein the residues P4-P1 of the RCL have an amino acid sequence selected from the group consisting of SMTR (SEQ ID NO: 12), as well as serpins comprising an RCL wherein the residues P4-P1 of the RCL have the amino acid sequence SLLR (SEQ ID NO: 28) and wherein the P1' residue is selected from the group consisting of: Q, F, H, R, K, C, L, Y, N, I, D, W, E, V, M, A, T, and P, of which K, L, Y, I, D, E, A, T, M, R and V are preferred, and I and V are most preferred.

In a more preferred embodiment, a modified serpin of the invention preferably is a serpin of which the minimal amount of the serpin that inhibits PK activity by at least 50, 55, 60, 65, 70, 75, 80, 85, 90, 92, 94, 95, 96, 97, 98 or 99%, is an amount that inhibits the activities of both thrombin and APC by no more than 15, 12, 10, 7, 6, 5, 4, 3, 2 or 1%, that further inhibits plasmin by at least 15, 19, 20, 30, 35, 40, 45, 50, 55, 60, 65, 70, 75, 80, 85, 90, 92, 94, 95, 96, 97, 98 or 99% and that further inhibits an active form of FXII by at least 15, 19, 20, 30, 35, 40, 45, 50, 55, 60, 65, 70, 75, 80, 85, 90, 92, 94, 95, 96, 97, 98 or 99%. Examples of modified serpins with this inhibition profile include serpins comprising an RCL wherein the residues P4-P1 of the RCL have the amino acid sequence SLLR (SEQ ID NO: 28) and wherein the P1' residue is selected from the group consisting of: Q, F, H, R, K, C, L, Y, N, I, D, W, E, V, M, A, T and P, of which K, L, Y, I, D, E, A, T, M, R and V are preferred, and I and V are most preferred.

Preferably, the inhibition of PK activity (e.g. the above percentages inhibition) is determined in an in vitro assay on a chromogenic or fluorogenic PK substrate (e.g. the chromogenic Pro-Phe-Arg-p-nitroanilide peptide substrate L2120), preferably as described in the Examples herein.

Preferably, the inhibition of thrombin activity (e.g. the above percentages inhibition) is determined in an in vitro assay on a chromogenic or fluorogenic thrombin substrate (e.g. the fluorogenic benzyloxycarbonyl-Gly-Gly-Arg-7-amido-4-methylcoumarin peptide substrate 11140), preferably as described in the Examples herein.

Preferably, the inhibition of APC activity (e.g. the above percentages inhibition) is determined in an in vitro assay on a chromogenic or fluorogenic APC substrate (e.g. the chromogenic pyroGlu-Pro-Arg-p-nitroanilide peptide substrate S2366), preferably as described in the Examples herein.

Preferably, the inhibition of active forms of FXII activity (e.g. the above percentages inhibition) is determined in an in vitro assay on a chromogenic or fluorogenic FXII substrate (e.g. the chromogenic Pro-Phe-Arg-p-nitroanilide peptide substrate L2120), preferably as described in the Examples herein.

Preferably, the inhibition of plasmin activity (e.g. the above percentages inhibition) is determined in an in vitro assay on a chromogenic or fluorogenic plasmin substrate (e.g. the fluorogenic Val-Leu-Lys-7-amido-4-methylcoumarin peptide substrate 11390), preferably as described in the Examples herein.

In one embodiment, a modified serpin of the invention further preferably more strongly inhibits one or more of an active form of FXII, PK and plasmin, than the serpin inhibits one or more proteases selected from elastase, chymotrypsin FVIIa, FIXa, and FXa. More preferably, the modified serpin further more strongly inhibits one or more of an active form of FXII, PK and plasmin than the serpin inhibits FXIa. Preferably, the serpin is a serpin of which the minimal amount of the serpin that inhibits at least one of the activities of PK, plasmin and an active form of FXII by at least 50, 55, 60, 65, 70, 75, 80, 85, 90, 92, 94, 95, 96, 97, 98 or 99%, is an amount that inhibits at least one of the activities of elastase, chymotrypsin FVIIa, FIXa, FXIa and FXa by no more than 15, 12, 10, 7, 6, 5, 4, 3, 2 or 1%

An active form of FXII is herein understood to include all forms of FXII that have at least some proteolytic activity. Initiation of the contact system of the coagulation cascade requires a small spark of spontaneous enzymatic activity that is generated by FXII. This first pulse of enzymatic activity appears erratic and does not follow the rules of classic enzymatic behavior (Golas et al., 2013, Biomaterials 34, 607-620). This occurs when FXII changes its conformation during its binding to a negatively charged surface, after which it attains a limited amount of proteolytic activity (Ratnoff and Saito, 1979, Proc Natl Acad Sci USA 76, 1461-1463). Furthermore, FXII becomes increasingly susceptible to cleavage by plasma kallikrein (PK) and activated FXII (FXIIa) itself (Griffin, 1978, Proc Natl Acad Sci USA 75, 1998-2002). A single cleavage after an arginine residue at position 353 (R353; counted from the N-terminus in the mature FXII molecule) unlocks the full activity of FXIIa. This cleavage converts FXIIa from a single-chain molecule to a two chain form, termed α-FXIIa, which is held together by a disulfide bond. This molecular on/off switch of FXII was identified in cross-reactive material positive deficient persons in which this arginine was substituted by a proline residue (Hovinga et al., 1994, Blood 84, 1173-1181). Besides R353, several other protease-sensitive cleavage sites have been identified. Cleavage after an arginine at position 334 separates the surface-binding domains (~50 kDa) from the active protease domain (~30 kDa), resulting in fluid-phase activity of FXIIa. This soluble form of FXIIa is termed β-FXIIa or FXIIf. The capacity of FXIIa to cleave more of its own precursor is important to effectively induce contact activation; materials that do not support this reaction, do not trigger contact activation (Citarella et al., 1997, Br J Haematol 99, 197-205). All of these forms of FXII with at least some proteolytic activity are included in the term an active form of FXII. More preferably an active form of FXII includes at least one of α-FXIIa and β-FXIIa or FXIIf.

The modified serpin may show greater inhibition of PK, plasmin and/or an active form of FXII than inhibition of thrombin and one or more of APC, elastase, chymotrypsin FVIIa, FIXa, FXIa and FXa. For example, inhibition of PK, plasmin and/or an active form of FXII by the modified serpin may be 2 fold more, at least 3 fold more, at least 4 fold more, at least 5 fold more, at least 6 fold more, at least 7 fold more, at least 8 fold more, at least 9 fold more at least 10 fold more at least 100 or at least 1000 fold more than inhibition of thrombin, APC, elastase, chymotrypsin FVIIa, FIXa, FXIa and/or FXa by the modified serpin. In some embodiments, the modified serpin may inhibit PK, plasmin and/or an active form of FXII with a second-order rate constant (k2) that is at least 2 fold more, at least 3 fold more, at least 4 fold more, at least 5 fold more, at least 6 fold more, at least 7 fold more, at least 8 fold more, at least 9 fold more, at least 10 fold more at least 100 or at least 1000 fold more than the second-order rate constant for the inhibition of thrombin, APC, elastase, chymotrypsin FVIIa, FIXa, FXIa and/or FXa. Preferably the stoichiometry of inhibition of the modified serpin for PK, plasmin and/or an active form of FXII is 1.

In a preferred embodiment, a modified serpin as described herein may inhibit an active form of one or more of PK, plasmin and/or an active form of FXII but display no inhibition or substantially no inhibition of one or more of thrombin, APC, elastase, activated protein C, FVIIa, FIXa, FXa, FXIa and chymotrypsin. More preferably, the modified serpin display no inhibition or substantially no inhibition of any one of thrombin, APC, elastase, activated protein C, FVIIa, FIXa, FXa and chymotrypsin.

The one or more mutations in the reactive center loop (RCL) of the modified serpin may comprise or consist of a mutation at the P4 position. Preferably, the mutation is a substitution. The native P4 residue in the RCL of the wild-type serpin may be replaced with a non-native residue in the modified serpin. For example, the native Alanine (A) residue at the P4 position in the wild-type sequence of α1-antitrypsin (α1 AT) may be replaced with a residue other than A in the modified serpin. Preferably, the P4 residue in the wild-type serpin is replaced with a hydroxyl group containing residue a small or very small residue, of which a serine (S) residue is most preferred.

The one or more mutations in the reactive center loop (RCL) of the modified serpin may comprise or consist of a mutation at the P3 position. Preferably, the mutation is a substitution. The native P3 residue in the RCL of the wild-type serpin may be replaced with a non-native residue in the modified serpin. For example, the native isoleucine (I) residue at the P3 position in the wild-type serpin may be replaced with a residue other than I in the modified serpin. In some preferred embodiments, the P3 residue in the wild-type serpin is replaced with a hydrophobic residue, an aliphatic residue, a cycloalkenyl-associated residue, a negatively or positively charged residue or an asparagine (N) residue. More preferably, the P3 residue in the wild-type serpin is replaced with an aliphatic residue, of which methionine (M) and leucine (L) are most preferred.

The one or more mutations in the reactive center loop (RCL) of the modified serpin may comprise or consist of a mutation at the P2 position. Preferably, the mutation is a substitution. The native P2 residue in the RCL of the wild-type serpin may be replaced with a non-native residue in the modified serpin. For example, the native P residue at the P2 position in the wild-type sequence of the serpin may be replaced with a residue other than P in the modified serpin. In some preferred embodiments, the P2 residue in the wild-type serpin may be other than P (proline) residue. Preferably, the P3 residue in the wild-type serpin is replaced with a threonine (T) or leucine (L) residue.

The one or more mutations in the reactive center loop (RCL) of the modified serpin may comprise or consist of a mutation at the P1 position. Preferably, the mutation is a substitution. The native P1 residue in the RCL of the wild-type serpin may be replaced with a non-native residue in the modified serpin. For example, the native methionine (M) residue at the P1 position in the wild-type sequence of serpin may be replaced with a residue other than M in the modified serpin. In some preferred embodiments, the P1 residue in the wild-type serpin is replaced with a positively charged residue, of which R (arginine) or K (lysine) residue are more preferred and R (arginine) is most preferred.

Modified serpins where the P4-P1 residues are AIAR are not part of the invention, because contrary to what was disclosed in U.S. Pat. No. 4,973,668, we found that a modified serpin wherein the P4-P1 residues are AIAR does effectively inhibit thrombin.

Preferably, the modified serpin is non-immunogenic in a human. For example, the wild-type serpin may be a human serpin, preferably a human plasma serpin.

One or more residues in the modified serpin may be non-natural amino acids, modified amino acids or D-amino acids. The use of such amino acids is well-known to those of skill in the art.

In some preferred embodiments, the residues in the other positions of the RCL in the serpin may be unmodified i.e. they may be the native residues of the wild-type serpin sequence. The modified serpin may therefore comprise an RCL having a wild-type sequence with mutations at positions P4-P1 as described above.

In some embodiments the modified serpin can further comprise a mutation at the P1' position. Preferably, the mutation is a substitution. The native P1' residue in the RCL of the wild-type serpin may be replaced with a non-native residue in the modified serpin. For example, when the modified serpin according to the invention is an α1-antitrypsin (α1AT) serpin, the native S residue at the P1' position may be replaced with a residue other than S. In some preferred embodiments, the P1' residue of the modified serpin is replaced with a residue is selected from the group consisting of: Q, F, H, R, K, C, L, Y, N, I, D, W, E, V, M, A, T and P, of which K, L, Y, I, D, E, A, T, M, R and V are preferred, and I and V are most preferred.

In a preferred embodiment, the modified serpin of the invention comprises an RCL wherein the residues P4-P1' (i.e. P4 to P1 prime) of the RCL have an amino acid sequence selected from the group consisting of SMTRQ (SEQ ID NO: 29), SMTRF (SEQ ID NO: 30), SMTRH (SEQ ID NO: 31), SMTRR (SEQ ID NO: 32), SMTRK (SEQ ID NO: 33), SMTRC (SEQ ID NO: 34), SMTRL (SEQ ID NO: 35), SMTRY (SEQ ID NO: 36), SMTRN (SEQ ID NO: 37), SMTRI (SEQ ID NO: 38), SMTRD (SEQ ID NO: 39), SMTRW (SEQ ID NO: 40), SMTRE (SEQ ID NO: 41), SMTRV (SEQ ID NO: 42), SMTRM (SEQ ID NO: 43), SMTRA (SEQ ID NO: 44), SMTRT (SEQ ID NO: 45), SMTRP (SEQ ID NO: 46), SGQRQ (SEQ ID NO: 47), SGQRF (SEQ ID NO: 48), SGQRH (SEQ ID NO: 49), SGQRR (SEQ ID NO: 50), SGQRK (SEQ ID NO: 51), SGQRC (SEQ ID NO: 52), SGQRL (SEQ ID NO: 53), SGQRY (SEQ ID NO: 54), SGQRN (SEQ ID NO: 55), SGQRI (SEQ ID NO: 56), SGQRD (SEQ ID NO: 57), SGQRW (SEQ ID NO: 58), SGQRE (SEQ ID NO: 59), SGQRV (SEQ ID NO: 60), SGQRM (SEQ ID NO: 61), SGQRA (SEQ ID NO: 62), SGQRT (SEQ ID NO: 63), SGQRP (SEQ ID NO: 64), SVTRQ (SEQ ID NO: 65), SVTRF (SEQ ID NO: 66), SVTRH (SEQ ID NO: 67), SVTRR (SEQ ID NO: 68), SVTRK (SEQ ID NO: 69), SVTRC (SEQ ID NO: 70), SVTRL (SEQ ID NO: 71), SVTRY (SEQ ID NO: 72), SVTRN (SEQ ID NO: 73), SVTRI (SEQ ID NO: 74), SVTRD (SEQ ID NO: 75), SVTRW (SEQ ID NO: 76), SVTRE (SEQ ID NO: 77), SVTRV (SEQ ID NO: 78), SVTRM (SEQ ID NO: 79), SVTRA (SEQ ID NO: 80), SVTRT (SEQ ID NO: 81), SVTRP (SEQ ID NO: 82), SATRQ (SEQ ID NO: 83), SATRF (SEQ ID NO: 84), SATRH (SEQ ID NO: 85), SATRR (SEQ ID NO: 86), SATRK (SEQ ID NO: 87), SATRC (SEQ ID NO: 88), SATRL (SEQ ID NO: 89), SATRY (SEQ ID NO: 90), SATRN (SEQ ID NO: 91), SATRI (SEQ ID NO: 92), SATRD (SEQ ID NO: 93), SATRW (SEQ ID NO: 94), SATRE (SEQ ID NO: 95), SATRV (SEQ ID NO: 96), SATRM (SEQ ID NO: 97), SATRA (SEQ ID NO: 98), SATRT (SEQ ID NO: 99), SATRP (SEQ ID NO: 100), SFNRQ (SEQ ID NO: 101), SFNRF (SEQ ID NO: 102), SFNRH (SEQ ID NO: 103), SFNRR (SEQ ID NO: 104), SFNRK (SEQ ID NO: 105), SFNRC (SEQ ID NO: 106), SFNRL (SEQ ID NO: 107), SFNRY (SEQ ID NO: 108), SFNRN (SEQ ID NO: 109), SFNRI (SEQ ID NO: 110), SFNRD (SEQ ID NO: 111), SFNRW (SEQ ID NO: 112), SFNRE (SEQ ID NO: 113), SFNRV (SEQ ID NO: 114), SFNRM (SEQ ID NO: 115), SFNRA (SEQ ID NO: 116), SFNRT (SEQ ID NO: 117), SFNRP (SEQ ID NO: 118), SWKKQ (SEQ ID NO: 119), SWKKF (SEQ ID NO: 120), SWKKH (SEQ ID NO: 121), SWKKR (SEQ ID NO: 122), SWKKK (SEQ ID NO: 123), SWKKC (SEQ ID NO: 124), SWKKL (SEQ ID NO: 125), SWKKY (SEQ ID NO: 126), SWKKN (SEQ ID NO: 127), SWKKI (SEQ ID NO: 128), SWKKD (SEQ ID NO: 129), SWKKW (SEQ ID NO: 130), SWKKE (SEQ ID NO: 131), SWKKV (SEQ ID NO: 132), SWKKM (SEQ ID NO: 133), SWKKA (SEQ ID NO: 134), SWKKT (SEQ ID NO: 135), SWKKP (SEQ ID NO: 136), SEARQ (SEQ ID NO: 137), SEARF (SEQ ID NO: 138), SEARH (SEQ ID NO: 139), SEARR (SEQ ID NO: 140), SEARK (SEQ ID NO: 141), SEARC (SEQ ID NO: 142), SEARL (SEQ ID NO: 143), SEARY (SEQ ID NO: 144, SEARN (SEQ ID NO: 145), SEARI (SEQ ID NO: 146), SEARD (SEQ ID NO: 147), SEARW (SEQ ID NO: 148), SEARE (SEQ ID NO: 149), SEARV (SEQ ID NO: 150), SEARM (SEQ ID NO: 151), SEARA (SEQ ID NO: 152), SEART (SEQ ID NO: 153), SEARP (SEQ ID NO: 154), SVVKQ (SEQ ID NO: 155), SVVKF (SEQ ID NO: 156), SVVKH (SEQ ID NO: 157), SVVKR (SEQ ID NO: 158), SVVKK (SEQ ID NO: 159), SVVKC (SEQ ID NO: 160), SVVKL (SEQ ID NO: 161), SVVKY (SEQ ID NO: 162), SVVKN (SEQ ID NO: 163), SVVKI (SEQ ID NO: 164), SVVKD (SEQ ID NO: 165), SVVKW (SEQ ID NO: 166), SVVKE (SEQ ID NO: 167), SVVKV (SEQ ID NO: 168), SVVKM (SEQ ID NO: 169), SVVKA (SEQ ID NO: 170), SVVKT (SEQ ID NO: 171), SVVKP (SEQ ID NO: 172), SDYKQ (SEQ ID NO: 173), SDYKF (SEQ ID NO: 174), SDYKH (SEQ ID NO: 175), SDYKR (SEQ ID NO: 176), SDYKK (SEQ ID NO: 177), SDYKC (SEQ ID NO: 178), SDYKL (SEQ ID NO: 179), SDYKY (SEQ ID NO: 180), SDYKN (SEQ ID NO: 181), SDYKI (SEQ ID NO: 182), SDYKD (SEQ ID NO: 183), SDYKW (SEQ ID NO: 184), SDYKE (SEQ ID NO: 185), SDYKV (SEQ ID NO: 186), SDYKM (SEQ ID NO: 187), SDYKA (SEQ ID NO: 188), SDYKT (SEQ ID NO: 189), SDYKP (SEQ ID NO: 190), SVRKQ (SEQ ID NO: 191), SVRKF (SEQ ID NO: 192), SVRKH (SEQ ID NO: 193), SVRKR (SEQ ID NO: 194), SVRKK (SEQ ID NO: 195), SVRKC (SEQ ID NO: 196), SVRKL (SEQ ID NO: 197), SVRKY (SEQ ID NO: 198), SVRKN (SEQ ID NO: 199), SVRKI (SEQ ID NO: 200), SVRKD (SEQ ID NO: 201), SVRKW (SEQ ID NO: 202), SVRKE (SEQ ID NO: 203), SVRKV (SEQ ID NO: 204), SVRKM (SEQ ID NO: 205), SVRKA (SEQ ID NO: 206), SVRKT (SEQ ID NO: 207), SVRKP (SEQ ID NO: 208), SPRRQ (SEQ ID NO: 209), SPRRF (SEQ ID NO: 210), SPRRH (SEQ ID NO: 211), SPRRR (SEQ ID NO: 212), SPRRK (SEQ ID NO: 213), SPRRC (SEQ ID NO: 214), SPRRL (SEQ ID NO: 215), SPRRY (SEQ ID NO: 216), SPRRN (SEQ ID NO: 217), SPRRI (SEQ ID NO: 218), SPRRD (SEQ ID NO: 219), SPRRW (SEQ ID NO: 220), SPRRE (SEQ ID NO: 221), SPRRV (SEQ ID NO: 222), SPRRM (SEQ ID NO: 223), SPRRA (SEQ ID NO: 224), SPRRT (SEQ ID NO: 225), SPRRP (SEQ ID NO: 226), SMDRQ (SEQ ID NO: 227), SMDRF (SEQ ID NO: 228), SMDRH (SEQ ID NO: 229), SMDRR (SEQ ID NO: 230), SMDRK (SEQ ID NO: 231), SMDRC (SEQ ID NO: 232), SMDRL (SEQ ID NO: 233), SMDRY (SEQ ID NO: 234), SMDRN (SEQ ID NO: 235), SMDRI (SEQ ID NO: 236), SMDRD (SEQ ID NO: 237), SMDRW (SEQ ID NO: 238), SMDRE (SEQ ID NO: 239), SMDRV (SEQ ID NO: 240), SMDRM (SEQ ID NO: 241), SMDRA (SEQ ID NO: 242), SMDRT (SEQ ID NO: 243), SMDRP (SEQ ID NO: 244), SLGRQ (SEQ ID NO: 245), SLGRF (SEQ ID NO: 246), SLGRH (SEQ ID NO: 247), SLGRR (SEQ ID NO: 248), SLGRK (SEQ ID NO: 249), SLGRC (SEQ ID NO: 250), SLGRL (SEQ ID NO: 251), SLGRY (SEQ ID NO: 252), SLGRN (SEQ ID NO: 253), SLGRI (SEQ ID NO: 254), SLGRD (SEQ ID NO: 255), SLGRW (SEQ ID NO: 256), SLGRE (SEQ ID NO: 257), SLGRV (SEQ ID NO: 258), SLGRM (SEQ ID NO: 259), SLGRA (SEQ ID NO: 260), SLGRT (SEQ ID NO: 261), SLGRP (SEQ ID NO: 262), SKGRQ (SEQ ID NO: 263), SKGRF (SEQ ID NO: 264), SKGRH (SEQ ID NO: 265), SKGRR (SEQ ID NO: 266), SKGRK (SEQ ID NO: 267), SKGRC (SEQ ID NO: 268), SKGRL (SEQ ID NO: 269), SKGRY (SEQ ID NO: 270), SKGRN (SEQ ID NO: 271), SKGRI (SEQ ID NO: 272), SKGRD (SEQ ID NO: 273), SKGRW (SEQ ID NO: 274), SKGRE (SEQ ID NO: 275), SKGRV (SEQ ID NO: 276), SKGRM (SEQ ID NO: 277), SKGRA (SEQ ID NO: 278), SKGRT (SEQ ID NO: 279), SKGRP (SEQ ID NO: 280), SGNRQ (SEQ ID NO: 281), SGNRF (SEQ ID NO: 282), SGNRH (SEQ ID NO: 283), SGNRR (SEQ ID NO: 284), SGNRK (SEQ ID NO: 285), SGNRC (SEQ ID NO: 286), SGNRL (SEQ ID NO: 287), SGNRY (SEQ ID NO: 288), SGNRN (SEQ ID NO: 289), SGNRI (SEQ ID NO: 290), SGNRD (SEQ ID NO: 291), SGNRW (SEQ ID NO: 292), SGNRE (SEQ ID NO: 293), SGNRV (SEQ ID NO: 294), SGNRM (SEQ ID NO: 295), SGNRA (SEQ ID NO: 296), SGNRT (SEQ ID NO: 297), SGNRP (SEQ ID NO: 298), SMHRQ (SEQ ID NO: 299), SMHRF (SEQ ID NO: 300), SMHRH (SEQ ID NO: 301), SMHRR (SEQ ID NO: 302), SMHRK (SEQ ID NO: 303), SMHRC (SEQ ID NO: 304), SMHRL (SEQ ID NO: 305), SMHRY (SEQ ID NO: 306), SMHRN (SEQ ID NO: 307), SMHRI (SEQ ID NO: 308), SMHRD (SEQ ID NO: 309), SMHRW (SEQ ID NO: 310), SMHRE (SEQ ID NO: 311), SMHRV (SEQ ID NO: 312), SMHRM (SEQ ID NO: 313), SMHRA (SEQ ID NO: 314), SMHRT (SEQ ID NO: 315), SMHRP (SEQ ID NO: 316), SLLRQ (SEQ ID NO: 317), SLLRF (SEQ ID NO: 318), SLLRH (SEQ ID NO: 319), SLLRR (SEQ ID NO: 320), SLLRK (SEQ ID NO: 321), SLLRC (SEQ ID NO: 322), SLLRL (SEQ ID NO: 323), SLLRY (SEQ ID NO: 324), SLLRN (SEQ ID NO: 325), SLLRI (SEQ ID NO: 326), SLLRD (SEQ ID NO: 327), SLLRW (SEQ ID NO: 328), SLLRE (SEQ ID NO: 329), SLLRV (SEQ ID NO: 330), SLLRM (SEQ ID NO: 331), SLLRA (SEQ ID NO: 332), SLLRT (SEQ ID NO: 333) and SLLRP (SEQ ID NO: 334).

A modified serpin as described herein may display the secondary structure of the wild-type serpin, for example a modified serpin may display a structure comprising 3 beta sheets, 8-9 alpha helices and a flexible RCL of about 20 residues.

A modified serpin as described herein may comprise the sequence of a wild-type (i.e. unmodified) serpin, preferably a mature wild-type serpin, with one or more mutations in the RCL thereof as described above, and optionally one or more additional mutations outside the RCL. The sequences of wild-type serpins are well-known in the art, and may include as set out herein. The sequences of wild-type serpins may include the sequence of mature wild-type proteins.

The mature α1-antitrypsin (α1AT) (SERPINA1) sequence corresponds to SEQ ID NO: 1. The mature α1-antichymotrypsin (SERPINA3) sequence corresponds to SEQ ID NO: 2. The mature C1-esterase inhibitor (SERPING1) sequence corresponds SEQ ID NO: 3. The mature a2-antiplasmin (SERPINF2) sequence corresponds to SEQ ID NO: 4. The mature antithrombin (ATIII) (SERPINC1) sequence corresponds to SEQ ID NO: 5. The mature heparin cofactor II (HCII) (SERPIND1) sequence corresponds SEQ ID NO: 6. The mature protein C inhibitor (PCI) (SERPINA5) sequence corresponds to SEQ ID NO: 7. The mature kallistatin (SERPINA4) sequence corresponds to SEQ ID NO: 8. The mature plasminogen activator inhibitor (SERPINE1) sequence corresponds to SEQ ID NO: 9. The mature protease nexin 1 (SERPINE2) sequence corresponds to SEQ ID NO: 10. The mature protein Z-dependent protease inhibitor (SERPINA10) sequence corresponds to SEQ ID NO: 11.

Other than mutations of residues in the RCL as described above, a modified serpin may have 50 or fewer amino acid residues altered relative to a wild-type serpin amino acid sequence (for example the mature serpin sequence of one of SEQ ID NO.'s: 1-11, preferably SEQ ID NO: 1), preferably 45 or fewer, 40 or fewer, 30 or fewer, 20 or fewer, 15 or fewer, 10 or fewer, 5 or fewer or 3 or fewer. For example, a modified serpin may comprise the sequence of a wild-type serpin with 50 or fewer, 45 or fewer, 40 or fewer, 30 or fewer, 20 or fewer, 15 or fewer, 10 or fewer, 5 or fewer or 3 or fewer amino acid residues mutated or altered, in addition to the one, two, three, four or five amino acid residues in the RCL of the serpin that are mutated or altered as described above (i.e. the residues at positions P4-P1').

An amino acid residue in the wild-type amino acid sequence may be altered or mutated by insertion, deletion or substitution, preferably substitution for a different amino acid residue. Such alterations may be caused by one or more of addition, insertion, deletion or substitution of one or more nucleotides in the encoding nucleic acid.

The modified serpin may share at least 50% sequence identity with the wild-type amino acid sequence of a wild-type serpin, for example the mature serpin sequence of any one of SEQ ID NO.'s: 1-11, preferably SEQ ID NO:1, at least 55%, at least 60%, at least 65% at least 70%, at least about 80%, at least 90%, at least 95%, at least 98% or at least 99% sequence identity. For example, a modified serpin may comprise an amino acid sequence having at least 50% sequence identity to residues, whereby the P4-P1' residues in the RCL are modified as herein described.

In a preferred embodiment, the modified serpin molecule comprises an amino acid sequence that has at least 70%, at least 75%, at least 80%, at least 85%, at least 90%, at least 95%, at least 98%, or at least 99% sequence identity to the sequence of a wild-type serpin, wherein the wild type serpin is selected from the group consisting of α1-antitrypsin (α1AT) (SERPINA1), α1-antichymotrypsin (SERPINA3), C1-esterase inhibitor (SERPING1), a2-antiplasmin (SERPINF2), antithrombin (ATIII) (SERPINC1), heparin cofactor II (HCII) (SERPIND1), protein C inhibitor (PCI) (SERPINA5), Kallistatin (SERPINA4), Plasminogen activator inhibitor (SERPINE1), Protease nexin 1 (SERPINE2) and Protein Z-dependent protease inhibitor (SERPINA10). α1-antitrypsin (α1 AT) (SERPINA1 Gene ID 5265) may have the reference amino acid sequence of NP_000286.3 GI:50363217 (SEQ ID NO: 1) and may be encoded by the reference nucleotide sequence of NM_000295.4 GI:189163524. α1-antichymotrypsin (SERPINA3; Gene ID 12) may have the reference amino acid sequence of NP_001076.2 GI:50659080 (SEQ ID NO: 2) and may be encoded by the reference nucleotide sequence of NM_001085.4 GI:73858562. C1-esterase inhibitor (SERPING1; Gene ID 710) may have the reference amino acid sequence of NP_000053.2 GI: 73858568(SEQ ID NO: 3) and may be encoded by the reference nucleotide sequence of NM_000062.2GI:73858567. α2-antiplasmin (SERPINF2 Gene ID 5345) may have the reference amino acid sequence of NP_000925.2 encoded by the reference nucleotide sequence of GI:260064047 GI:115583663 (SEQ ID NO: 4) and may be NM 001165920.1. Antithrombin (ATIII) (SERPINC1 Gene ID 462) may have the reference amino acid sequence of NP_000479.1 GI: 4502261 (SEQ ID NO: 5) and may be encoded by the reference nucleotide sequence of NM_000488.3 GI:254588059. Heparin cofactor II (HCII) (SERPIND1 Gene ID3053) may have the reference amino acid sequence of NP_000176.2 GI: 73858566 (SEQ ID NO: 6) and may be encoded by the reference nucleotide sequence of NM 000185.3 GI:73858565. Protein C inhibitor (PCI) (SERPINA5 Gene ID 5104) may have the reference amino acid sequence of NP_000615.3 GI: 194018472 and may (SEQ ID NO: 7) be encoded by the reference nucleotide sequence of NM 000624.5 GI:401782581. Kallistatin (SERPINA4 Gene ID 5267) may have the reference amino acid sequence of NP 006206.2 GI: 21361302 (SEQ ID NO: 8) and may be encoded by the reference nucleotide sequence of NM 006215.2 GI:21361301. Plasminogen activator inhibitor-1 (SERPINE1 Gene ID 5054) may have the reference amino acid sequence of NP_000593.1 GI: 10835159 (SEQ ID NO:9) and may be encoded by the reference nucleotide sequence of NM 000602.4 GI: 383286745. Protease nexin 1 (PNI) (SERPINE2; Gene ID 5270) may have the reference amino acid sequence of NP_001130000.1 GI: 24307907, NP_001130002.1 GI: 211904152 or NP_006207.1 GI: 211904156 (SEQ ID NO: 10) and may be encoded by the reference nucleotide sequence of NM_001136528.1 GI: 211904151, NM_001136530.1 GI: 211904155 or NM 006216.3 GI: 211904150. Protein Z-dependent inhibitor (PZI) (SERPINA10; Gene ID 51156) may have the reference amino acid sequence of NP_057270.1 GI: 7705879 (SEQ ID NO: 11) and may be encoded by the reference nucleotide sequence of NM_016186.2 GI: 154759289.

A modified serpin may further comprise one or more residues that are conserved in wild-type serpin sequences. For example, a modified serpin may comprise some or all of the following residues (numbered according to their position in α1AT): 33F, 49N, 53S, 54P, 56S, 61 L, 67G, 72T, 80L, 130F, 147F, 157I, 158N, 161V, 165T, 167G, 169I, 180T, 184L, 186N, 190F, 191K, 192G, 194W, 198F, 203T, 208F, 218V, 220M, 221M, 277Y, 254L, 255P, 289P, 290K, 299L, 303L, 307G, 312F, 316A, 327L, 334H, 342E, 344G, 347A, 369P, 370F, 383L, 384F, 386G, and 391 P (Irving et al 2008).

The corresponding conserved residues in other serpin sequences may be readily determined using routine sequence analysis.

In another embodiment, the invention relates to a modified serpin molecule wherein the modified serpin molecule is α1AT (SEQ ID NO: 1). Preferably the modified α1AT according to the invention comprises an amino acid sequence that has at least 70% at least 75%, at least 80%, at least 85%, at least 90%, at least 95%, at least 98%, or at least 99% sequence identity to the sequence of a wild-type α1AT, whereby the P4-P1' residues in the RCL are modified as herein described.

A modified serpin may further comprise modifications in the wild-type sequence that reduce the susceptibility to oxidation. The modified serpin according to the invention may be modified by one or more amino acid substitutions, deletions or insertions to confer reduced susceptibility to oxidation, thereby decreasing degradation of the polypeptide and extending the shelf-life and biological activity of the polypeptide under typical storage, handling and use conditions.

The amino acids that are particularly susceptible to oxidation include methionine (M), cysteine (C), histidine(H), and tyrosine (Y); however, oxidation products have also been observed for proline (P), lysine(K), and arginine (R) (Amici et al., J Biol. Chem. 264:3341-46. 1989; Stadtman, Free Radic Biol Med. 9:315-25, 1990). Amino acid oxidation is typically initiated by the presence of OH— or O$_2$-reactive species, which may be generated by ionizing radiation (Berlett et al., Proc Natl Acad Sci USA. 1990; 87:389-93). Oxygen reactive species target the protein backbone, stealing a hydrogen atom from an amino acid side group to form a carbon radical. Formation of this carbon radical may ultimately lead to weakened peptide bonds subject to cleavage and protein fragmentation. Oxidation of either methionine (M) 351 or methionine (M) 358 in al AT has been described to cause loss of its inhibitory activity against elastase (Taggart et al., 2000, J Biol Chem. 275: 27258-65). Additionally, it has been described that cysteine (C) 232 in al AT appears the residue most susceptible to oxidation (Griffiths et al J Biol Chem. 2002 Jul. 12; 277 (28):25486-92).

In one embodiment, therefore, one or more of the residues solvent exposed methionine (M) or cysteine (C) residues of the modified serpin according to the invention have been replaced with an amino acid that is not sensitive to oxidation. In the modified serpin of the invention the M (methionine) residue corresponding to the M at position 358 (i.e. position P1 in the RCL) of al AT is preferably replaced as described herein above.

More preferably, in addition, at least the M (methionine) residue corresponding to the M at position 351 (i.e. position P8 in the RCL) of al AT is replaced with an I (isoleucine), L (leucine) or V (valine) residue, most preferably a V (valine) residue. Alternatively or in addition, at least the C (cysteine) residue corresponding to the C at position 232 is replaced, preferably with a serine (S) residue. In a preferred embodiment, the modified serpin (α1AT or other serpin) according to the invention may further comprise modification that reduce the susceptibility to oxidation. The modified serpin according to the invention may be further modified by one or more amino acid substitutions, deletions or insertions to confer reduced susceptibility to oxidation, thereby decreasing degradation of the polypeptide and extending the shelf-life and biological activity of the polypeptide under typical storage, handling and use conditions.

Sequence comparisons are preferably made over the full-length of the relevant sequence described herein.

In a second aspect, the invention relates to a nucleic acid molecule comprising a nucleotide sequence encoding a modified serpin according to the invention.

In a third aspect, the invention relates to a vector comprising a nucleic acid molecule according to the invention. Optionally, the vector according to the invention is a gene therapy vector.

Preferably, the a gene therapy vector is a viral gene therapy vector, e.g. a viral gene therapy vector selected from gene therapy vectors based on an adenovirus, an adeno-associated virus (AAV), a herpes virus, a pox virus, an oncolytic virus vector and a retrovirus. A preferred viral gene therapy vector is an AAV or Lentiviral vector.

The term "vector" is used to refer to a carrier nucleic acid molecule into which a nucleic acid sequence can be inserted for introduction into a cell where it can be replicated. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, lentivirus, and plant viruses), and artificial chromosomes (e.g., YACs). One of skill in the art would be well equipped to construct a vector through standard recombinant techniques, which are described in Sambrook et al, 1989 and Ausubel et al, 1996, both incorporated herein by reference. In addition to encoding a modified polypeptide such as modified gelonin, a vector may encode non-modified polypeptide sequences such as a tag or targeting molecule. A targeting molecule is one that directs the desired nucleic acid to a particular organ, tissue, cell, or other location in a subject's body.

The term "expression vector" refers to a vector containing a nucleic acid sequence coding for at least part of a gene product capable of being transcribed. Expression vectors can contain a variety of "control sequences," which refer to nucleic acid sequences necessary for the transcription and possibly translation of an operably linked coding sequence in a particular host organism. In addition to control sequences that govern transcription and translation, vectors and expression vectors may contain nucleic acid sequences that serve other functions as well and are described Techniques for the introduction of nucleic acid into cells are well established in the art and any suitable technique may be employed, in accordance with the particular circumstances. For eukaryotic cells, suitable techniques may include calcium phosphate transfection, DEAE-Dextran, electroporation, liposome-mediated transfection and transduction using retrovirus or other virus, e.g. adenovirus, AAV, lentivirus or vaccinia. For microbial, e.g. bacterial, cells, suitable techniques may include calcium chloride transformation, electroporation and transfection using bacteriophage. Marker genes such as antibiotic resistance or sensitivity genes may be used in identifying clones containing nucleic acid of interest, as is well-known in the art. The introduced nucleic acid may be on an extra-chromosomal vector within the cell or the nucleic acid may be integrated into the genome of the host cell. Integration may be promoted by inclusion of sequences within the nucleic acid or vector which promote recombination with the genome, in accordance with standard techniques. The introduction may be followed by expression of the nucleic acid to produce the encoded modified serpin. In some embodiments, host cells (which may include cells actually transformed although more likely the cells will be descendants of the transformed cells) may be cultured in vitro under conditions for expression of the nucleic acid, so that the encoded serpin polypeptide is produced, inducible promoter is used, expression may require the activation of the inducible promoter.

In a fourth aspect, the invention relates to a host cell comprising a vector according to the invention, which host cell expresses a modified serpin according to invention.

The cell preferably is an isolated cell or a cultured cell. Among the host cells that may be employed are prokaryotes, yeast or higher eukaryotic cells. Prokaryotes include gram negative or gram positive organisms, for example *Escherichia coli* or bacilli. Higher eukaryotic cells include insect cells and established cell lines of mammalian origin. Examples of suitable mammalian host cell lines include the COS-7 line of monkey kidney cells (Gluzman et al., 1981, Cell 23:175), L cells, 293 cells, C127 cells, 3T3 cells, Chinese hamster ovary (CHO) cells, HeLa cells, BHK cell lines, and the CVI/EBNA cell line derived from the African green monkey kidney cell line CVI as described by McMahan et al., 1991, EMBO J. 10: 2821. Appropriate cloning and expression vectors for use with bacterial, fungal, yeast, and mammalian cellular hosts are described by Pouwels et al. (Cloning Vectors: A Laboratory Manual, Elsevier, New York, 1985).

The transformed cells can be cultured under conditions that promote which host cell expresses a modified serpin according to invention. Thus in one aspect the invention relates to a method for producing a modified serpin according to invention, the method comprising the step of cultivating a cell comprising at least one expression vector as defined herein, under conditions conducive to expression of a modified serpin according to invention, optionally, recovering the modified serpin according to invention.

A modified serpin according to invention can be recovered by conventional protein purification procedures, including e.g. protein A-Sepharose, hydroxylapatite chromatography, gel electrophoresis, dialysis, or affinity chromatography (see e.g. Low et al., 2007, J. Chromatography B, 848:48-63; Shukla et al., 2007, J. Chromatography B, 848:28-39

In a fifth aspect, the invention relates to a pharmaceutical composition comprising and/or consisting of a modified serpin according to the invention, a nucleic acid according to the invention, a vector or gene therapy vector according to the invention, or a host cell according to the invention and a pharmaceutically acceptable excipient.

The pharmaceutical composition further preferably comprises at least one pharmaceutically acceptable carrier. The pharmaceutically acceptable carrier such as an adjuvant, or vehicle, is for administration of the antibody or antibody fragment to a subject. Said pharmaceutical composition can be used in the methods of treatment described herein below by administration of an effective amount of the composition to a subject in need thereof. The term "subject", as used herein, refers to all animals classified as mammals and includes, but is not restricted to, primates and humans. The subject is preferably a male or female human of any age or race.

The term "pharmaceutically acceptable carrier", as used herein, is intended to include any and all solvents, dispersion media, coatings, antibacterial and antifungal agents, isotonic and absorption delaying agents, and the like, compatible with pharmaceutical administration (see e.g. "Handbook of Pharmaceutical Excipients", Rowe et al eds. 7$^{th}$ edition, 2012, on the World-Wide Web at pharmpress.com). The use of such media and agents for pharmaceutically active substances is well known in the art. Except insofar as any conventional media or agent is incompatible with the active compound, use thereof in the compositions is contemplated. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter ions such as sodium; metal complexes (e.g. $Zn^{2+}$-protein complexes); and/or non-ionic surfactants such as TWEEN™, PLURONICS™ or polyethylene glycol (PEG).

Supplementary active compounds can also be incorporated into the pharmaceutical composition of the invention. Thus, in a particular embodiment, the pharmaceutical composition of the invention may also contain more than one active compound as necessary for the particular indication being treated, preferably those with complementary activities that do not adversely affect each other. For example, it may be desirable to further provide a chemotherapeutic agent, a cytokine, an analgesic agent, or an immunomodulating agent, e.g. an immunosuppressive agent or an immunostimulating agent. The effective amount of such other active agents depends, among other things, on the amount of antibody of the invention present in the pharmaceutical composition, the type of disease or disorder or treatment, etc.

In an embodiment, the modified serpin according to the invention is prepared with carriers that will protect said compound against rapid elimination from the body, such as a controlled release formulation, including implants and microencapsulated delivery systems, e.g. liposomes. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. Liposomal suspensions, including targeted liposomes can also be used as pharmaceutically acceptable carriers. These can be prepared according to methods known to those skilled in the art, for example, as described in U.S. Pat. No. 4,522,811 or WO2010/095940.

The administration route of the modified serpin according to the invention can be parenteral. The term "parenteral" as used herein includes intravenous, intra-arterial, intralymphatic, intraperitoneal, intramuscular, subcutaneous, rectal or vaginal administration. The intravenous forms of parenteral administration are preferred. By "systemic administration" is meant oral, intravenous, intraperitoneal and intramuscular administration. The amount of the modified serpin required for therapeutic or prophylactic effect will, of course, vary with the modified serpin chosen, the nature and severity of the condition being treated and the patient. In addition, the modified serpin may suitably be administered by pulse infusion, e.g., with declining doses of the modified serpin. Preferably the dosing is given by injections, most preferably intravenous or subcutaneous injections, depending in part on whether the administration is brief or chronic.

Thus, in a particular embodiment, the pharmaceutical composition of the invention may be in a form suitable for parenteral administration, such as sterile solutions, suspensions or lyophilized products in the appropriate unit dosage form. Pharmaceutical compositions suitable for injectable use include sterile aqueous solutions (where water soluble) or dispersions and sterile powders for the extemporaneous preparation of sterile injectable solutions or dispersions. For intravenous administration, suitable carriers include physiological saline, bacteriostatic water, CremophorEM (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, a pharmaceutically acceptable polyol like glycerol, propylene glycol, liquid polyetheylene glycol, and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol or sodium chloride in the composition.

Prolonged absorption of the injectable compositions can be brought about by including in the composition an agent which delays absorption, for example, aluminium monostearate and gelatin.

Sterile injectable solutions can be prepared by incorporating the active compound (e.g. a modified serpin) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

In a particular embodiment, said pharmaceutical composition is administered via intravenous (IV) or subcutaneous (SC). Adequate excipients can be used, such as bulking agents, buffering agents or surfactants. The mentioned formulations will be prepared using standard methods for preparing parenterally administrable compositions as are well known in the art and described in more detail in various sources, including, for example, "Remington: The Science and Practice of Pharmacy" (Ed. Allen, L. V. 22nd edition, 2012, on the World-Wide Web at pharmpress.com).

It is especially advantageous to formulate the pharmaceutical compositions, namely parenteral compositions, in dosage unit form for ease administration and uniformity of dosage. Dosage unit form as used herein refers to physically discrete units suited as unitary dosages for the subject to be treated; each unit containing a predetermined quantity of active compound (antibody of the invention) calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Generally an effective administered amount of a modified serpin according to the invention will depend on the relative efficacy of the compound chosen, the severity of the disorder being treated and the weight of the sufferer. However, active compounds will typically be administered once or more times a day for example 1, 2, 3 or 4 times daily, with typical total daily doses in the range of from 0.001 to 1,000 mg/kg body weight/day, preferably about 0.01 to about 100 mg/kg body weight/day, most preferably from about 0.05 to 10 mg/kg body weight/day.

Aside from administration of a modified serpin according to the invention to the patient, the present application contemplates administration of a modified serpins by gene therapy. WO96/07321 relates the use of gene therapy to generate.

The pharmaceutical compositions can be included in a container, pack, or dispenser together with instructions for administration.

The antibodies and pharmaceutical compositions of this invention may be used with other drugs to provide a combination therapy. The other drugs may form part of the same composition, or be provided as a separate composition for administration at the same time or at different time.

In a sixth aspect, the invention pertains to a modified serpin molecule as described herein for use in the treatment or prevention of a bradykinin-mediated disease. In one embodiment, the modified serpin according to the invention may be used in the treatment or prevention of a bradykinin-mediated disease wherein the bradykinin-mediated disease is selected from the group consisting of non-histamine-dependent idiopathic angioedema, rheumatoid arthritis, Crohn's disease, ulcerative colitis, lupus, Alzheimer's disease, septic shock, burn injury, brain ischemia/reperfusion injury, cerebral edema, diabetic retinopathy, diabetic nephropathy, macular edema, vasculitis, arterial or venous thrombosis, thrombosis associated with ventricular assist devices or stents, heparin-induced thrombocytopenia with thrombosis, thromboembolic disease, and coronary heart disease with unstable angina pectoris, edema, eye disease, gout, intestinal bowel disease, oral mucositis, neuropathic pain, inflammatory pain, spinal stenosis degenerative spine disease, post-operative ileus, aortic aneurysm, osteoarthritis, hereditary angioedema, pulmonary embolism, stroke, head trauma or peri-tumor brain edema, sepsis, acute middle cerebral artery (MCA) ischemic event (stroke), restenosis (e.g., after angioplasty), systemic lupus erythematosis nephritis, an autoimmune disease, an inflammatory disease for example (chronic) auto-inflammatory urticaria, a cardiovascular disease, a neurological disease, a disease associated with protein misfolding, a disease associated with angiogenesis, hypertensive nephropathy and diabetic nephropathy, allergic and respiratory diseases (e.g. anaphylaxis, asthma, chronic obstructive pulmonary disease, acute respiratory distress syndrome, cystic fibrosis, persistent, rhinitis, urticarial and histamine dependent angioedema), tissue injuries (e.g. burn or chemical injury), and poli-trauma (e.g. car crashed and battle injuries).

In a seventh aspect, the invention relates to a gene therapy vector comprising a nucleotide sequence encoding a modified serpin according to the invention for use in the treatment or prevention of a bradykinin-mediated disease. Suitable gene therapy vectors are known per se to the skilled person and include e.g. the viral vectors derived from viruses such as including retrovirus, adenovirus, lentivirus, herpes simplex, vaccinia and adeno-associated virus, as well as non-viral vectors. Preferably, in the gene therapy vector the nucleotide sequence encoding a modified serpin is operably linked to a promoter that ensures expression of the coding sequence in hepatocytes. In one embodiment, the gene therapy vector comprising a nucleotide sequence encoding a modified serpin according is used in the treatment or prevention of a bradykinin-mediated disease wherein the bradykinin-mediated disease is selected from the group consisting of hereditary angioedema, idiopathic angioedema, rheumatoid arthritis, Crohn's disease, ulcerative colitis, lupus, Alzheimer's disease, septic shock, burn injury, brain ischemia/reperfusion injury, cerebral edema, diabetic retinopathy, diabetic nephropathy, macular edema, vasculitis, arterial or venous thrombosis, thrombosis associated with ventricular assist devices or stents, heparin-induced thrombocytopenia with thrombosis, thromboembolic disease, and coronary heart disease with unstable angina pectoris, edema, eye disease, gout, intestinal bowel disease, oral mucositis, neuropathic pain, inflammatory pain, spinal stenosis-degenerative spine disease, post-operative ileus, aortic aneurysm, osteoarthritis, hereditary angioedema, pulmonary embolism, stroke, head trauma or peri-tumor brain edema, sepsis, acute middle cerebral artery (MCA) ischemic event (stroke), restenosis (e.g., after angioplasty), systemic lupus erythematosis nephritis, an autoimmune disease, an inflammatory disease for example (chronic) auto-inflammatory urticaria, a cardiovascular disease, a neurological disease, a disease associated with protein misfolding, a disease associated with angiogenesis, hypertensive nephropathy and diabetic nephropathy, allergic and respiratory diseases (e.g. anaphylaxis, asthma, chronic obstructive pulmonary disease, acute respiratory distress syndrome, cystic fibrosis, persistent, rhinitis, urticarial and histamine dependent angioedema), tissue injuries (e.g. burn or chemical injury) and poli-trauma (e.g. car crashed and battle injuries).

It is to be understood that the application discloses all combinations of any of the above aspects and embodiments described above with each other, unless the context demands otherwise. Similarly, the application discloses all combinations of the preferred and/or optional features either singly or together with any of the other aspects, unless the context demands otherwise.

Modifications of the above embodiments, further embodiments and modifications thereof will be apparent to the skilled person on reading this disclosure, and as such these are within the scope of the present invention.

In this document and in its claims, the verb "to comprise" and its conjugations is used in its non-limiting sense to mean that items following the word are included, but items not specifically mentioned are not excluded. Other aspects and embodiments of the invention provide the aspects and embodiments described above with the term "comprising" replaced by the term "consisting of" and the aspects and embodiments described above with the term "comprising" replaced by the term "consisting essentially of".

In addition, reference to an element by the indefinite article "a" or "an" does not exclude the possibility that more than one of the element is present, unless the context clearly requires that there be one and only one of the elements. The indefinite article "a" or "an" thus usually means "at least one".

All documents and sequence database entries mentioned in this specification are incorporated herein by reference in their entirety for all purposes.

The present invention has been described above with reference to a number of exemplary embodiments as shown in the drawings. Modifications and alternative implementations of some parts or elements are possible, and are included in the scope of protection as defined in the appended claims.

EXAMPLES

Example 1

Modified Serpin Construction

Figure 1:
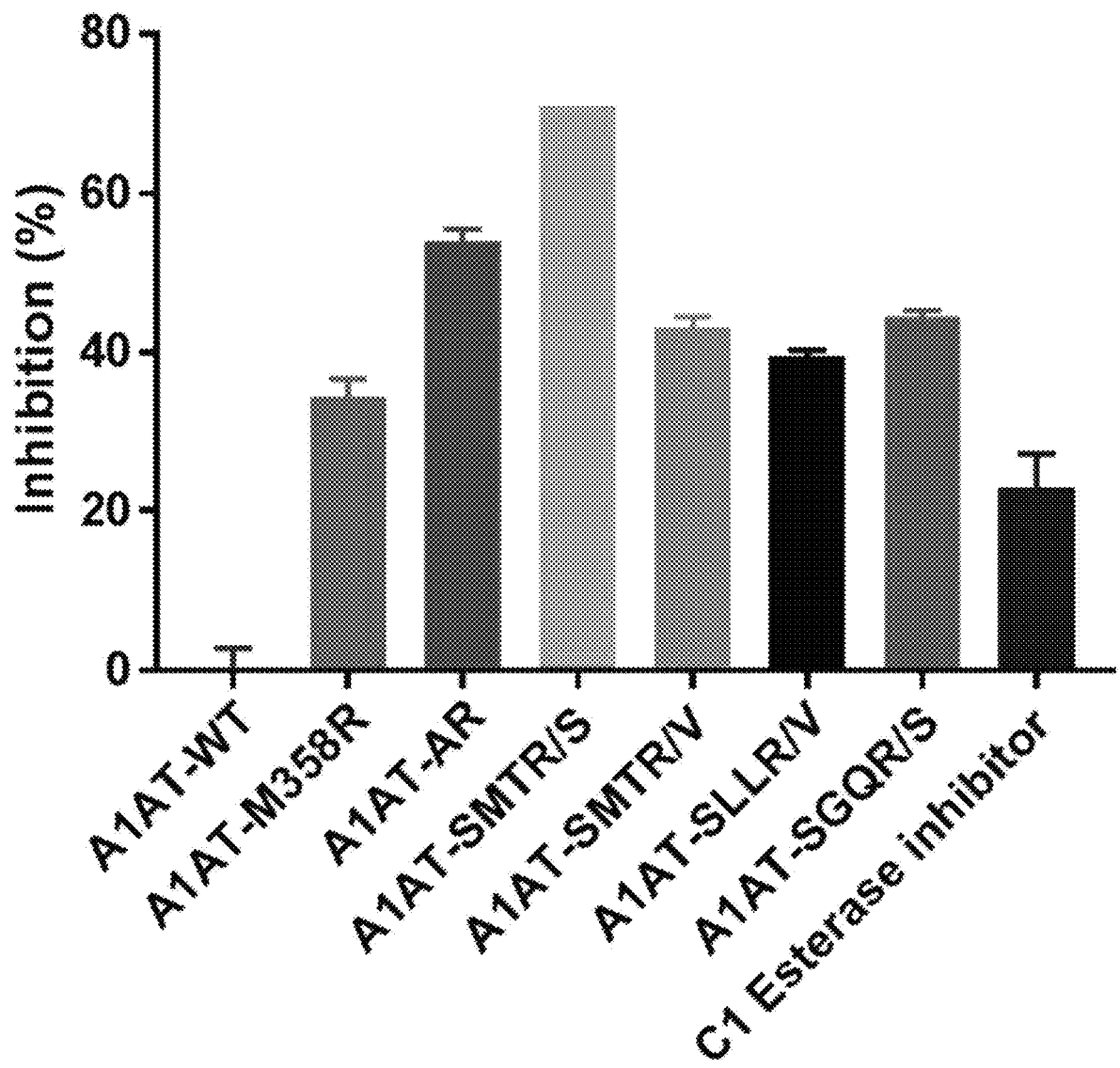
FIG. 1. Inhibition of plasma kallikrein-like activity in human plasma by various α1-Antitrypsin variants as indicated compared to inhibition by plasma-derived C1 esterase inhibitor. Plasma kallikrein-like activity is determined using the chromogenic substrate L2120.

The SERPINA1 cDNA sequence was obtained from the NCBI database (NM_001127707.1). The sequence coding for the signal peptide was discarded and replaced by a sequence coding for a Tobacco Etch Virus cleavage site. At the 5' side an EcoRI digestion site was added and at the 3' side and NotI digestion was added after the STOP codon of SERPINA1. Hereafter the $^{354}$AIPM$^{358}$ sequence (amino acid numbering without the signal peptide) was replaced with SMTR sequence (Codon sequence was grafted from wild type F12 NCBI: NM_000505.3). The construct was obtained from IDT (Integrated DNA Technologies, Leuven, Belgium)) as a custom gene construct. The custom gene construct was propagated in top E. coli TOP10 and selected by ampicillin resistance. Obtained plasmid DNA was digested by EcoRI and NotI. The resulting insert (1223 bp) was separated on and isolated from agarose gel and ligated into a modified pcDNA6 expression vector (pSM2) (De Maat et al, 2016 Clin Immunol November; 30; 138(5):1414-23)). pSM2 encodes for a N-terminal murine IgK secretion signal and a double STREP isolation tag where after the SerpinA1 construct is ligated.

For the construction of the wild type SERPINA1 or the other mutants the C-terminal part of the SERPINA1 sequence was replaced via BstelI-NotI digestion. The new constructs were ordered from IDT as gene block and ligated in to the digested SERPINA1-$^{354}$SMTR$^{358}$-pSM2 backbone.

Example 2

α1-Antitrypsin Expression

The SERPINA1-pSM2 constructs were transfected into HEK293 FreeStyle™ cells using 239Fectin as instructed by the manufacturer (ThermoFisher). After 4 days of protein production, the cells were spun down at 2000xg for 5 minutes. Hereafter the supernatant was collected and stored at −20° C. until further use.

Example 3

Enzyme Inhibition by α1-Antitrypsin Variants

10 μl of supernatant containing the α1-Antitrypsin variants was incubated with 10 μl of enzyme and 20 μl of buffer (0.2% w/v bovine serum albumin in Hepes buffered saline: 10 mM HEPES, 150 mM NaCl, pH=7.4). After a 5 minute incubation the substrate was added and substrate conversion was monitored according to substrate specifications. Inhibition percentage was determined within the linear part of the substrate conversion, where substrate conversion without the presence of any α1-AT variant was set as 0% inhibition.

Enzymes
Human αFXIIa (final concentration: 2 μg/mL)
Human βFXIIa (final concentration: 0.7 μg/mL)
Plasma kallikrein (final concentration: 2 μg/mL)
Thrombin (final concentration: 2 U/mL)
Plasmin (final concentration: 2 μg/mL)
Activated protein C (final concentration: 2 μg/mL)
Substrates

| Enzyme | Substrate | Final Concentration | Method | Wavelength |
|---|---|---|---|---|
| FXIIa | L2120 | 0.5 mM | Absorption | 405 nm |
| PK | L2120 | 0.5 mM | Absorption | 405 nm |
| Thrombin | I1140 | 2 mM | Fluorescence | Ext: 380 Em: 460 |
| Plasmin | I1390 | 0.5 mM | Fluorescence | Ext: 380 Em: 460 |
| APC | S2366 | 0.5 mM | Absorption | 405 nm |

The following substrates where used:

L2120 (Bachem, Cat #L-2120.0100), H-D-Pro-Phe-Arg-pNA2 HCl; a chromogenic substrate for the determination of plasma kallikrein-like activity used as described in de Maat et al. (2016 Clin Immunol November; 30; 138(5):1414-23).

I1140 (Bachem, Cat #I-1140.0100), Benzyloxycarbonyl-Gly-Gly-Arg-7-amido-4-methylcoumarin·HCl; can used as substrate in a direct fluorometric assay of urokinase and tissue-type plasminogen activator as well as for assaying trypsin and thrombin used as described in Chowdary et al. (2015, Br. J. Haematol., 168: 719).

I1390 (Bachem, Cat #I-1390.0050), H-D-Val-Leu-Lys-7-amido-4-methylcoumarin acetate salt; a sensitive, highly specific fluorescent substrate for plasmin used as described in de Maat et al. (2016 Clin Immunol November; 30; 138(5):1414-23).

S2366 (Chromogenix; Cat #S2366), pyroGlu-Pro-Arg-pNAHCl; Chromogenic substrate for activated protein C and factor XIa as described in Hubbard et al. (1988, Thromb Haemost; 59, 464-467).

Results of the inhibition of the relevant proteases by the various α1AT variants are provide in Table 1.

TABLE 1

Overview of the percentage inhibition of the relevant proteases by the various α1-Antitrypsin variants of the invention.

| α1-AT variants | Amino acid residues in RCL positions P8 and P4-P4' | | | | | | | | | SEQ ID NO. | αFXIIa | | βFXIIa | | Plasma Kallikrein | | Plasmin | | Thrombin | | APC | |
|---|---|---|---|---|---|---|---|---|---|---|---|---|---|---|---|---|---|---|---|---|---|---|
| | P8 | P4 | P3 | P2 | P1 | P1' | P2' | P3' | P4' | | Average | St Dev | Average | St Dev | Average | St Dev | Average | St Dev | Average | St Dev | Average | St Dev |
| WT | M | A | I | P | M | S | I | P | P | 335 | 0.0 | 0.0 | 0.0 | 0.0 | 0.0 | 0.0 | 0.0 | 0.0 | 0.0 | 0.0 | 0.0 | 0.0 |
| M358R | M | A | I | P | R | S | I | P | P | 336 | 94.0 | 2.8 | 90.0 | — | 91.5 | 3.5 | 100.0 | 0.0 | 100.0 | 0.0 | 94.0 | 4.2 |
| 357AR358 | M | A | I | A | R | S | I | P | P | 337 | 62.5 | 10.6 | 49.0 | — | 98.0 | 0.0 | 99.0 | 1.4 | 97.5 | 0.7 | 66.5 | 17.7 |
| SMTR | M | S | M | T | R | S | I | P | P | 338 | 88.5 | 9.2 | 85.0 | — | 98.5 | 0.7 | 94.0 | 1.4 | 10.5 | 0.7 | 75.0 | 18.4 |
| SMTRox* | V | S | M | T | R | S | I | P | P | 339 | 92.5 | 3.5 | 89.2 | 4.8 | 98.7 | 0.8 | 94.5 | 1.4 | 10.3 | 1.5 | 76.5 | 8.4 |
| SMTRox*-VVGG | V | S | M | T | R | V | V | G | G | 340 | NT | — | 29.0 | — | 47.0 | — | 8.0 | — | 1.0 | — | 0.0 | — |
| SMTRox*-GVGG | V | S | M | T | R | G | V | G | G | 341 | NT | — | 9.0 | — | 39.0 | — | 20.0 | — | 3.0 | — | 3.0 | — |
| SGQRox* | V | S | G | Q | R | S | I | P | P | 342 | 4.5 | 2.1 | 4.0 | — | 88.0 | 1.4 | 5.0 | 7.1 | 14.5 | 0.7 | 6.5 | 0.7 |
| SVTRox* | V | S | V | T | R | S | I | P | P | 343 | 47.0 | — | 39.0 | — | 99.0 | — | 97.0 | — | 7.0 | — | 49.0 | — |
| SATRox* | V | S | A | T | R | S | I | P | P | 344 | 17.0 | — | 15.0 | — | 94.0 | — | 0.0 | — | 3.0 | — | 10.0 | — |
| SFNRox* | V | S | F | N | R | S | I | P | P | 345 | 5.0 | — | 3.0 | — | 94.0 | — | 3.0 | — | 7.0 | — | 5.0 | — |
| SWKKox* | V | S | W | K | K | S | I | P | P | 346 | NT | — | 5.0 | — | 94.0 | — | 47.0 | — | 0.0 | — | 0.0 | — |
| SEARox* | V | S | E | A | R | S | I | P | P | 347 | NT | — | 6.0 | — | 92.0 | — | 13.0 | — | 0.0 | — | 3.0 | — |
| SLLRox* | V | S | L | L | R | S | I | P | P | 348 | NT | — | 41.0 | 3.5 | 97.7 | 1.5 | 94.7 | 1.5 | 62.3 | 8.1 | 9.7 | 5.0 |
| SLLRox*-V | V | S | L | L | R | V | I | P | P | 349 | NT | — | 47.0 | 8.5 | 97.5 | 0.7 | 68.0 | 1.4 | 4.5 | 4.9 | 3.0 | 2.8 |
| SLLRox*-I | V | S | L | L | R | I | I | P | P | 350 | NT | — | 40.3 | 8.5 | 91.3 | 5.0 | 66.7 | 2.9 | 3.7 | 3.2 | 2.3 | 2.1 |
| SVVKox* | V | S | V | V | K | S | I | P | P | 351 | 4.0 | — | 2.0 | — | 55.0 | — | 95.0 | — | 6.0 | — | 8.0 | — |

TABLE 1-continued

Overview of the percentage inhibition of the relevant proteases by the various α1-Antitrypsin variants of the invention.

| α1-AT variants | Amino acid residues in RCL positions P8 and P4-P4' | | | | | | | | | SEQ ID NO. | αFXIIa | | βFXIIa | | Plasma Kallikrein | | Plasmin | | Thrombin | | APC | |
|---|---|---|---|---|---|---|---|---|---|---|---|---|---|---|---|---|---|---|---|---|---|---|
| | P8 | P4 | P3 | P2 | P1 | P1' | P2' | P3' | P4' | | Average | St Dev | Average | St Dev | Average | St Dev | Average | St Dev | Average | St Dev | Average | St Dev |
| SDYKox* | V | S | D | Y | K | S | I | P | P | 352 | NT | — | 7.0 | — | 50.0 | — | 7.0 | — | 0.0 | — | 1.0 | — |
| SVRKox* | V | S | V | R | K | S | I | P | P | 353 | 2.0 | — | 0.0 | — | 91.0 | — | 97.0 | — | 1.0 | — | 4.0 | — |
| SPRRox* | V | S | P | R | R | S | I | P | P | 354 | 1.0 | — | 2.0 | — | 97.0 | — | 19.0 | — | 0.0 | — | 1.0 | — |
| SMDRox* | V | S | M | D | R | S | I | P | P | 355 | NT | — | 4.0 | — | 87.0 | — | 20.0 | — | 0.0 | — | 0.0 | — |
| SLGRox* | V | S | L | G | R | S | I | P | P | 356 | NT | — | 17.3 | 2.9 | 95.5 | 0.6 | 5.3 | 2.4 | 9.5 | 2.1 | 1.0 | 1.2 |
| SKGRox* | V | S | K | G | R | S | I | P | P | 357 | NT | — | 22.0 | — | 97.0 | — | 37.0 | — | 7.0 | — | 0.0 | — |
| SGNRox* | V | S | G | W | R | S | I | P | P | 358 | NT | — | 5.2 | 1.3 | 71.6 | 1.9 | 1.0 | 2.2 | 0.0 | 0.0 | 1.0 | 1.0 |
| SYARox* | V | S | Y | A | R | S | I | P | P | 359 | NT | — | 20.0 | — | 97.0 | — | 0.0 | — | 62.0 | — | 7.0 | — |
| SMHRox* | V | S | M | H | R | S | I | P | P | 360 | NT | — | 18.3 | 4.0 | 96.3 | 0.6 | 73.0 | 6.1 | 10.0 | 1.0 | 34.0 | 5.6 |
| SNSRox* | V | S | N | S | R | S | I | P | P | 361 | NT | — | 20.0 | — | 97.0 | — | 0.0 | — | 62.0 | — | 7.0 | — |

*"ox" indicates that methionine (M) residues 351 (P8) is replaced with a serine (S) residues to prevent oxidative inactivation of α1AT

Example 4

Figure 2:
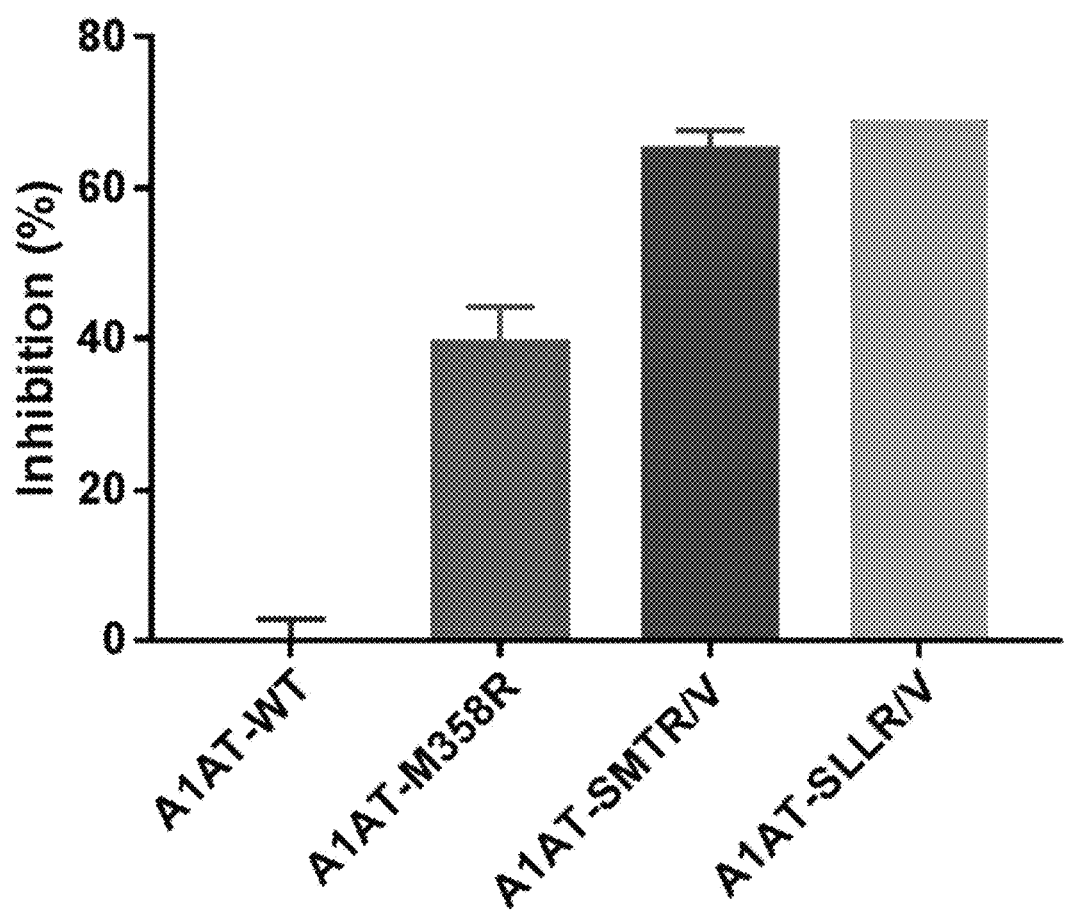
FIG. 2. Inhibition of plasma kallikrein-like activity in mouse plasma by various α1-Antitrypsin variants as indicated. Plasma kallikrein-like activity is determined using the chromogenic substrate L2120.

Inhibition in Human and in Mouse Plasma

α1-Antitrypsin variants as indicated in FIGS. 1 and 2 were tested for their ability to inhibit plasma kallikrein-like activity as determined with the chromogenic substrate L2120 in respectively human and mouse plasma. In human plasma the inhibition by α1-Antitrypsin variants was also compared with that by plasma-derived C1 esterase inhibitor (Alpha Diagnostics; C1E15-N).

50 μl of human plasma (3.2% Citrate) was mixed with 20 μl α1-Antitrypsin variant (20 μg/mL final conc.) or C1 esterase inhibitor (40 μg/mL final conc.), 20 μl L2120 chromogenic PK substrate (0.5 mM final conc.) and 10 μl Kaolin (18.75 μg/mL final conc.). Inhibition of plasma kallikrein-like activity was determined as described in Example 3. Results are shown in FIG. 1.

20 μl of mouse plasma (3.2% Citrate) was mixed with 20 μl α1-Antitrypsin variant (100 μg/mL final conc.), 10 μl L2120 chromogenic PK substrate (0.5 mM final conc.) and 5 μl Kaolin (135 μg/mL final conc.). Inhibition of plasma kallikrein-like activity was determined as described in Example 3. Results are shown in FIG. 2.

Example 5

Enzyme Inhibition by α1-Antitrypsin P1 Prime-Variants

The amino acid of the P1 prime (P1') position was altered to every natural occurring amino acid. As a template sequence we used the α1-Antitrypsin-Pittsburgh sequence having the P4-P3-P2-P1/P1'-P2'-P3'-P4 sequence': AIPR/XIPP for the library, wherein X marks the P1' position in which the amino acid was varied.

α1-Antitrypsin variants were produced as described above in Example 2, except that supernatant was harvested after 5 days. Empty production vector was used as a negative control (No A1AT). Production of the α1-Antitrypsin variants was quantified by coomassie blue and supernatants were diluted in pSM2 media to equalize the concentrations of the different α1AT variants. Enzyme inhibition by the α1-Antitrypsin P1'-variants was tested as described in Example 3 above.

Figure 3:
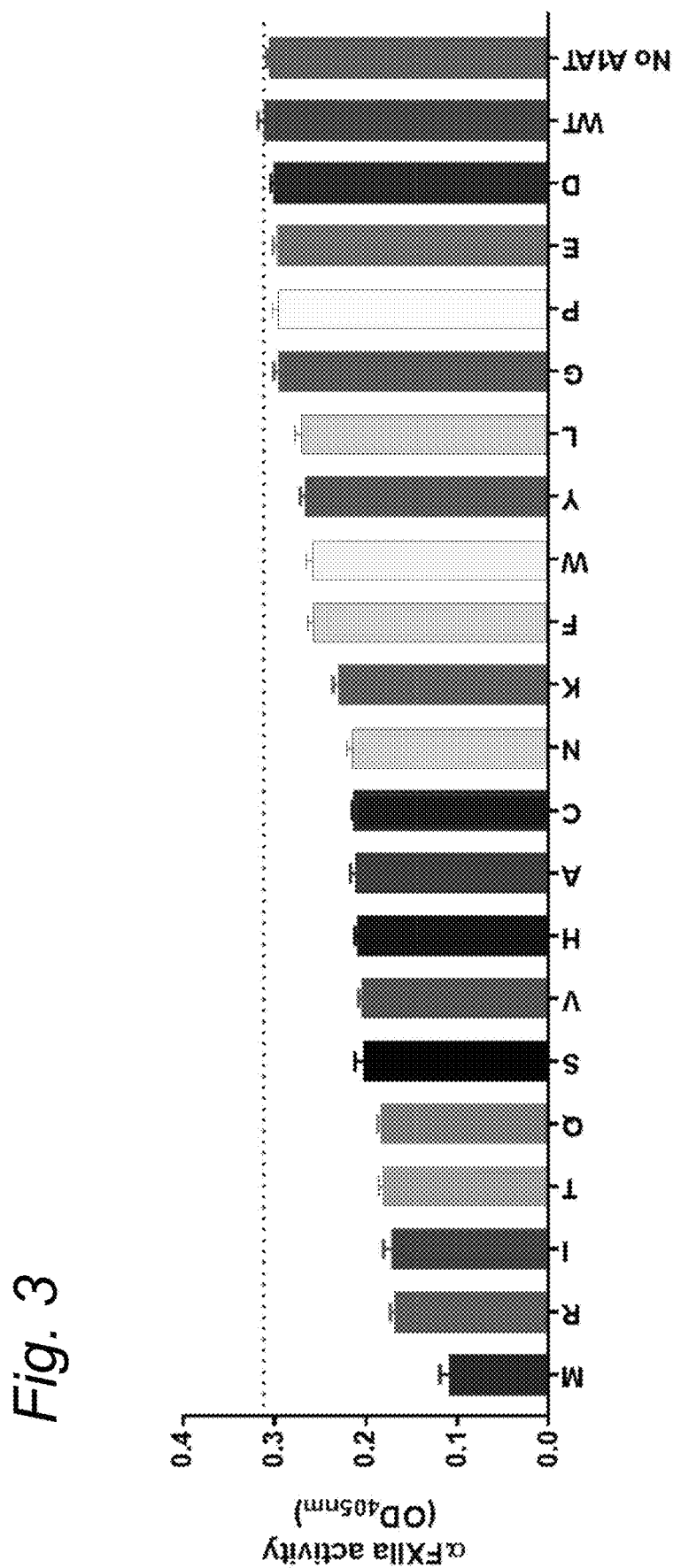
FIG. 3. Inhibition of Factor XIIa activity by α1-Antitrypsin Pittsburgh variants wherein the P1 prime (P1') position was altered to every natural occurring amino acid as indicated.
Figure 4:
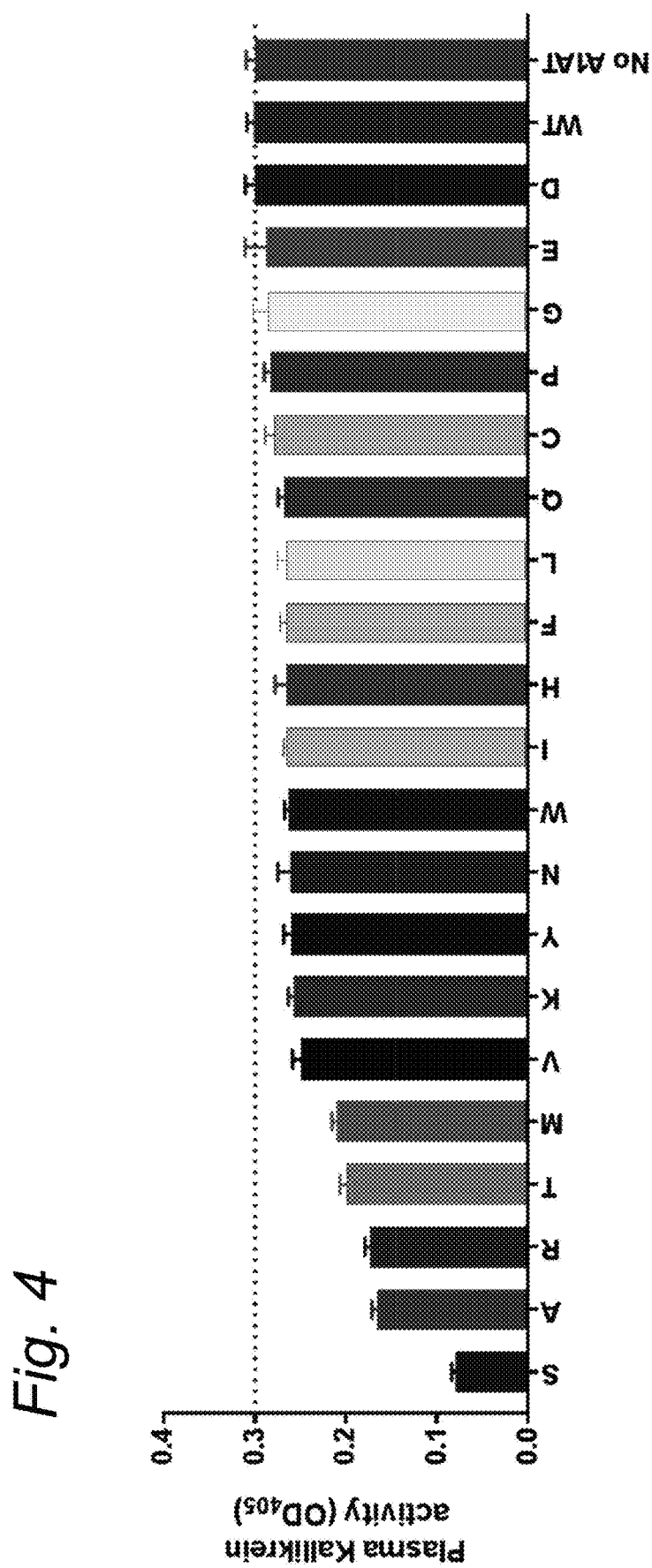
FIG. 4. Inhibition of plasma kallikrein activity by a1-Antitrypsin Pittsburgh variants wherein the P1 prime (P1') position was altered to every natural occurring amino acid as indicated.
Figure 5:
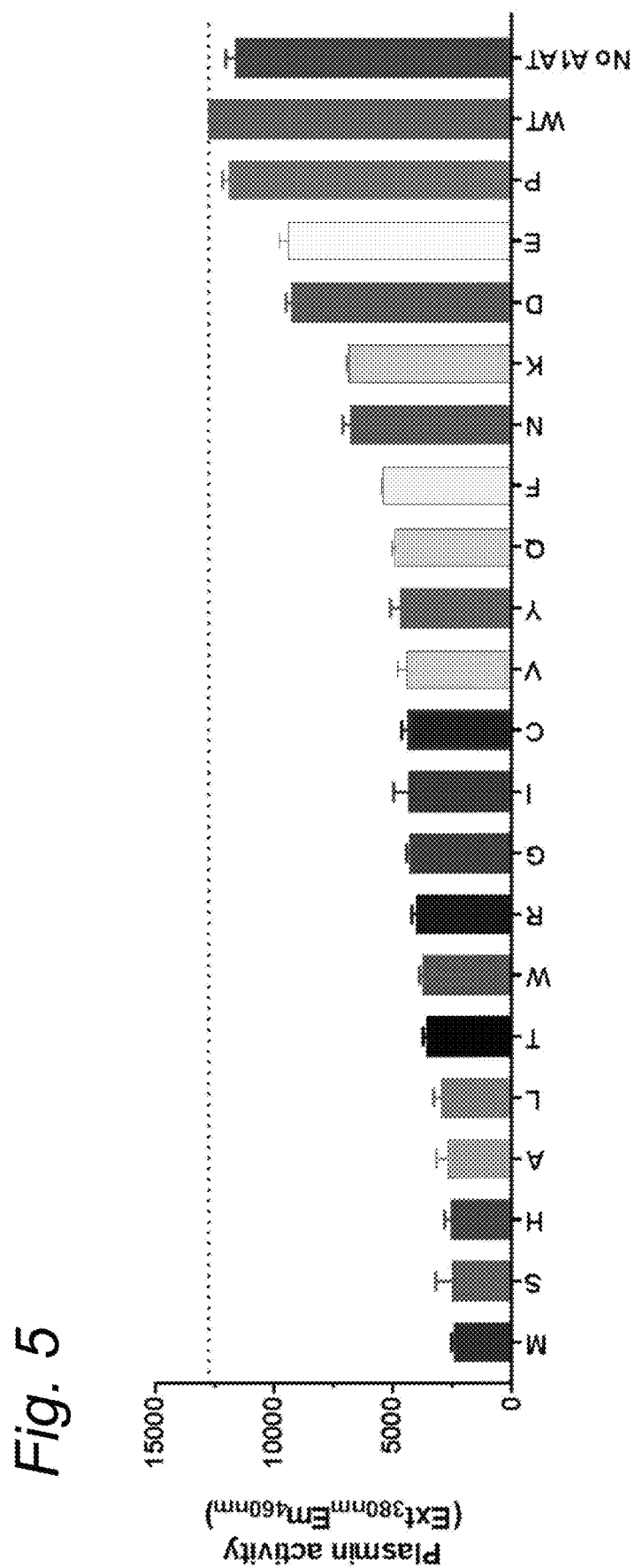
FIG. 5. Inhibition of plasmin activity by a1-Antitrypsin Pittsburgh variants wherein the P1 prime (P1') position was altered to every natural occurring amino acid as indicated.
Figure 6:
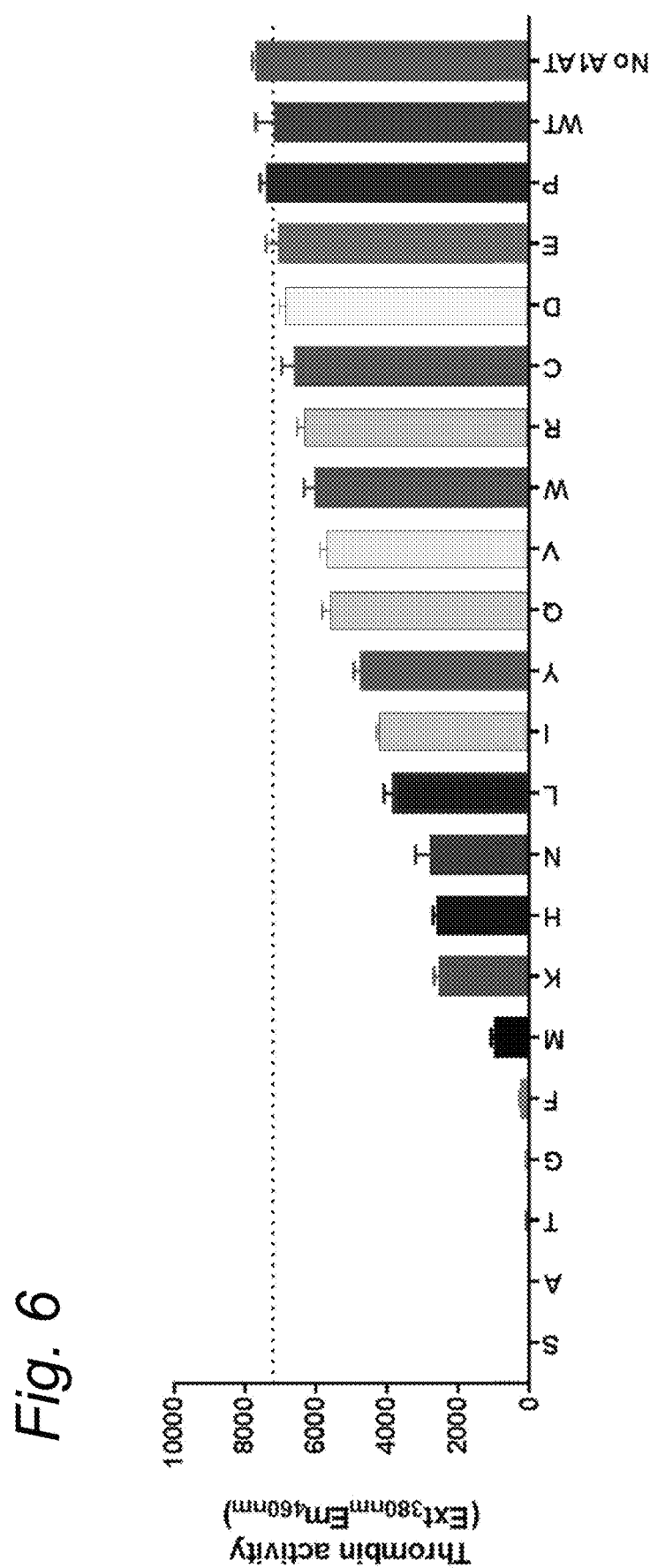
FIG. 6. Inhibition of thrombin activity by a1-Antitrypsin Pittsburgh variants wherein the P1 prime (P1') position was altered to every natural occurring amino acid as indicated.
Figure 7:
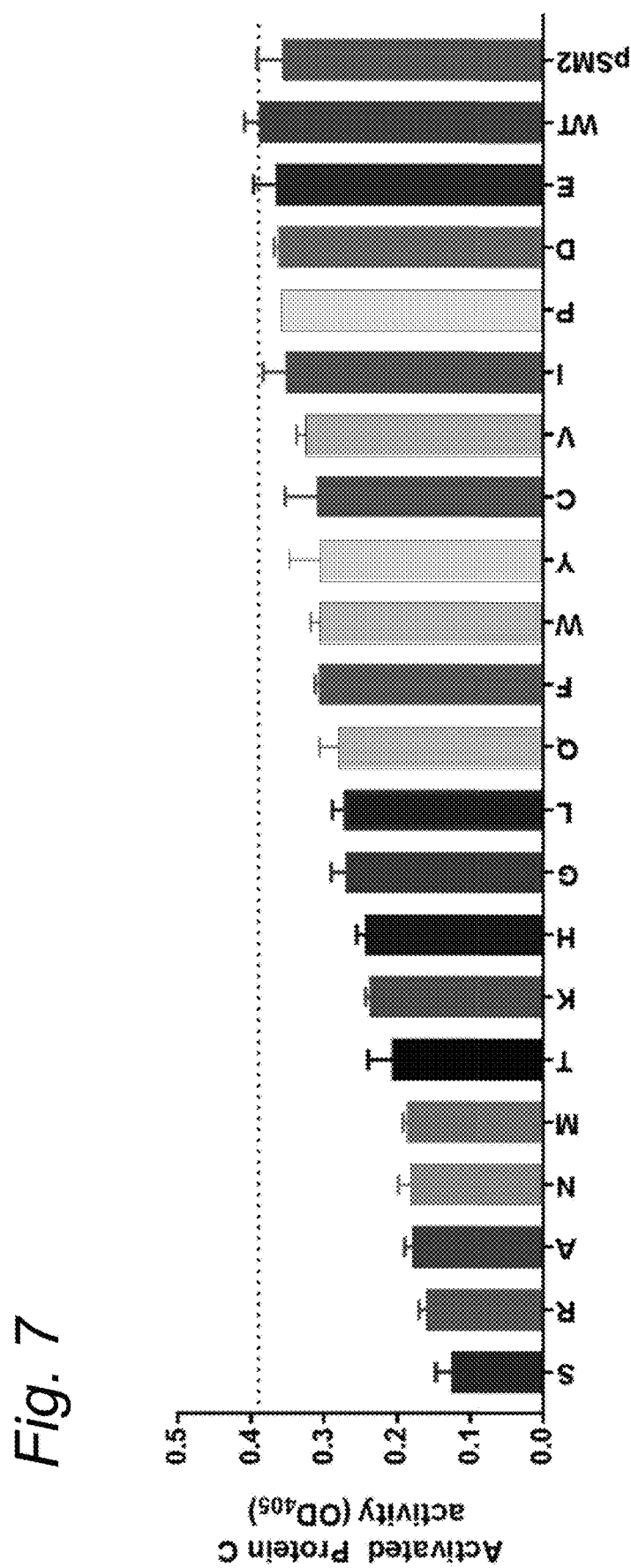
FIG. 7. Inhibition of activated protein C activity by a1-Antitrypsin Pittsburgh variants wherein the P1 prime (P1') position was altered to every natural occurring amino acid as indicated.

Results are shown in FIG. 3 for the inhibition of Factor XIIa, FIG. 4 for the inhibition of plasma kallikrein, FIG. 5 for the inhibition of plasmin, FIG. 6 for the inhibition of thrombin and FIG. 7 for the inhibition of activated protein C. Results indicate that A, M, R and T are preferred residues at the P1' position.

The invention claimed is:

1. A modified α1 antitrypsin comprising a reactive center loop (RCL), wherein the residues P4-P1 of the RCL are selected from the group consisting of SMTR (SEQ ID NO: 12), SEAR (SEQ ID NO: 18), SMDR (SEQ ID NO: 23), SLGR (SEQ ID NO: 24), SKGR (SEQ ID NO: 25) and SMHR (SEQ ID NO: 27), wherein the modified α1 antitrypsin demonstrates increased inhibition of plasma kallikrein (PK) as compared to the corresponding unmodified α1 antitrypsin, and wherein the modified α1-antitrypsin more strongly inhibits PK than the modified α1 antitrypsin inhibits either one of thrombin or APC.

2. The modified α1-antitrypsin of claim 1, further comprising a mutation in P1', wherein the P1' residue is selected from the group consisting of: Q, F, H, R, K, C, L, Y, N, I, D, W, E, V, M, A, T and P.

3. The modified α1-antitrypsin of claim 2, wherein the P1' residue is selected from the group consisting of: K, L, Y, I, D, E, A, T, M, R and V.

4. The modified α1-antitrypsin of claim 3, wherein the P1' residue is selected from the group consisting of: I and V.

5. The modified α1-antitrypsin of claim 1, wherein the P8 of residue of the RCL is V.

6. A method of treating a bradykinin-mediated disease, wherein the method comprises administering to a subject in need thereof an effective amount of modified serpin according to claim 1.

7. The method of claim 6, wherein the minimal amount of the serpin that inhibits PK activity by at least 50%, is an amount that inhibits thrombin activity by no more than 15%.

8. The method of claim 7, wherein the minimal amount of the serpin that inhibits PK activity by at least 50%, is an amount that inhibits at least one of:
a) plasmin by at least 15%;
b) an active form of FCII by at least 15%; and/or
c) APC by no more than 15%.

9. The method of claim 6, wherein the serpin further has a mutation whereby the P1' residue of the reactive center loop (RCL) is selected from the group consisting of:
Q, F, H, R, K, C, L, Y, N, I, D, W, E, V, M, A, T and P.

10. The method of claim 9, wherein the P1' residue is selected from the group consisting of K, L, Y, I, D, E, A, T, M, R and V.

11. The method of claim 9, wherein the P1' residue is selected from the group consisting of I and V.

12. The method of claim 6, wherein the bradykinin-mediated disease is selected from the group consisting of hereditary angioedema, idiopathic angioedema, rheumatoid arthritis, Crohn's disease, ulcerative colitis, lupus, Alzheimer's disease, septic shock, burn injury, brain ischemia/reperfusion injury, cerebral edema, diabetic retinopathy, diabetic nephropathy, macular edema, vasculitis, arterial or venous thrombosis, thrombosis associated with ventricular assist devices or stents, heparin-induced thrombocytopenia with thrombosis, thromboembolic disease, coronary heart disease with unstable angina pectoris, edema, eye disease, gout, intestinal bowel disease, oral mucositis, neuropathic pain, inflammatory pain, spinal stenosis-degenerative spine disease, post-operative ileus, aortic aneurysm, osteoarthritis, hereditary angioedema, pulmonary embolism, stroke, head trauma, peri-tumor brain edema, sepsis, acute middle cerebral artery (MCA) ischemic event, restenosis, systemic lupus erythematosis nephritis, an autoimmune disease, an inflammatory disease, a cardiovascular disease, a neurological disease, a disease associated with protein misfolding, a disease associated with angiogenesis, hypertensive nephropathy, diabetic nephropathy, allergic diseases, respiratory diseases, tissue injuries, and a poli-trauma.

13. The method of claim 12, wherein the restenosis is after angioplasty.

14. The method of claim 12, wherein the inflammatory disease is chronic auto-inflammatory urticaria.

15. The method of claim 12, wherein the respiratory disease is selected from the group consisting of anaphylaxis, asthma, chronic obstructive pulmonary disease, acute respiratory distress syndrome, cystic fibrosis, rhinitis, urticarial, and histamine dependent angioedema.

16. The method of claim 12, wherein the tissue injury is a burn or a chemical injury.

17. The method of claim 12, wherein the poli-trauma is a car crash injury or a battle injury.

* * * * *

```
                        SEQUENCE LISTING

<160> NUMBER OF SEQ ID NOS: 361

<210> SEQ ID NO 1
<211> LENGTH: 394
<212> TYPE: PRT
<213> ORGANISM: Homo sapiens

<400> SEQUENCE: 1

Glu Asp Pro Gln Gly Asp Ala Ala Gln Lys Thr Asp Thr Ser His His
1               5                   10                  15

Asp Gln Asp His Pro Thr Phe Asn Lys Ile Thr Pro Asn Leu Ala Glu
            20                  25                  30

Phe Ala Phe Ser Leu Tyr Arg Gln Leu Ala His Gln Ser Asn Ser Thr
        35                  40                  45

Asn Ile Phe Phe Ser Pro Val Ser Ile Ala Thr Ala Phe Ala Met Leu
    50                  55                  60

Ser Leu Gly Thr Lys Ala Asp Thr His Asp Glu Ile Leu Glu Gly Leu
```

```
                65                  70                  75                  80
Asn Phe Asn Leu Thr Glu Ile Pro Glu Ala Gln Ile His Glu Gly Phe
                    85                  90                  95

Gln Glu Leu Leu Arg Thr Leu Asn Gln Pro Asp Ser Gln Leu Gln Leu
                100                 105                 110

Thr Thr Gly Asn Gly Leu Phe Leu Ser Glu Gly Leu Lys Leu Val Asp
                115                 120                 125

Lys Phe Leu Glu Asp Val Lys Lys Leu Tyr His Ser Glu Ala Phe Thr
            130                 135                 140

Val Asn Phe Gly Asp Thr Glu Glu Ala Lys Lys Gln Ile Asn Asp Tyr
145                 150                 155                 160

Val Glu Lys Gly Thr Gln Gly Lys Ile Val Asp Leu Val Lys Glu Leu
                165                 170                 175

Asp Arg Asp Thr Val Phe Ala Leu Val Asn Tyr Ile Phe Phe Lys Gly
                180                 185                 190

Lys Trp Glu Arg Pro Phe Glu Val Lys Asp Thr Glu Glu Glu Asp Phe
                195                 200                 205

His Val Asp Gln Val Thr Thr Val Lys Val Pro Met Met Lys Arg Leu
            210                 215                 220

Gly Met Phe Asn Ile Gln His Cys Lys Lys Leu Ser Ser Trp Val Leu
225                 230                 235                 240

Leu Met Lys Tyr Leu Gly Asn Ala Thr Ala Ile Phe Phe Leu Pro Asp
                245                 250                 255

Glu Gly Lys Leu Gln His Leu Glu Asn Glu Leu Thr His Asp Ile Ile
                260                 265                 270

Thr Lys Phe Leu Glu Asn Glu Asp Arg Arg Ser Ala Ser Leu His Leu
            275                 280                 285

Pro Lys Leu Ser Ile Thr Gly Thr Tyr Asp Leu Lys Ser Val Leu Gly
        290                 295                 300

Gln Leu Gly Ile Thr Lys Val Phe Ser Asn Gly Ala Asp Leu Ser Gly
305                 310                 315                 320

Val Thr Glu Glu Ala Pro Leu Lys Leu Ser Lys Ala Val His Lys Ala
                325                 330                 335

Val Leu Thr Ile Asp Glu Lys Gly Thr Glu Ala Ala Gly Ala Met Phe
            340                 345                 350

Leu Glu Ala Ile Pro Met Ser Ile Pro Pro Glu Val Lys Phe Asn Lys
            355                 360                 365

Pro Phe Val Phe Leu Met Ile Glu Gln Asn Thr Lys Ser Pro Leu Phe
        370                 375                 380

Met Gly Lys Val Val Asn Pro Thr Gln Lys
385                 390

<210> SEQ ID NO 2
<211> LENGTH: 398
<212> TYPE: PRT
<213> ORGANISM: Homo sapiens

<400> SEQUENCE: 2

Asn Ser Pro Leu Asp Glu Glu Asn Leu Thr Gln Glu Asn Gln Asp Arg
1               5                   10                  15

Gly Thr His Val Asp Leu Gly Leu Ala Ser Ala Asn Val Asp Phe Ala
                20                  25                  30

Phe Ser Leu Tyr Lys Gln Leu Val Leu Lys Ala Pro Asp Lys Asn Val
            35                  40                  45
```

Ile Phe Ser Pro Leu Ser Ile Ser Thr Ala Leu Ala Phe Leu Ser Leu
    50                  55                  60

Gly Ala His Asn Thr Thr Leu Thr Glu Ile Leu Lys Gly Leu Lys Phe
65                  70                  75                  80

Asn Leu Thr Glu Thr Ser Glu Ala Glu Ile His Gln Ser Phe Gln His
                85                  90                  95

Leu Leu Arg Thr Leu Asn Gln Ser Ser Asp Glu Leu Gln Leu Ser Met
            100                 105                 110

Gly Asn Ala Met Phe Val Lys Glu Gln Leu Ser Leu Leu Asp Arg Phe
        115                 120                 125

Thr Glu Asp Ala Lys Arg Leu Tyr Gly Ser Glu Ala Phe Ala Thr Asp
    130                 135                 140

Phe Gln Asp Ser Ala Ala Ala Lys Lys Leu Ile Asn Asp Tyr Val Lys
145                 150                 155                 160

Asn Gly Thr Arg Gly Lys Ile Thr Asp Leu Ile Lys Asp Leu Asp Ser
                165                 170                 175

Gln Thr Met Met Val Leu Val Asn Tyr Ile Phe Phe Lys Ala Lys Trp
            180                 185                 190

Glu Met Pro Phe Asp Pro Gln Asp Thr His Gln Ser Arg Phe Tyr Leu
        195                 200                 205

Ser Lys Lys Lys Trp Val Met Val Pro Met Met Ser Leu His His Leu
    210                 215                 220

Thr Ile Pro Tyr Phe Arg Asp Glu Glu Leu Ser Cys Thr Val Val Glu
225                 230                 235                 240

Leu Lys Tyr Thr Gly Asn Ala Ser Ala Leu Phe Ile Leu Pro Asp Gln
                245                 250                 255

Asp Lys Met Glu Glu Val Glu Ala Met Leu Leu Pro Glu Thr Leu Lys
            260                 265                 270

Arg Trp Arg Asp Ser Leu Glu Phe Arg Glu Ile Gly Glu Leu Tyr Leu
        275                 280                 285

Pro Lys Phe Ser Ile Ser Arg Asp Tyr Asn Leu Asn Asp Ile Leu Leu
    290                 295                 300

Gln Leu Gly Ile Glu Glu Ala Phe Thr Ser Lys Ala Asp Leu Ser Gly
305                 310                 315                 320

Ile Thr Gly Ala Arg Asn Leu Ala Val Ser Gln Val Val His Lys Ala
                325                 330                 335

Val Leu Asp Val Phe Glu Glu Gly Thr Glu Ala Ser Ala Ala Thr Ala
            340                 345                 350

Val Lys Ile Thr Leu Leu Ser Ala Leu Val Glu Thr Arg Thr Ile Val
        355                 360                 365

Arg Phe Asn Arg Pro Phe Leu Met Ile Ile Val Pro Thr Asp Thr Gln
    370                 375                 380

Asn Ile Phe Phe Met Ser Lys Val Thr Asn Pro Lys Gln Ala
385                 390                 395

<210> SEQ ID NO 3
<211> LENGTH: 478
<212> TYPE: PRT
<213> ORGANISM: Homo sapiens

<400> SEQUENCE: 3

Asn Pro Asn Ala Thr Ser Ser Ser Gln Asp Pro Glu Ser Leu Gln
1               5                   10                  15

Asp Arg Gly Glu Gly Lys Val Ala Thr Thr Val Ile Ser Lys Met Leu
            20                  25                  30

-continued

```
Phe Val Glu Pro Ile Leu Glu Val Ser Ser Leu Pro Thr Thr Asn Ser
             35                  40                  45
Thr Thr Asn Ser Ala Thr Lys Ile Thr Ala Asn Thr Thr Asp Glu Pro
 50                  55                  60
Thr Thr Gln Pro Thr Thr Glu Pro Thr Thr Gln Pro Thr Ile Gln Pro
 65                  70                  75                  80
Thr Gln Pro Thr Thr Gln Leu Pro Thr Asp Ser Pro Thr Gln Pro Thr
                 85                  90                  95
Thr Gly Ser Phe Cys Pro Gly Pro Val Thr Leu Cys Ser Asp Leu Glu
                100                 105                 110
Ser His Ser Thr Glu Ala Val Leu Gly Asp Ala Leu Val Asp Phe Ser
                115                 120                 125
Leu Lys Leu Tyr His Ala Phe Ser Ala Met Lys Lys Val Glu Thr Asn
130                 135                 140
Met Ala Phe Ser Pro Phe Ser Ile Ala Ser Leu Leu Thr Gln Val Leu
145                 150                 155                 160
Leu Gly Ala Gly Glu Asn Thr Lys Thr Asn Leu Glu Ser Ile Leu Ser
                165                 170                 175
Tyr Pro Lys Asp Phe Thr Cys Val His Gln Ala Leu Lys Gly Phe Thr
                180                 185                 190
Thr Lys Gly Val Thr Ser Val Ser Gln Ile Phe His Ser Pro Asp Leu
                195                 200                 205
Ala Ile Arg Asp Thr Phe Val Asn Ala Ser Arg Thr Leu Tyr Ser Ser
                210                 215                 220
Ser Pro Arg Val Leu Ser Asn Asn Ser Asp Ala Asn Leu Glu Leu Ile
225                 230                 235                 240
Asn Thr Trp Val Ala Lys Asn Thr Asn Asn Lys Ile Ser Arg Leu Leu
                245                 250                 255
Asp Ser Leu Pro Ser Asp Thr Arg Leu Val Leu Leu Asn Ala Ile Tyr
                260                 265                 270
Leu Ser Ala Lys Trp Lys Thr Thr Phe Asp Pro Lys Lys Thr Arg Met
                275                 280                 285
Glu Pro Phe His Phe Lys Asn Ser Val Ile Lys Val Pro Met Met Asn
                290                 295                 300
Ser Lys Lys Tyr Pro Val Ala His Phe Ile Asp Gln Thr Leu Lys Ala
305                 310                 315                 320
Lys Val Gly Gln Leu Gln Leu Ser His Asn Leu Ser Leu Val Ile Leu
                325                 330                 335
Val Pro Gln Asn Leu Lys His Arg Leu Glu Asp Met Glu Gln Ala Leu
                340                 345                 350
Ser Pro Ser Val Phe Lys Ala Ile Met Glu Lys Leu Glu Met Ser Lys
                355                 360                 365
Phe Gln Pro Thr Leu Leu Thr Leu Pro Arg Ile Lys Val Thr Thr Ser
370                 375                 380
Gln Asp Met Leu Ser Ile Met Glu Lys Leu Glu Phe Phe Asp Phe Ser
385                 390                 395                 400
Tyr Asp Leu Asn Leu Cys Gly Leu Thr Glu Asp Pro Asp Leu Gln Val
                405                 410                 415
Ser Ala Met Gln His Gln Thr Val Leu Glu Leu Thr Glu Thr Gly Val
                420                 425                 430
Glu Ala Ala Ala Ala Ser Ala Ile Ser Val Ala Arg Thr Leu Leu Val
                435                 440                 445
```

```
Phe Glu Val Gln Gln Pro Phe Leu Phe Val Leu Trp Asp Gln Gln His
            450                 455                 460
Lys Phe Pro Val Phe Met Gly Arg Val Tyr Asp Pro Arg Ala
465                 470                 475

<210> SEQ ID NO 4
<211> LENGTH: 464
<212> TYPE: PRT
<213> ORGANISM: Homo sapiens

<400> SEQUENCE: 4

Met Glu Pro Leu Gly Arg Gln Leu Thr Ser Gly Pro Asn Gln Glu Gln
1               5                   10                  15

Val Ser Pro Leu Thr Leu Leu Lys Leu Gly Asn Gln Glu Pro Gly Gly
            20                  25                  30

Gln Thr Ala Leu Lys Ser Pro Gly Val Cys Ser Arg Asp Pro Thr
        35                  40                  45

Pro Glu Gln Thr His Arg Leu Ala Arg Ala Met Met Ala Phe Thr Ala
50                  55                  60

Asp Leu Phe Ser Leu Val Ala Gln Thr Ser Thr Cys Pro Asn Leu Ile
65                  70                  75                  80

Leu Ser Pro Leu Ser Val Ala Leu Ala Leu Ser His Leu Ala Leu Gly
                85                  90                  95

Ala Gln Asn His Thr Leu Gln Arg Leu Gln Gln Val Leu His Ala Gly
            100                 105                 110

Ser Gly Pro Cys Leu Pro His Leu Leu Ser Arg Leu Cys Gln Asp Leu
        115                 120                 125

Gly Pro Gly Ala Phe Arg Leu Ala Ala Arg Met Tyr Leu Gln Lys Gly
130                 135                 140

Phe Pro Ile Lys Glu Asp Phe Leu Glu Gln Ser Glu Gln Leu Phe Gly
145                 150                 155                 160

Ala Lys Pro Val Ser Leu Thr Gly Lys Gln Glu Asp Asp Leu Ala Asn
                165                 170                 175

Ile Asn Gln Trp Val Lys Glu Ala Thr Glu Gly Lys Ile Gln Glu Phe
            180                 185                 190

Leu Ser Gly Leu Pro Glu Asp Thr Val Leu Leu Leu Asn Ala Ile
        195                 200                 205

His Phe Gln Gly Phe Trp Arg Asn Lys Phe Asp Pro Ser Leu Thr Gln
210                 215                 220

Arg Asp Ser Phe His Leu Asp Glu Gln Phe Thr Val Pro Val Glu Met
225                 230                 235                 240

Met Gln Ala Arg Thr Tyr Pro Leu Arg Trp Phe Leu Leu Glu Gln Pro
                245                 250                 255

Glu Ile Gln Val Ala His Phe Pro Phe Lys Asn Asn Met Ser Phe Val
            260                 265                 270

Val Leu Val Pro Thr His Phe Glu Trp Asn Val Ser Gln Val Leu Ala
        275                 280                 285

Asn Leu Ser Trp Asp Thr Leu His Pro Pro Leu Val Trp Glu Arg Pro
290                 295                 300

Thr Lys Val Arg Leu Pro Lys Leu Tyr Leu Lys His Gln Met Asp Leu
305                 310                 315                 320

Val Ala Thr Leu Ser Gln Leu Gly Leu Gln Glu Leu Phe Gln Ala Pro
                325                 330                 335

Asp Leu Arg Gly Ile Ser Glu Gln Ser Leu Val Val Ser Gly Val Gln
            340                 345                 350
```

```
His Gln Ser Thr Leu Glu Leu Ser Glu Val Gly Val Glu Ala Ala
        355                 360                 365

Ala Thr Ser Ile Ala Met Ser Arg Met Ser Leu Ser Ser Phe Ser Val
370                 375                 380

Asn Arg Pro Phe Leu Phe Ile Phe Glu Asp Thr Thr Gly Leu Pro
385                 390                 395                 400

Leu Phe Val Gly Ser Val Arg Asn Pro Asn Pro Ser Ala Pro Arg Glu
                405                 410                 415

Leu Lys Glu Gln Gln Asp Ser Pro Gly Asn Lys Asp Phe Leu Gln Ser
                420                 425                 430

Leu Lys Gly Phe Pro Arg Gly Asp Lys Leu Phe Gly Pro Asp Leu Lys
                435                 440                 445

Leu Val Pro Pro Met Glu Glu Asp Tyr Pro Gln Phe Gly Ser Pro Lys
                450                 455                 460
```

<210> SEQ ID NO 5
<211> LENGTH: 432
<212> TYPE: PRT
<213> ORGANISM: Homo sapiens

<400> SEQUENCE: 5

```
His Gly Ser Pro Val Asp Ile Cys Thr Ala Lys Pro Arg Asp Ile Pro
1               5                   10                  15

Met Asn Pro Met Cys Ile Tyr Arg Ser Pro Glu Lys Lys Ala Thr Glu
                20                  25                  30

Asp Glu Gly Ser Glu Gln Lys Ile Pro Glu Ala Thr Asn Arg Arg Val
            35                  40                  45

Trp Glu Leu Ser Lys Ala Asn Ser Arg Phe Ala Thr Thr Phe Tyr Gln
    50                  55                  60

His Leu Ala Asp Ser Lys Asn Asp Asn Asp Asn Ile Phe Leu Ser Pro
65                  70                  75                  80

Leu Ser Ile Ser Thr Ala Phe Ala Met Thr Lys Leu Gly Ala Cys Asn
                85                  90                  95

Asp Thr Leu Gln Gln Leu Met Glu Val Phe Lys Phe Asp Thr Ile Ser
                100                 105                 110

Glu Lys Thr Ser Asp Gln Ile His Phe Phe Phe Ala Lys Leu Asn Cys
            115                 120                 125

Arg Leu Tyr Arg Lys Ala Asn Lys Ser Ser Lys Leu Val Ser Ala Asn
130                 135                 140

Arg Leu Phe Gly Asp Lys Ser Leu Thr Phe Asn Glu Thr Tyr Gln Asp
145                 150                 155                 160

Ile Ser Glu Leu Val Tyr Gly Ala Lys Leu Gln Pro Leu Asp Phe Lys
                165                 170                 175

Glu Asn Ala Glu Gln Ser Arg Ala Ala Ile Asn Lys Trp Val Ser Asn
            180                 185                 190

Lys Thr Glu Gly Arg Ile Thr Asp Val Ile Pro Ser Glu Ala Ile Asn
        195                 200                 205

Glu Leu Thr Val Leu Val Leu Val Asn Thr Ile Tyr Phe Lys Gly Leu
    210                 215                 220

Trp Lys Ser Lys Phe Ser Pro Glu Asn Thr Arg Lys Glu Leu Phe Tyr
225                 230                 235                 240

Lys Ala Asp Gly Glu Ser Cys Ser Ala Ser Met Met Tyr Gln Glu Gly
                245                 250                 255

Lys Phe Arg Tyr Arg Arg Val Ala Glu Gly Thr Gln Val Leu Glu Leu
```

```
                260                 265                 270
Pro Phe Lys Gly Asp Asp Ile Thr Met Val Leu Ile Leu Pro Lys Pro
            275                 280                 285

Glu Lys Ser Leu Ala Lys Val Glu Lys Glu Leu Thr Pro Glu Val Leu
        290                 295                 300

Gln Glu Trp Leu Asp Glu Leu Glu Glu Met Met Leu Val Val His Met
305                 310                 315                 320

Pro Arg Phe Arg Ile Glu Asp Gly Phe Ser Leu Lys Glu Gln Leu Gln
                325                 330                 335

Asp Met Gly Leu Val Asp Leu Phe Ser Pro Glu Lys Ser Lys Leu Pro
            340                 345                 350

Gly Ile Val Ala Glu Gly Arg Asp Asp Leu Tyr Val Ser Asp Ala Phe
        355                 360                 365

His Lys Ala Phe Leu Glu Val Asn Glu Glu Gly Ser Glu Ala Ala Ala
    370                 375                 380

Ser Thr Ala Val Val Ile Ala Gly Arg Ser Leu Asn Pro Asn Arg Val
385                 390                 395                 400

Thr Phe Lys Ala Asn Arg Pro Phe Leu Val Phe Ile Arg Glu Val Pro
                405                 410                 415

Leu Asn Thr Ile Ile Phe Met Gly Arg Val Ala Asn Pro Cys Val Lys
            420                 425                 430

<210> SEQ ID NO 6
<211> LENGTH: 480
<212> TYPE: PRT
<213> ORGANISM: Homo sapiens

<400> SEQUENCE: 6

Gly Ser Lys Gly Pro Leu Asp Gln Leu Glu Lys Gly Gly Glu Thr Ala
1               5                   10                  15

Gln Ser Ala Asp Pro Gln Trp Glu Gln Leu Asn Asn Lys Asn Leu Ser
            20                  25                  30

Met Pro Leu Leu Pro Ala Asp Phe His Lys Glu Asn Thr Val Thr Asn
        35                  40                  45

Asp Trp Ile Pro Glu Gly Glu Asp Asp Tyr Leu Asp Leu Glu
    50                  55                  60

Lys Ile Phe Ser Glu Asp Asp Tyr Ile Asp Ile Val Asp Ser Leu
65              70                  75                  80

Ser Val Ser Pro Thr Asp Ser Asp Val Ser Ala Gly Asn Ile Leu Gln
                85                  90                  95

Leu Phe His Gly Lys Ser Arg Ile Gln Arg Leu Asn Ile Leu Asn Ala
            100                 105                 110

Lys Phe Ala Phe Asn Leu Tyr Arg Val Leu Lys Asp Gln Val Asn Thr
        115                 120                 125

Phe Asp Asn Ile Phe Ile Ala Pro Val Gly Ile Ser Thr Ala Met Gly
    130                 135                 140

Met Ile Ser Leu Gly Leu Lys Gly Glu Thr His Glu Gln Val His Ser
145                 150                 155                 160

Ile Leu His Phe Lys Asp Phe Val Asn Ala Ser Ser Lys Tyr Glu Ile
                165                 170                 175

Thr Thr Ile His Asn Leu Phe Arg Lys Leu Thr His Arg Leu Phe Arg
            180                 185                 190

Arg Asn Phe Gly Tyr Thr Leu Arg Ser Val Asn Asp Leu Tyr Ile Gln
        195                 200                 205
```

Lys Gln Phe Pro Ile Leu Leu Asp Phe Lys Thr Lys Val Arg Glu Tyr
                210                 215                 220

Tyr Phe Ala Glu Ala Gln Ile Ala Asp Phe Ser Asp Pro Ala Phe Ile
225                 230                 235                 240

Ser Lys Thr Asn Asn His Ile Met Lys Leu Thr Lys Gly Leu Ile Lys
                245                 250                 255

Asp Ala Leu Glu Asn Ile Asp Pro Ala Thr Gln Met Met Ile Leu Asn
                260                 265                 270

Cys Ile Tyr Phe Lys Gly Ser Trp Val Asn Lys Phe Pro Val Glu Met
                275                 280                 285

Thr His Asn His Asn Phe Arg Leu Asn Glu Arg Glu Val Val Lys Val
                290                 295                 300

Ser Met Met Gln Thr Lys Gly Asn Phe Leu Ala Ala Asn Asp Gln Glu
305                 310                 315                 320

Leu Asp Cys Asp Ile Leu Gln Leu Glu Tyr Val Gly Gly Ile Ser Met
                325                 330                 335

Leu Ile Val Val Pro His Lys Met Ser Gly Met Lys Thr Leu Glu Ala
                340                 345                 350

Gln Leu Thr Pro Arg Val Val Glu Arg Trp Gln Lys Ser Met Thr Asn
                355                 360                 365

Arg Thr Arg Glu Val Leu Leu Pro Lys Phe Lys Leu Glu Lys Asn Tyr
                370                 375                 380

Asn Leu Val Glu Ser Leu Lys Leu Met Gly Ile Arg Met Leu Phe Asp
385                 390                 395                 400

Lys Asn Gly Asn Met Ala Gly Ile Ser Asp Gln Arg Ile Ala Ile Asp
                405                 410                 415

Leu Phe Lys His Gln Gly Thr Ile Thr Val Asn Glu Glu Gly Thr Gln
                420                 425                 430

Ala Thr Thr Val Thr Thr Val Gly Phe Met Pro Leu Ser Thr Gln Val
                435                 440                 445

Arg Phe Thr Val Asp Arg Pro Phe Leu Phe Leu Ile Tyr Glu His Arg
                450                 455                 460

Thr Ser Cys Leu Leu Phe Met Gly Arg Val Ala Asn Pro Ser Arg Ser
465                 470                 475                 480

<210> SEQ ID NO 7
<211> LENGTH: 387
<212> TYPE: PRT
<213> ORGANISM: Homo sapiens

<400> SEQUENCE: 7

His Arg His His Pro Arg Glu Met Lys Lys Arg Val Glu Asp Leu His
1               5                   10                  15

Val Gly Ala Thr Val Ala Pro Ser Ser Arg Arg Asp Phe Thr Phe Asp
                20                  25                  30

Leu Tyr Arg Ala Leu Ala Ser Ala Ala Pro Ser Gln Ser Ile Phe Phe
                35                  40                  45

Ser Pro Val Ser Ile Ser Met Ser Leu Ala Met Leu Ser Leu Gly Ala
                50                  55                  60

Gly Ser Ser Thr Lys Met Gln Ile Leu Glu Gly Leu Gly Leu Asn Leu
65                  70                  75                  80

Gln Lys Ser Ser Glu Lys Glu Leu His Arg Gly Phe Gln Gln Leu Leu
                85                  90                  95

Gln Glu Leu Asn Gln Pro Arg Asp Gly Phe Gln Leu Ser Leu Gly Asn
                100                 105                 110

```
Ala Leu Phe Thr Asp Leu Val Val Asp Leu Gln Asp Thr Phe Val Ser
            115                 120                 125
Ala Met Lys Thr Leu Tyr Leu Ala Asp Thr Phe Pro Thr Asn Phe Arg
        130                 135                 140
Asp Ser Ala Gly Ala Met Lys Gln Ile Asn Asp Tyr Val Ala Lys Gln
145                 150                 155                 160
Thr Lys Gly Lys Ile Val Asp Leu Leu Lys Asn Leu Asp Ser Asn Ala
                165                 170                 175
Val Val Ile Met Val Asn Tyr Ile Phe Phe Lys Ala Lys Trp Glu Thr
            180                 185                 190
Ser Phe Asn His Lys Gly Thr Gln Glu Gln Asp Phe Tyr Val Thr Ser
        195                 200                 205
Glu Thr Val Val Arg Val Pro Met Met Ser Arg Glu Asp Gln Tyr His
    210                 215                 220
Tyr Leu Leu Asp Arg Asn Leu Ser Cys Arg Val Val Gly Val Pro Tyr
225                 230                 235                 240
Gln Gly Asn Ala Thr Ala Leu Phe Ile Leu Pro Ser Glu Gly Lys Met
                245                 250                 255
Gln Gln Val Glu Asn Gly Leu Ser Glu Lys Thr Leu Arg Lys Trp Leu
            260                 265                 270
Lys Met Phe Lys Lys Arg Gln Leu Glu Leu Tyr Leu Pro Lys Phe Ser
        275                 280                 285
Ile Glu Gly Ser Tyr Gln Leu Glu Lys Val Leu Pro Ser Leu Gly Ile
    290                 295                 300
Ser Asn Val Phe Thr Ser His Ala Asp Leu Ser Gly Ile Ser Asn His
305                 310                 315                 320
Ser Asn Ile Gln Val Ser Glu Met Val His Lys Ala Val Val Glu Val
                325                 330                 335
Asp Glu Ser Gly Thr Arg Ala Ala Ala Ala Thr Gly Thr Ile Phe Thr
            340                 345                 350
Phe Arg Ser Ala Arg Leu Asn Ser Gln Arg Leu Val Phe Asn Arg Pro
        355                 360                 365
Phe Leu Met Phe Ile Val Asp Asn Asn Ile Leu Phe Leu Gly Lys Val
    370                 375                 380
Asn Arg Pro
385

<210> SEQ ID NO 8
<211> LENGTH: 407
<212> TYPE: PRT
<213> ORGANISM: Homo sapiens

<400> SEQUENCE: 8

Gln Leu His Val Glu His Asp Gly Glu Ser Cys Ser Asn Ser Ser His
1               5                   10                  15
Gln Gln Ile Leu Glu Thr Gly Glu Gly Ser Pro Ser Leu Lys Ile Ala
            20                  25                  30
Pro Ala Asn Ala Asp Phe Ala Phe Arg Phe Tyr Tyr Leu Ile Ala Ser
        35                  40                  45
Glu Thr Pro Gly Lys Asn Ile Phe Phe Ser Pro Leu Ser Ile Ser Ala
    50                  55                  60
Ala Tyr Ala Met Leu Ser Leu Gly Ala Cys Ser His Ser Arg Ser Gln
65                  70                  75                  80
Ile Leu Glu Gly Leu Gly Phe Asn Leu Thr Glu Leu Ser Glu Ser Asp
```

```
                     85                  90                  95
Val His Arg Gly Phe Gln His Leu Leu His Thr Leu Asn Leu Pro Gly
            100                 105                 110

His Gly Leu Glu Thr Arg Val Gly Ser Ala Leu Phe Leu Ser His Asn
            115                 120                 125

Leu Lys Phe Leu Ala Lys Phe Leu Asn Asp Thr Met Ala Val Tyr Glu
    130                 135                 140

Ala Lys Leu Phe His Thr Asn Phe Tyr Asp Thr Val Gly Thr Ile Gln
145                 150                 155                 160

Leu Ile Asn Asp His Val Lys Lys Glu Thr Arg Gly Lys Ile Val Asp
                165                 170                 175

Leu Val Ser Glu Leu Lys Lys Asp Val Leu Met Val Leu Val Asn Tyr
            180                 185                 190

Ile Tyr Phe Lys Ala Leu Trp Glu Lys Pro Phe Ile Ser Ser Arg Thr
        195                 200                 205

Thr Pro Lys Asp Phe Tyr Val Asp Glu Asn Thr Thr Val Arg Val Pro
    210                 215                 220

Met Met Leu Gln Asp Gln Glu His His Trp Tyr Leu His Asp Arg Tyr
225                 230                 235                 240

Leu Pro Cys Ser Val Leu Arg Met Asp Tyr Lys Gly Asp Ala Thr Val
                245                 250                 255

Phe Phe Ile Leu Pro Asn Gln Gly Lys Met Arg Glu Ile Glu Glu Val
            260                 265                 270

Leu Thr Pro Glu Met Leu Met Arg Trp Asn Asn Leu Leu Arg Lys Arg
        275                 280                 285

Asn Phe Tyr Lys Lys Leu Glu Leu His Leu Pro Lys Phe Ser Ile Ser
290                 295                 300

Gly Ser Tyr Val Leu Asp Gln Ile Leu Pro Arg Leu Gly Phe Thr Asp
305                 310                 315                 320

Leu Phe Ser Lys Trp Ala Asp Leu Ser Gly Ile Thr Lys Gln Gln Lys
                325                 330                 335

Leu Glu Ala Ser Lys Ser Phe His Lys Ala Thr Leu Asp Val Asp Glu
            340                 345                 350

Ala Gly Thr Glu Ala Ala Ala Ala Thr Ser Phe Ala Ile Lys Phe Phe
        355                 360                 365

Ser Ala Gln Thr Asn Arg His Ile Leu Arg Phe Asn Arg Pro Phe Leu
    370                 375                 380

Val Val Ile Phe Ser Thr Ser Thr Gln Ser Val Leu Phe Leu Gly Lys
385                 390                 395                 400

Val Val Asp Pro Thr Lys Pro
                405

<210> SEQ ID NO 9
<211> LENGTH: 379
<212> TYPE: PRT
<213> ORGANISM: Homo sapiens

<400> SEQUENCE: 9

Val His His Pro Pro Ser Tyr Val Ala His Leu Ala Ser Asp Phe Gly
1               5                   10                  15

Val Arg Val Phe Gln Gln Val Ala Gln Ala Ser Lys Asp Arg Asn Val
            20                  25                  30

Val Phe Ser Pro Tyr Gly Val Ala Ser Val Leu Ala Met Leu Gln Leu
        35                  40                  45
```

```
Thr Thr Gly Gly Glu Thr Gln Gln Ile Gln Ala Ala Met Gly Phe
    50              55                  60

Lys Ile Asp Asp Lys Gly Met Ala Pro Ala Leu Arg His Leu Tyr Lys
 65              70                  75                      80

Glu Leu Met Gly Pro Trp Asn Lys Asp Glu Ile Ser Thr Thr Asp Ala
                 85                  90                  95

Ile Phe Val Gln Arg Asp Leu Lys Leu Val Gln Gly Phe Met Pro His
                100                 105                 110

Phe Phe Arg Leu Phe Arg Ser Thr Val Lys Gln Val Asp Phe Ser Glu
            115                 120                 125

Val Glu Arg Ala Arg Phe Ile Ile Asn Asp Trp Val Lys Thr His Thr
    130                 135                 140

Lys Gly Met Ile Ser Asn Leu Leu Gly Lys Gly Ala Val Asp Gln Leu
145                 150                 155                 160

Thr Arg Leu Val Leu Val Asn Ala Leu Tyr Phe Asn Gly Gln Trp Lys
                165                 170                 175

Thr Pro Phe Pro Asp Ser Ser Thr His Arg Arg Leu Phe His Lys Ser
            180                 185                 190

Asp Gly Ser Thr Val Ser Val Pro Met Met Ala Gln Thr Asn Lys Phe
            195                 200                 205

Asn Tyr Thr Glu Phe Thr Thr Pro Asp Gly His Tyr Tyr Asp Ile Leu
    210                 215                 220

Glu Leu Pro Tyr His Gly Asp Thr Leu Ser Met Phe Ile Ala Ala Pro
225                 230                 235                 240

Tyr Glu Lys Glu Val Pro Leu Ser Ala Leu Thr Asn Ile Leu Ser Ala
                245                 250                 255

Gln Leu Ile Ser His Trp Lys Gly Asn Met Thr Arg Leu Pro Arg Leu
            260                 265                 270

Leu Val Leu Pro Lys Phe Ser Leu Glu Thr Glu Val Asp Leu Arg Lys
            275                 280                 285

Pro Leu Glu Asn Leu Gly Met Thr Asp Met Phe Arg Gln Phe Gln Ala
    290                 295                 300

Asp Phe Thr Ser Leu Ser Asp Gln Glu Pro Leu His Val Ala Gln Ala
305                 310                 315                 320

Leu Gln Lys Val Lys Ile Glu Val Asn Glu Ser Gly Thr Val Ala Ser
                325                 330                 335

Ser Ser Thr Ala Val Ile Val Ser Ala Arg Met Ala Pro Glu Glu Ile
            340                 345                 350

Ile Met Asp Arg Pro Phe Leu Phe Val Val Arg His Asn Pro Thr Gly
    355                 360                 365

Thr Val Leu Phe Met Gly Gln Val Met Glu Pro
    370                 375

<210> SEQ ID NO 10
<211> LENGTH: 379
<212> TYPE: PRT
<213> ORGANISM: Homo sapiens

<400> SEQUENCE: 10

Ser His Phe Asn Pro Leu Ser Leu Glu Glu Leu Gly Ser Asn Thr Gly
 1               5                  10                  15

Ile Gln Val Phe Asn Gln Ile Val Lys Ser Arg Pro His Asp Asn Ile
                20                  25                  30

Val Ile Ser Pro His Gly Ile Ala Ser Val Leu Gly Met Leu Gln Leu
            35                  40                  45
```

```
Gly Ala Asp Gly Arg Thr Lys Lys Gln Leu Ala Met Val Met Arg Tyr
            50                  55                  60

Gly Val Asn Gly Val Gly Lys Ile Leu Lys Ile Asn Lys Ala Ile
 65                  70                  75                  80

Val Ser Lys Lys Asn Lys Asp Ile Val Thr Val Ala Asn Ala Val Phe
                    85                  90                  95

Val Lys Asn Ala Ser Glu Ile Glu Val Pro Phe Val Thr Arg Asn Lys
                100                 105                 110

Asp Val Phe Gln Cys Glu Val Arg Asn Val Asn Phe Glu Asp Pro Ala
            115                 120                 125

Ser Ala Cys Asp Ser Ile Asn Ala Trp Val Lys Asn Glu Thr Arg Asp
        130                 135                 140

Met Ile Asp Asn Leu Leu Ser Pro Asp Leu Ile Asp Gly Val Leu Thr
145                 150                 155                 160

Arg Leu Val Leu Val Asn Ala Val Tyr Phe Lys Gly Leu Trp Lys Ser
                165                 170                 175

Arg Phe Gln Pro Glu Asn Thr Lys Lys Arg Thr Phe Val Ala Ala Asp
            180                 185                 190

Gly Lys Ser Tyr Gln Val Pro Met Leu Ala Gln Leu Ser Val Phe Arg
        195                 200                 205

Cys Gly Ser Thr Ser Ala Pro Asn Asp Leu Trp Tyr Asn Phe Ile Glu
210                 215                 220

Leu Pro Tyr His Gly Glu Ser Ile Ser Met Leu Ile Ala Leu Pro Thr
225                 230                 235                 240

Glu Ser Ser Thr Pro Leu Ser Ala Ile Ile Pro His Ile Ser Thr Lys
                245                 250                 255

Thr Ile Asp Ser Trp Met Ser Ile Met Val Pro Lys Arg Val Gln Val
            260                 265                 270

Ile Leu Pro Lys Phe Thr Ala Val Ala Gln Thr Asp Leu Lys Glu Pro
        275                 280                 285

Leu Lys Val Leu Gly Ile Thr Asp Met Phe Asp Ser Ser Lys Ala Asn
290                 295                 300

Phe Ala Lys Ile Thr Thr Gly Ser Glu Asn Leu His Val Ser His Ile
305                 310                 315                 320

Leu Gln Lys Ala Lys Ile Glu Val Ser Glu Asp Gly Thr Lys Ala Ser
                325                 330                 335

Ala Ala Thr Thr Ala Ile Leu Ile Ala Arg Ser Ser Pro Pro Trp Phe
            340                 345                 350

Ile Val Asp Arg Pro Phe Leu Phe Phe Ile Arg His Asn Pro Thr Gly
        355                 360                 365

Ala Val Leu Phe Met Gly Gln Ile Asn Lys Pro
370                 375

<210> SEQ ID NO 11
<211> LENGTH: 423
<212> TYPE: PRT
<213> ORGANISM: Homo sapiens

<400> SEQUENCE: 11

Leu Ala Pro Ser Pro Gln Ser Pro Glu Thr Pro Ala Pro Gln Asn Gln
  1               5                  10                  15

Thr Ser Arg Val Val Gln Ala Pro Lys Glu Glu Glu Asp Glu Gln
                 20                  25                  30

Glu Ala Ser Glu Glu Lys Ala Ser Glu Glu Glu Lys Ala Trp Leu Met
```

```
                35                  40                  45
Ala Ser Arg Gln Gln Leu Ala Lys Glu Thr Ser Asn Phe Gly Phe Ser
 50                  55                  60

Leu Leu Arg Lys Ile Ser Met Arg His Asp Gly Asn Met Val Phe Ser
 65                  70                  75                  80

Pro Phe Gly Met Ser Leu Ala Met Thr Gly Leu Met Leu Gly Ala Thr
                 85                  90                  95

Gly Pro Thr Glu Thr Gln Ile Lys Arg Gly Leu His Leu Gln Ala Leu
                100                 105                 110

Lys Pro Thr Lys Pro Gly Leu Leu Pro Ser Leu Phe Lys Gly Leu Arg
            115                 120                 125

Glu Thr Leu Ser Arg Asn Leu Glu Leu Gly Leu Thr Gln Gly Ser Phe
130                 135                 140

Ala Phe Ile His Lys Asp Phe Asp Val Lys Thr Phe Phe Asn Leu
145                 150                 155                 160

Ser Lys Arg Tyr Phe Asp Thr Glu Cys Val Pro Met Asn Phe Arg Asn
                165                 170                 175

Ala Ser Gln Ala Lys Arg Leu Met Asn His Tyr Ile Asn Lys Glu Thr
            180                 185                 190

Arg Gly Lys Ile Pro Lys Leu Phe Asp Glu Ile Asn Pro Glu Thr Lys
        195                 200                 205

Leu Ile Leu Val Asp Tyr Ile Leu Phe Lys Gly Lys Trp Leu Thr Pro
210                 215                 220

Phe Asp Pro Val Phe Thr Glu Val Asp Thr Phe His Leu Asp Lys Tyr
225                 230                 235                 240

Lys Thr Ile Lys Val Pro Met Met Tyr Gly Ala Gly Lys Phe Ala Ser
                245                 250                 255

Thr Phe Asp Lys Asn Phe Arg Cys His Val Leu Lys Leu Pro Tyr Gln
            260                 265                 270

Gly Asn Ala Thr Met Leu Val Val Leu Met Glu Lys Met Gly Asp His
        275                 280                 285

Leu Ala Leu Glu Asp Tyr Leu Thr Thr Asp Leu Val Glu Thr Trp Leu
290                 295                 300

Arg Asn Met Lys Thr Arg Asn Met Glu Val Phe Pro Lys Phe Lys
305                 310                 315                 320

Leu Asp Gln Lys Tyr Glu Met His Glu Leu Leu Arg Gln Met Gly Ile
                325                 330                 335

Arg Arg Ile Phe Ser Pro Phe Ala Asp Leu Ser Glu Leu Ser Ala Thr
            340                 345                 350

Gly Arg Asn Leu Gln Val Ser Arg Val Leu Gln Arg Thr Val Ile Glu
        355                 360                 365

Val Asp Glu Arg Gly Thr Glu Ala Val Ala Gly Ile Leu Ser Glu Ile
370                 375                 380

Thr Ala Tyr Ser Met Pro Pro Val Ile Lys Val Asp Arg Pro Phe His
385                 390                 395                 400

Phe Met Ile Tyr Glu Glu Thr Ser Gly Met Leu Leu Phe Leu Gly Arg
                405                 410                 415

Val Val Asn Pro Thr Leu Leu
                420

<210> SEQ ID NO 12
<211> LENGTH: 4
<212> TYPE: PRT
<213> ORGANISM: Artificial
```

```
<220> FEATURE:
<223> OTHER INFORMATION: peptide

<400> SEQUENCE: 12

Ser Met Thr Arg
1

<210> SEQ ID NO 13
<211> LENGTH: 4
<212> TYPE: PRT
<213> ORGANISM: Artificial
<220> FEATURE:
<223> OTHER INFORMATION: peptide

<400> SEQUENCE: 13

Ser Gly Gln Arg
1

<210> SEQ ID NO 14
<211> LENGTH: 4
<212> TYPE: PRT
<213> ORGANISM: Artificial
<220> FEATURE:
<223> OTHER INFORMATION: peptide

<400> SEQUENCE: 14

Ser Val Thr Arg
1

<210> SEQ ID NO 15
<211> LENGTH: 4
<212> TYPE: PRT
<213> ORGANISM: Artificial
<220> FEATURE:
<223> OTHER INFORMATION: peptide

<400> SEQUENCE: 15

Ser Ala Thr Arg
1

<210> SEQ ID NO 16
<211> LENGTH: 4
<212> TYPE: PRT
<213> ORGANISM: Artificial
<220> FEATURE:
<223> OTHER INFORMATION: peptide

<400> SEQUENCE: 16

Ser Phe Asn Arg
1

<210> SEQ ID NO 17
<211> LENGTH: 4
<212> TYPE: PRT
<213> ORGANISM: Artificial
<220> FEATURE:
<223> OTHER INFORMATION: Peptide

<400> SEQUENCE: 17

Ser Trp Lys Lys
1

<210> SEQ ID NO 18
<211> LENGTH: 4
<212> TYPE: PRT
<213> ORGANISM: Artificial
<220> FEATURE:
```

```
<223> OTHER INFORMATION: peptide

<400> SEQUENCE: 18

Ser Glu Ala Arg
1

<210> SEQ ID NO 19
<211> LENGTH: 4
<212> TYPE: PRT
<213> ORGANISM: Artificial
<220> FEATURE:
<223> OTHER INFORMATION: peptide

<400> SEQUENCE: 19

Ser Val Val Lys
1

<210> SEQ ID NO 20
<211> LENGTH: 4
<212> TYPE: PRT
<213> ORGANISM: Artificial
<220> FEATURE:
<223> OTHER INFORMATION: Peptide

<400> SEQUENCE: 20

Ser Asp Tyr Lys
1

<210> SEQ ID NO 21
<211> LENGTH: 4
<212> TYPE: PRT
<213> ORGANISM: Artificial
<220> FEATURE:
<223> OTHER INFORMATION: peptide

<400> SEQUENCE: 21

Ser Val Arg Lys
1

<210> SEQ ID NO 22
<211> LENGTH: 4
<212> TYPE: PRT
<213> ORGANISM: Artificial
<220> FEATURE:
<223> OTHER INFORMATION: peptide

<400> SEQUENCE: 22

Ser Pro Arg Arg
1

<210> SEQ ID NO 23
<211> LENGTH: 4
<212> TYPE: PRT
<213> ORGANISM: Artificial
<220> FEATURE:
<223> OTHER INFORMATION: peptide

<400> SEQUENCE: 23

Ser Met Asp Arg
1

<210> SEQ ID NO 24
<211> LENGTH: 4
<212> TYPE: PRT
<213> ORGANISM: Artificial
<220> FEATURE:
<223> OTHER INFORMATION: peptide
```

```
<400> SEQUENCE: 24

Ser Leu Gly Arg
1

<210> SEQ ID NO 25
<211> LENGTH: 4
<212> TYPE: PRT
<213> ORGANISM: Artificial
<220> FEATURE:
<223> OTHER INFORMATION: peptide

<400> SEQUENCE: 25

Ser Lys Gly Arg
1

<210> SEQ ID NO 26
<211> LENGTH: 4
<212> TYPE: PRT
<213> ORGANISM: Artificial
<220> FEATURE:
<223> OTHER INFORMATION: Peptide

<400> SEQUENCE: 26

Ser Gly Asn Arg
1

<210> SEQ ID NO 27
<211> LENGTH: 4
<212> TYPE: PRT
<213> ORGANISM: Artificial
<220> FEATURE:
<223> OTHER INFORMATION: Peptide

<400> SEQUENCE: 27

Ser Met His Arg
1

<210> SEQ ID NO 28
<211> LENGTH: 4
<212> TYPE: PRT
<213> ORGANISM: Artificial
<220> FEATURE:
<223> OTHER INFORMATION: peptide

<400> SEQUENCE: 28

Ser Leu Leu Arg
1

<210> SEQ ID NO 29
<211> LENGTH: 5
<212> TYPE: PRT
<213> ORGANISM: Artificial Sequence
<220> FEATURE:
<223> OTHER INFORMATION: Peptide

<400> SEQUENCE: 29

Ser Met Thr Arg Gln
1               5

<210> SEQ ID NO 30
<211> LENGTH: 5
<212> TYPE: PRT
<213> ORGANISM: Artificial Sequence
<220> FEATURE:
<223> OTHER INFORMATION: peptide
```

<400> SEQUENCE: 30

Ser Met Thr Arg Phe
1               5

<210> SEQ ID NO 31
<211> LENGTH: 5
<212> TYPE: PRT
<213> ORGANISM: Artificial Sequence
<220> FEATURE:
<223> OTHER INFORMATION: peptide

<400> SEQUENCE: 31

Ser Met Thr Arg His
1               5

<210> SEQ ID NO 32
<211> LENGTH: 5
<212> TYPE: PRT
<213> ORGANISM: Artificial Sequence
<220> FEATURE:
<223> OTHER INFORMATION: Peptide

<400> SEQUENCE: 32

Ser Met Thr Arg Arg
1               5

<210> SEQ ID NO 33
<211> LENGTH: 5
<212> TYPE: PRT
<213> ORGANISM: Artificial Sequence
<220> FEATURE:
<223> OTHER INFORMATION: Peptide

<400> SEQUENCE: 33

Ser Met Thr Arg Lys
1               5

<210> SEQ ID NO 34
<211> LENGTH: 5
<212> TYPE: PRT
<213> ORGANISM: Artificial Sequence
<220> FEATURE:
<223> OTHER INFORMATION: Peptide

<400> SEQUENCE: 34

Ser Met Thr Arg Cys
1               5

<210> SEQ ID NO 35
<211> LENGTH: 5
<212> TYPE: PRT
<213> ORGANISM: Artificial Sequence
<220> FEATURE:
<223> OTHER INFORMATION: Peptide

<400> SEQUENCE: 35

Ser Met Thr Arg Leu
1               5

<210> SEQ ID NO 36
<211> LENGTH: 5
<212> TYPE: PRT
<213> ORGANISM: Artificial Sequence
<220> FEATURE:
<223> OTHER INFORMATION: Peptide

<400> SEQUENCE: 36

```
Ser Met Thr Arg Tyr
1               5

<210> SEQ ID NO 37
<211> LENGTH: 5
<212> TYPE: PRT
<213> ORGANISM: Artificial Sequence
<220> FEATURE:
<223> OTHER INFORMATION: peptide

<400> SEQUENCE: 37

Ser Met Thr Arg Asn
1               5

<210> SEQ ID NO 38
<211> LENGTH: 5
<212> TYPE: PRT
<213> ORGANISM: Artificial Sequence
<220> FEATURE:
<223> OTHER INFORMATION: peptide

<400> SEQUENCE: 38

Ser Met Thr Arg Ile
1               5

<210> SEQ ID NO 39
<211> LENGTH: 5
<212> TYPE: PRT
<213> ORGANISM: Artificial Sequence
<220> FEATURE:
<223> OTHER INFORMATION: Peptide

<400> SEQUENCE: 39

Ser Met Thr Arg Asp
1               5

<210> SEQ ID NO 40
<211> LENGTH: 5
<212> TYPE: PRT
<213> ORGANISM: Artificial Sequence
<220> FEATURE:
<223> OTHER INFORMATION: peptide

<400> SEQUENCE: 40

Ser Met Thr Arg Trp
1               5

<210> SEQ ID NO 41
<211> LENGTH: 5
<212> TYPE: PRT
<213> ORGANISM: Artificial Sequence
<220> FEATURE:
<223> OTHER INFORMATION: peptide

<400> SEQUENCE: 41

Ser Met Thr Arg Glu
1               5

<210> SEQ ID NO 42
<211> LENGTH: 5
<212> TYPE: PRT
<213> ORGANISM: Artificial Sequence
<220> FEATURE:
<223> OTHER INFORMATION: peptide

<400> SEQUENCE: 42
```

```
Ser Met Thr Arg Val
1               5

<210> SEQ ID NO 43
<211> LENGTH: 5
<212> TYPE: PRT
<213> ORGANISM: Artificial Sequence
<220> FEATURE:
<223> OTHER INFORMATION: peptide

<400> SEQUENCE: 43

Ser Met Thr Arg Met
1               5

<210> SEQ ID NO 44
<211> LENGTH: 5
<212> TYPE: PRT
<213> ORGANISM: Artificial Sequence
<220> FEATURE:
<223> OTHER INFORMATION: peptide

<400> SEQUENCE: 44

Ser Met Thr Arg Ala
1               5

<210> SEQ ID NO 45
<211> LENGTH: 5
<212> TYPE: PRT
<213> ORGANISM: Artificial Sequence
<220> FEATURE:
<223> OTHER INFORMATION: peptide

<400> SEQUENCE: 45

Ser Met Thr Arg Thr
1               5

<210> SEQ ID NO 46
<211> LENGTH: 5
<212> TYPE: PRT
<213> ORGANISM: Artificial Sequence
<220> FEATURE:
<223> OTHER INFORMATION: peptide

<400> SEQUENCE: 46

Ser Met Thr Arg Pro
1               5

<210> SEQ ID NO 47
<211> LENGTH: 5
<212> TYPE: PRT
<213> ORGANISM: Artificial Sequence
<220> FEATURE:
<223> OTHER INFORMATION: peptide

<400> SEQUENCE: 47

Ser Gly Gln Arg Gln
1               5

<210> SEQ ID NO 48
<211> LENGTH: 5
<212> TYPE: PRT
<213> ORGANISM: Artificial Sequence
<220> FEATURE:
<223> OTHER INFORMATION: peptide

<400> SEQUENCE: 48

Ser Gly Gln Arg Phe
```

```
1               5

<210> SEQ ID NO 49
<211> LENGTH: 5
<212> TYPE: PRT
<213> ORGANISM: Artificial Sequence
<220> FEATURE:
<223> OTHER INFORMATION: peptide

<400> SEQUENCE: 49

Ser Gly Gln Arg His
1               5

<210> SEQ ID NO 50
<211> LENGTH: 5
<212> TYPE: PRT
<213> ORGANISM: Artificial Sequence
<220> FEATURE:
<223> OTHER INFORMATION: peptide

<400> SEQUENCE: 50

Ser Gly Gln Arg Arg
1               5

<210> SEQ ID NO 51
<211> LENGTH: 5
<212> TYPE: PRT
<213> ORGANISM: Artificial Sequence
<220> FEATURE:
<223> OTHER INFORMATION: peptide

<400> SEQUENCE: 51

Ser Gly Gln Arg Lys
1               5

<210> SEQ ID NO 52
<211> LENGTH: 5
<212> TYPE: PRT
<213> ORGANISM: Artificial Sequence
<220> FEATURE:
<223> OTHER INFORMATION: peptide

<400> SEQUENCE: 52

Ser Gly Gln Arg Cys
1               5

<210> SEQ ID NO 53
<211> LENGTH: 5
<212> TYPE: PRT
<213> ORGANISM: Artificial Sequence
<220> FEATURE:
<223> OTHER INFORMATION: peptide

<400> SEQUENCE: 53

Ser Gly Gln Arg Leu
1               5

<210> SEQ ID NO 54
<211> LENGTH: 5
<212> TYPE: PRT
<213> ORGANISM: Artificial Sequence
<220> FEATURE:
<223> OTHER INFORMATION: peptide

<400> SEQUENCE: 54

Ser Gly Gln Arg Tyr
1               5
```

```
<210> SEQ ID NO 55
<211> LENGTH: 5
<212> TYPE: PRT
<213> ORGANISM: Artificial Sequence
<220> FEATURE:
<223> OTHER INFORMATION: peptide

<400> SEQUENCE: 55

Ser Gly Gln Arg Asn
1               5

<210> SEQ ID NO 56
<211> LENGTH: 5
<212> TYPE: PRT
<213> ORGANISM: Artificial Sequence
<220> FEATURE:
<223> OTHER INFORMATION: peptide

<400> SEQUENCE: 56

Ser Gly Gln Arg Ile
1               5

<210> SEQ ID NO 57
<211> LENGTH: 5
<212> TYPE: PRT
<213> ORGANISM: Artificial Sequence
<220> FEATURE:
<223> OTHER INFORMATION: peptide

<400> SEQUENCE: 57

Ser Gly Gln Arg Asp
1               5

<210> SEQ ID NO 58
<211> LENGTH: 5
<212> TYPE: PRT
<213> ORGANISM: Artificial Sequence
<220> FEATURE:
<223> OTHER INFORMATION: peptide

<400> SEQUENCE: 58

Ser Gly Gln Arg Trp
1               5

<210> SEQ ID NO 59
<211> LENGTH: 5
<212> TYPE: PRT
<213> ORGANISM: Artificial Sequence
<220> FEATURE:
<223> OTHER INFORMATION: peptide

<400> SEQUENCE: 59

Ser Gly Gln Arg Glu
1               5

<210> SEQ ID NO 60
<211> LENGTH: 5
<212> TYPE: PRT
<213> ORGANISM: Artificial Sequence
<220> FEATURE:
<223> OTHER INFORMATION: peptide

<400> SEQUENCE: 60

Ser Gly Gln Arg Val
1               5
```

```
<210> SEQ ID NO 61
<211> LENGTH: 5
<212> TYPE: PRT
<213> ORGANISM: Artificial Sequence
<220> FEATURE:
<223> OTHER INFORMATION: peptide

<400> SEQUENCE: 61

Ser Gly Gln Arg Met
1               5

<210> SEQ ID NO 62
<211> LENGTH: 5
<212> TYPE: PRT
<213> ORGANISM: Artificial Sequence
<220> FEATURE:
<223> OTHER INFORMATION: peptide

<400> SEQUENCE: 62

Ser Gly Gln Arg Ala
1               5

<210> SEQ ID NO 63
<211> LENGTH: 5
<212> TYPE: PRT
<213> ORGANISM: Artificial Sequence
<220> FEATURE:
<223> OTHER INFORMATION: peptide

<400> SEQUENCE: 63

Ser Gly Gln Arg Thr
1               5

<210> SEQ ID NO 64
<211> LENGTH: 5
<212> TYPE: PRT
<213> ORGANISM: Artificial Sequence
<220> FEATURE:
<223> OTHER INFORMATION: peptide

<400> SEQUENCE: 64

Ser Gly Gln Arg Pro
1               5

<210> SEQ ID NO 65
<211> LENGTH: 5
<212> TYPE: PRT
<213> ORGANISM: Artificial Sequence
<220> FEATURE:
<223> OTHER INFORMATION: peptide

<400> SEQUENCE: 65

Ser Val Thr Arg Gln
1               5

<210> SEQ ID NO 66
<211> LENGTH: 5
<212> TYPE: PRT
<213> ORGANISM: Artificial Sequence
<220> FEATURE:
<223> OTHER INFORMATION: peptide

<400> SEQUENCE: 66

Ser Val Thr Arg Phe
1               5
```

```
<210> SEQ ID NO 67
<211> LENGTH: 5
<212> TYPE: PRT
<213> ORGANISM: Artificial Sequence
<220> FEATURE:
<223> OTHER INFORMATION: peptide

<400> SEQUENCE: 67

Ser Val Thr Arg His
1               5

<210> SEQ ID NO 68
<211> LENGTH: 5
<212> TYPE: PRT
<213> ORGANISM: Artificial Sequence
<220> FEATURE:
<223> OTHER INFORMATION: peptide

<400> SEQUENCE: 68

Ser Val Thr Arg Arg
1               5

<210> SEQ ID NO 69
<211> LENGTH: 5
<212> TYPE: PRT
<213> ORGANISM: Artificial Sequence
<220> FEATURE:
<223> OTHER INFORMATION: peptide

<400> SEQUENCE: 69

Ser Val Thr Arg Lys
1               5

<210> SEQ ID NO 70
<211> LENGTH: 5
<212> TYPE: PRT
<213> ORGANISM: Artificial Sequence
<220> FEATURE:
<223> OTHER INFORMATION: peptide

<400> SEQUENCE: 70

Ser Val Thr Arg Cys
1               5

<210> SEQ ID NO 71
<211> LENGTH: 5
<212> TYPE: PRT
<213> ORGANISM: Artificial Sequence
<220> FEATURE:
<223> OTHER INFORMATION: peptide

<400> SEQUENCE: 71

Ser Val Thr Arg Leu
1               5

<210> SEQ ID NO 72
<211> LENGTH: 5
<212> TYPE: PRT
<213> ORGANISM: Artificial Sequence
<220> FEATURE:
<223> OTHER INFORMATION: peptide

<400> SEQUENCE: 72

Ser Val Thr Arg Tyr
1               5

<210> SEQ ID NO 73
```

```
<211> LENGTH: 5
<212> TYPE: PRT
<213> ORGANISM: Artificial Sequence
<220> FEATURE:
<223> OTHER INFORMATION: peptide

<400> SEQUENCE: 73

Ser Val Thr Arg Asn
1               5

<210> SEQ ID NO 74
<211> LENGTH: 5
<212> TYPE: PRT
<213> ORGANISM: Artificial Sequence
<220> FEATURE:
<223> OTHER INFORMATION: peptide

<400> SEQUENCE: 74

Ser Val Thr Arg Ile
1               5

<210> SEQ ID NO 75
<211> LENGTH: 5
<212> TYPE: PRT
<213> ORGANISM: Artificial Sequence
<220> FEATURE:
<223> OTHER INFORMATION: peptide

<400> SEQUENCE: 75

Ser Val Thr Arg Asp
1               5

<210> SEQ ID NO 76
<211> LENGTH: 5
<212> TYPE: PRT
<213> ORGANISM: Artificial Sequence
<220> FEATURE:
<223> OTHER INFORMATION: peptide

<400> SEQUENCE: 76

Ser Val Thr Arg Trp
1               5

<210> SEQ ID NO 77
<211> LENGTH: 5
<212> TYPE: PRT
<213> ORGANISM: Artificial Sequence
<220> FEATURE:
<223> OTHER INFORMATION: peptide

<400> SEQUENCE: 77

Ser Val Thr Arg Glu
1               5

<210> SEQ ID NO 78
<211> LENGTH: 5
<212> TYPE: PRT
<213> ORGANISM: Artificial Sequence
<220> FEATURE:
<223> OTHER INFORMATION: peptide

<400> SEQUENCE: 78

Ser Val Thr Arg Val
1               5

<210> SEQ ID NO 79
<211> LENGTH: 5
```

```
<212> TYPE: PRT
<213> ORGANISM: Artificial Sequence
<220> FEATURE:
<223> OTHER INFORMATION: peptide

<400> SEQUENCE: 79

Ser Val Thr Arg Met
1               5

<210> SEQ ID NO 80
<211> LENGTH: 5
<212> TYPE: PRT
<213> ORGANISM: Artificial Sequence
<220> FEATURE:
<223> OTHER INFORMATION: peptide

<400> SEQUENCE: 80

Ser Val Thr Arg Ala
1               5

<210> SEQ ID NO 81
<211> LENGTH: 5
<212> TYPE: PRT
<213> ORGANISM: Artificial Sequence
<220> FEATURE:
<223> OTHER INFORMATION: peptide

<400> SEQUENCE: 81

Ser Val Thr Arg Thr
1               5

<210> SEQ ID NO 82
<211> LENGTH: 5
<212> TYPE: PRT
<213> ORGANISM: Artificial Sequence
<220> FEATURE:
<223> OTHER INFORMATION: peptide

<400> SEQUENCE: 82

Ser Val Thr Arg Pro
1               5

<210> SEQ ID NO 83
<211> LENGTH: 5
<212> TYPE: PRT
<213> ORGANISM: Artificial Sequence
<220> FEATURE:
<223> OTHER INFORMATION: peptide

<400> SEQUENCE: 83

Ser Ala Thr Arg Gln
1               5

<210> SEQ ID NO 84
<211> LENGTH: 5
<212> TYPE: PRT
<213> ORGANISM: Artificial Sequence
<220> FEATURE:
<223> OTHER INFORMATION: peptide

<400> SEQUENCE: 84

Ser Ala Thr Arg Phe
1               5

<210> SEQ ID NO 85
<211> LENGTH: 5
<212> TYPE: PRT
```

```
<213> ORGANISM: Artificial Sequence
<220> FEATURE:
<223> OTHER INFORMATION: peptide

<400> SEQUENCE: 85

Ser Ala Thr Arg His
1               5

<210> SEQ ID NO 86
<211> LENGTH: 5
<212> TYPE: PRT
<213> ORGANISM: Artificial Sequence
<220> FEATURE:
<223> OTHER INFORMATION: peptide

<400> SEQUENCE: 86

Ser Ala Thr Arg Arg
1               5

<210> SEQ ID NO 87
<211> LENGTH: 5
<212> TYPE: PRT
<213> ORGANISM: Artificial Sequence
<220> FEATURE:
<223> OTHER INFORMATION: peptide

<400> SEQUENCE: 87

Ser Ala Thr Arg Lys
1               5

<210> SEQ ID NO 88
<211> LENGTH: 5
<212> TYPE: PRT
<213> ORGANISM: Artificial Sequence
<220> FEATURE:
<223> OTHER INFORMATION: peptide

<400> SEQUENCE: 88

Ser Ala Thr Arg Cys
1               5

<210> SEQ ID NO 89
<211> LENGTH: 5
<212> TYPE: PRT
<213> ORGANISM: Artificial Sequence
<220> FEATURE:
<223> OTHER INFORMATION: peptide

<400> SEQUENCE: 89

Ser Ala Thr Arg Leu
1               5

<210> SEQ ID NO 90
<211> LENGTH: 5
<212> TYPE: PRT
<213> ORGANISM: Artificial Sequence
<220> FEATURE:
<223> OTHER INFORMATION: peptide

<400> SEQUENCE: 90

Ser Ala Thr Arg Tyr
1               5

<210> SEQ ID NO 91
<211> LENGTH: 5
<212> TYPE: PRT
<213> ORGANISM: Artificial Sequence
```

```
<220> FEATURE:
<223> OTHER INFORMATION: peptide

<400> SEQUENCE: 91

Ser Ala Thr Arg Asn
1               5

<210> SEQ ID NO 92
<211> LENGTH: 5
<212> TYPE: PRT
<213> ORGANISM: Artificial Sequence
<220> FEATURE:
<223> OTHER INFORMATION: peptide

<400> SEQUENCE: 92

Ser Ala Thr Arg Ile
1               5

<210> SEQ ID NO 93
<211> LENGTH: 5
<212> TYPE: PRT
<213> ORGANISM: Artificial Sequence
<220> FEATURE:
<223> OTHER INFORMATION: peptide

<400> SEQUENCE: 93

Ser Ala Thr Arg Asp
1               5

<210> SEQ ID NO 94
<211> LENGTH: 5
<212> TYPE: PRT
<213> ORGANISM: Artificial Sequence
<220> FEATURE:
<223> OTHER INFORMATION: peptide

<400> SEQUENCE: 94

Ser Ala Thr Arg Trp
1               5

<210> SEQ ID NO 95
<211> LENGTH: 5
<212> TYPE: PRT
<213> ORGANISM: Artificial Sequence
<220> FEATURE:
<223> OTHER INFORMATION: peptide

<400> SEQUENCE: 95

Ser Ala Thr Arg Glu
1               5

<210> SEQ ID NO 96
<211> LENGTH: 5
<212> TYPE: PRT
<213> ORGANISM: Artificial Sequence
<220> FEATURE:
<223> OTHER INFORMATION: peptide

<400> SEQUENCE: 96

Ser Ala Thr Arg Val
1               5

<210> SEQ ID NO 97
<211> LENGTH: 5
<212> TYPE: PRT
<213> ORGANISM: Artificial Sequence
<220> FEATURE:
```

```
<223> OTHER INFORMATION: SATRM

<400> SEQUENCE: 97

Ser Ala Thr Arg Met
1               5

<210> SEQ ID NO 98
<211> LENGTH: 5
<212> TYPE: PRT
<213> ORGANISM: Artificial Sequence
<220> FEATURE:
<223> OTHER INFORMATION: peptide

<400> SEQUENCE: 98

Ser Ala Thr Arg Ala
1               5

<210> SEQ ID NO 99
<211> LENGTH: 5
<212> TYPE: PRT
<213> ORGANISM: Artificial Sequence
<220> FEATURE:
<223> OTHER INFORMATION: peptide

<400> SEQUENCE: 99

Ser Ala Thr Arg Thr
1               5

<210> SEQ ID NO 100
<211> LENGTH: 5
<212> TYPE: PRT
<213> ORGANISM: Artificial Sequence
<220> FEATURE:
<223> OTHER INFORMATION: peptide

<400> SEQUENCE: 100

Ser Ala Thr Arg Pro
1               5

<210> SEQ ID NO 101
<211> LENGTH: 5
<212> TYPE: PRT
<213> ORGANISM: Artificial Sequence
<220> FEATURE:
<223> OTHER INFORMATION: peptide

<400> SEQUENCE: 101

Ser Phe Asn Arg Gln
1               5

<210> SEQ ID NO 102
<211> LENGTH: 5
<212> TYPE: PRT
<213> ORGANISM: Artificial Sequence
<220> FEATURE:
<223> OTHER INFORMATION: peptide

<400> SEQUENCE: 102

Ser Phe Asn Arg Phe
1               5

<210> SEQ ID NO 103
<211> LENGTH: 5
<212> TYPE: PRT
<213> ORGANISM: Artificial Sequence
<220> FEATURE:
<223> OTHER INFORMATION: peptide
```

```
<400> SEQUENCE: 103

Ser Phe Asn Arg His
1               5

<210> SEQ ID NO 104
<211> LENGTH: 5
<212> TYPE: PRT
<213> ORGANISM: Artificial Sequence
<220> FEATURE:
<223> OTHER INFORMATION: peptide

<400> SEQUENCE: 104

Ser Phe Asn Arg Arg
1               5

<210> SEQ ID NO 105
<211> LENGTH: 5
<212> TYPE: PRT
<213> ORGANISM: Artificial Sequence
<220> FEATURE:
<223> OTHER INFORMATION: peptide

<400> SEQUENCE: 105

Ser Phe Asn Arg Lys
1               5

<210> SEQ ID NO 106
<211> LENGTH: 5
<212> TYPE: PRT
<213> ORGANISM: Artificial Sequence
<220> FEATURE:
<223> OTHER INFORMATION: peptide

<400> SEQUENCE: 106

Ser Phe Asn Arg Cys
1               5

<210> SEQ ID NO 107
<211> LENGTH: 5
<212> TYPE: PRT
<213> ORGANISM: Artificial Sequence
<220> FEATURE:
<223> OTHER INFORMATION: peptide

<400> SEQUENCE: 107

Ser Phe Asn Arg Leu
1               5

<210> SEQ ID NO 108
<211> LENGTH: 5
<212> TYPE: PRT
<213> ORGANISM: Artificial Sequence
<220> FEATURE:
<223> OTHER INFORMATION: peptide

<400> SEQUENCE: 108

Ser Phe Asn Arg Tyr
1               5

<210> SEQ ID NO 109
<211> LENGTH: 5
<212> TYPE: PRT
<213> ORGANISM: Artificial Sequence
<220> FEATURE:
<223> OTHER INFORMATION: artificial
```

```
<400> SEQUENCE: 109

Ser Phe Asn Arg Asn
1               5

<210> SEQ ID NO 110
<211> LENGTH: 5
<212> TYPE: PRT
<213> ORGANISM: Artificial Sequence
<220> FEATURE:
<223> OTHER INFORMATION: peptide

<400> SEQUENCE: 110

Ser Phe Asn Arg Ile
1               5

<210> SEQ ID NO 111
<211> LENGTH: 5
<212> TYPE: PRT
<213> ORGANISM: Artificial Sequence
<220> FEATURE:
<223> OTHER INFORMATION: peptide

<400> SEQUENCE: 111

Ser Phe Asn Arg Asp
1               5

<210> SEQ ID NO 112
<211> LENGTH: 5
<212> TYPE: PRT
<213> ORGANISM: Artificial Sequence
<220> FEATURE:
<223> OTHER INFORMATION: peptide

<400> SEQUENCE: 112

Ser Phe Asn Arg Trp
1               5

<210> SEQ ID NO 113
<211> LENGTH: 5
<212> TYPE: PRT
<213> ORGANISM: Artificial Sequence
<220> FEATURE:
<223> OTHER INFORMATION: peptide

<400> SEQUENCE: 113

Ser Phe Asn Arg Glu
1               5

<210> SEQ ID NO 114
<211> LENGTH: 5
<212> TYPE: PRT
<213> ORGANISM: Artificial Sequence
<220> FEATURE:
<223> OTHER INFORMATION: peptide

<400> SEQUENCE: 114

Ser Phe Asn Arg Val
1               5

<210> SEQ ID NO 115
<211> LENGTH: 5
<212> TYPE: PRT
<213> ORGANISM: Artificial Sequence
<220> FEATURE:
<223> OTHER INFORMATION: peptide

<400> SEQUENCE: 115
```

```
Ser Phe Asn Arg Met
1               5

<210> SEQ ID NO 116
<211> LENGTH: 5
<212> TYPE: PRT
<213> ORGANISM: Artificial Sequence
<220> FEATURE:
<223> OTHER INFORMATION: peptide

<400> SEQUENCE: 116

Ser Phe Asn Arg Ala
1               5

<210> SEQ ID NO 117
<211> LENGTH: 5
<212> TYPE: PRT
<213> ORGANISM: Artificial Sequence
<220> FEATURE:
<223> OTHER INFORMATION: peptide

<400> SEQUENCE: 117

Ser Phe Asn Arg Thr
1               5

<210> SEQ ID NO 118
<211> LENGTH: 5
<212> TYPE: PRT
<213> ORGANISM: Artificial Sequence
<220> FEATURE:
<223> OTHER INFORMATION: peptide

<400> SEQUENCE: 118

Ser Phe Asn Arg Pro
1               5

<210> SEQ ID NO 119
<211> LENGTH: 5
<212> TYPE: PRT
<213> ORGANISM: Artificial Sequence
<220> FEATURE:
<223> OTHER INFORMATION: peptide

<400> SEQUENCE: 119

Ser Trp Lys Lys Gln
1               5

<210> SEQ ID NO 120
<211> LENGTH: 5
<212> TYPE: PRT
<213> ORGANISM: Artificial Sequence
<220> FEATURE:
<223> OTHER INFORMATION: peptide

<400> SEQUENCE: 120

Ser Trp Lys Lys Phe
1               5

<210> SEQ ID NO 121
<211> LENGTH: 5
<212> TYPE: PRT
<213> ORGANISM: Artificial Sequence
<220> FEATURE:
<223> OTHER INFORMATION: peptide

<400> SEQUENCE: 121
```

```
Ser Trp Lys Lys His
1               5

<210> SEQ ID NO 122
<211> LENGTH: 5
<212> TYPE: PRT
<213> ORGANISM: Artificial Sequence
<220> FEATURE:
<223> OTHER INFORMATION: peptide

<400> SEQUENCE: 122

Ser Trp Lys Lys Arg
1               5

<210> SEQ ID NO 123
<211> LENGTH: 5
<212> TYPE: PRT
<213> ORGANISM: Artificial Sequence
<220> FEATURE:
<223> OTHER INFORMATION: peptide

<400> SEQUENCE: 123

Ser Trp Lys Lys Lys
1               5

<210> SEQ ID NO 124
<211> LENGTH: 5
<212> TYPE: PRT
<213> ORGANISM: Artificial Sequence
<220> FEATURE:
<223> OTHER INFORMATION: peptide

<400> SEQUENCE: 124

Ser Trp Lys Lys Cys
1               5

<210> SEQ ID NO 125
<211> LENGTH: 5
<212> TYPE: PRT
<213> ORGANISM: Artificial Sequence
<220> FEATURE:
<223> OTHER INFORMATION: peptide

<400> SEQUENCE: 125

Ser Trp Lys Lys Leu
1               5

<210> SEQ ID NO 126
<211> LENGTH: 5
<212> TYPE: PRT
<213> ORGANISM: Artificial Sequence
<220> FEATURE:
<223> OTHER INFORMATION: peptide

<400> SEQUENCE: 126

Ser Trp Lys Lys Tyr
1               5

<210> SEQ ID NO 127
<211> LENGTH: 5
<212> TYPE: PRT
<213> ORGANISM: Artificial Sequence
<220> FEATURE:
<223> OTHER INFORMATION: peptide

<400> SEQUENCE: 127

Ser Trp Lys Lys Asn
```

```
1               5

<210> SEQ ID NO 128
<211> LENGTH: 5
<212> TYPE: PRT
<213> ORGANISM: Artificial Sequence
<220> FEATURE:
<223> OTHER INFORMATION: peptide

<400> SEQUENCE: 128

Ser Trp Lys Lys Ile
1               5

<210> SEQ ID NO 129
<211> LENGTH: 5
<212> TYPE: PRT
<213> ORGANISM: Artificial Sequence
<220> FEATURE:
<223> OTHER INFORMATION: peptide

<400> SEQUENCE: 129

Ser Trp Lys Lys Asp
1               5

<210> SEQ ID NO 130
<211> LENGTH: 5
<212> TYPE: PRT
<213> ORGANISM: Artificial Sequence
<220> FEATURE:
<223> OTHER INFORMATION: peptide

<400> SEQUENCE: 130

Ser Trp Lys Lys Trp
1               5

<210> SEQ ID NO 131
<211> LENGTH: 5
<212> TYPE: PRT
<213> ORGANISM: Artificial Sequence
<220> FEATURE:
<223> OTHER INFORMATION: peptide

<400> SEQUENCE: 131

Ser Trp Lys Lys Glu
1               5

<210> SEQ ID NO 132
<211> LENGTH: 5
<212> TYPE: PRT
<213> ORGANISM: Artificial Sequence
<220> FEATURE:
<223> OTHER INFORMATION: peptide

<400> SEQUENCE: 132

Ser Trp Lys Lys Val
1               5

<210> SEQ ID NO 133
<211> LENGTH: 5
<212> TYPE: PRT
<213> ORGANISM: Artificial Sequence
<220> FEATURE:
<223> OTHER INFORMATION: SWKKM

<400> SEQUENCE: 133

Ser Trp Lys Lys Met
1               5
```

<210> SEQ ID NO 134
<211> LENGTH: 5
<212> TYPE: PRT
<213> ORGANISM: Artificial Sequence
<220> FEATURE:
<223> OTHER INFORMATION: peptide

<400> SEQUENCE: 134

Ser Trp Lys Lys Ala
1               5

<210> SEQ ID NO 135
<211> LENGTH: 5
<212> TYPE: PRT
<213> ORGANISM: Artificial Sequence
<220> FEATURE:
<223> OTHER INFORMATION: peptide

<400> SEQUENCE: 135

Ser Trp Lys Lys Thr
1               5

<210> SEQ ID NO 136
<211> LENGTH: 5
<212> TYPE: PRT
<213> ORGANISM: Artificial Sequence
<220> FEATURE:
<223> OTHER INFORMATION: peptide

<400> SEQUENCE: 136

Ser Trp Lys Lys Pro
1               5

<210> SEQ ID NO 137
<211> LENGTH: 5
<212> TYPE: PRT
<213> ORGANISM: Artificial Sequence
<220> FEATURE:
<223> OTHER INFORMATION: peptide

<400> SEQUENCE: 137

Ser Glu Ala Arg Gln
1               5

<210> SEQ ID NO 138
<211> LENGTH: 5
<212> TYPE: PRT
<213> ORGANISM: Artificial Sequence
<220> FEATURE:
<223> OTHER INFORMATION: peptide

<400> SEQUENCE: 138

Ser Glu Ala Arg Phe
1               5

<210> SEQ ID NO 139
<211> LENGTH: 5
<212> TYPE: PRT
<213> ORGANISM: Artificial Sequence
<220> FEATURE:
<223> OTHER INFORMATION: peptide

<400> SEQUENCE: 139

Ser Glu Ala Arg His
1               5

```
<210> SEQ ID NO 140
<211> LENGTH: 5
<212> TYPE: PRT
<213> ORGANISM: Artificial Sequence
<220> FEATURE:
<223> OTHER INFORMATION: peptide

<400> SEQUENCE: 140

Ser Glu Ala Arg Arg
1               5

<210> SEQ ID NO 141
<211> LENGTH: 5
<212> TYPE: PRT
<213> ORGANISM: Artificial Sequence
<220> FEATURE:
<223> OTHER INFORMATION: peptide

<400> SEQUENCE: 141

Ser Glu Ala Arg Lys
1               5

<210> SEQ ID NO 142
<211> LENGTH: 5
<212> TYPE: PRT
<213> ORGANISM: Artificial Sequence
<220> FEATURE:
<223> OTHER INFORMATION: peptide

<400> SEQUENCE: 142

Ser Glu Ala Arg Cys
1               5

<210> SEQ ID NO 143
<211> LENGTH: 5
<212> TYPE: PRT
<213> ORGANISM: Artificial Sequence
<220> FEATURE:
<223> OTHER INFORMATION: peptide

<400> SEQUENCE: 143

Ser Glu Ala Arg Leu
1               5

<210> SEQ ID NO 144
<211> LENGTH: 5
<212> TYPE: PRT
<213> ORGANISM: Artificial Sequence
<220> FEATURE:
<223> OTHER INFORMATION: peptide

<400> SEQUENCE: 144

Ser Glu Ala Arg Tyr
1               5

<210> SEQ ID NO 145
<211> LENGTH: 5
<212> TYPE: PRT
<213> ORGANISM: Artificial Sequence
<220> FEATURE:
<223> OTHER INFORMATION: peptide

<400> SEQUENCE: 145

Ser Glu Ala Arg Asn
1               5
```

```
<210> SEQ ID NO 146
<211> LENGTH: 5
<212> TYPE: PRT
<213> ORGANISM: Artificial Sequence
<220> FEATURE:
<223> OTHER INFORMATION: peptide

<400> SEQUENCE: 146

Ser Glu Ala Arg Ile
1               5

<210> SEQ ID NO 147
<211> LENGTH: 5
<212> TYPE: PRT
<213> ORGANISM: Artificial Sequence
<220> FEATURE:
<223> OTHER INFORMATION: peptide

<400> SEQUENCE: 147

Ser Glu Ala Arg Asp
1               5

<210> SEQ ID NO 148
<211> LENGTH: 5
<212> TYPE: PRT
<213> ORGANISM: Artificial Sequence
<220> FEATURE:
<223> OTHER INFORMATION: peptide

<400> SEQUENCE: 148

Ser Glu Ala Arg Trp
1               5

<210> SEQ ID NO 149
<211> LENGTH: 5
<212> TYPE: PRT
<213> ORGANISM: Artificial Sequence
<220> FEATURE:
<223> OTHER INFORMATION: peptide

<400> SEQUENCE: 149

Ser Glu Ala Arg Glu
1               5

<210> SEQ ID NO 150
<211> LENGTH: 5
<212> TYPE: PRT
<213> ORGANISM: Artificial Sequence
<220> FEATURE:
<223> OTHER INFORMATION: peptide

<400> SEQUENCE: 150

Ser Glu Ala Arg Val
1               5

<210> SEQ ID NO 151
<211> LENGTH: 5
<212> TYPE: PRT
<213> ORGANISM: Artificial Sequence
<220> FEATURE:
<223> OTHER INFORMATION: peptide

<400> SEQUENCE: 151

Ser Glu Ala Arg Met
1               5

<210> SEQ ID NO 152
```

```
<211> LENGTH: 5
<212> TYPE: PRT
<213> ORGANISM: Artificial Sequence
<220> FEATURE:
<223> OTHER INFORMATION: peptide

<400> SEQUENCE: 152

Ser Glu Ala Arg Ala
1               5

<210> SEQ ID NO 153
<211> LENGTH: 5
<212> TYPE: PRT
<213> ORGANISM: Artificial Sequence
<220> FEATURE:
<223> OTHER INFORMATION: peptide

<400> SEQUENCE: 153

Ser Glu Ala Arg Thr
1               5

<210> SEQ ID NO 154
<211> LENGTH: 5
<212> TYPE: PRT
<213> ORGANISM: Artificial Sequence
<220> FEATURE:
<223> OTHER INFORMATION: peptide

<400> SEQUENCE: 154

Ser Glu Ala Arg Pro
1               5

<210> SEQ ID NO 155
<211> LENGTH: 5
<212> TYPE: PRT
<213> ORGANISM: Artificial Sequence
<220> FEATURE:
<223> OTHER INFORMATION: peptide

<400> SEQUENCE: 155

Ser Val Val Lys Gln
1               5

<210> SEQ ID NO 156
<211> LENGTH: 5
<212> TYPE: PRT
<213> ORGANISM: Artificial Sequence
<220> FEATURE:
<223> OTHER INFORMATION: peptide

<400> SEQUENCE: 156

Ser Val Val Lys Phe
1               5

<210> SEQ ID NO 157
<211> LENGTH: 5
<212> TYPE: PRT
<213> ORGANISM: Artificial Sequence
<220> FEATURE:
<223> OTHER INFORMATION: peptide

<400> SEQUENCE: 157

Ser Val Val Lys His
1               5

<210> SEQ ID NO 158
<211> LENGTH: 5
```

```
<212> TYPE: PRT
<213> ORGANISM: Artificial Sequence
<220> FEATURE:
<223> OTHER INFORMATION: peptide

<400> SEQUENCE: 158

Ser Val Val Lys Arg
1               5

<210> SEQ ID NO 159
<211> LENGTH: 5
<212> TYPE: PRT
<213> ORGANISM: Artificial Sequence
<220> FEATURE:
<223> OTHER INFORMATION: petide

<400> SEQUENCE: 159

Ser Val Val Lys Lys
1               5

<210> SEQ ID NO 160
<211> LENGTH: 5
<212> TYPE: PRT
<213> ORGANISM: Artificial Sequence
<220> FEATURE:
<223> OTHER INFORMATION: peptide

<400> SEQUENCE: 160

Ser Val Val Lys Cys
1               5

<210> SEQ ID NO 161
<211> LENGTH: 5
<212> TYPE: PRT
<213> ORGANISM: Artificial Sequence
<220> FEATURE:
<223> OTHER INFORMATION: peptide

<400> SEQUENCE: 161

Ser Val Val Lys Leu
1               5

<210> SEQ ID NO 162
<211> LENGTH: 5
<212> TYPE: PRT
<213> ORGANISM: Artificial Sequence
<220> FEATURE:
<223> OTHER INFORMATION: peptide

<400> SEQUENCE: 162

Ser Val Val Lys Tyr
1               5

<210> SEQ ID NO 163
<211> LENGTH: 5
<212> TYPE: PRT
<213> ORGANISM: Artificial Sequence
<220> FEATURE:
<223> OTHER INFORMATION: peptide

<400> SEQUENCE: 163

Ser Val Val Lys Asn
1               5

<210> SEQ ID NO 164
<211> LENGTH: 5
<212> TYPE: PRT
```

```
<213> ORGANISM: Artificial Sequence
<220> FEATURE:
<223> OTHER INFORMATION: peptide

<400> SEQUENCE: 164

Ser Val Val Lys Ile
1               5

<210> SEQ ID NO 165
<211> LENGTH: 5
<212> TYPE: PRT
<213> ORGANISM: Artificial Sequence
<220> FEATURE:
<223> OTHER INFORMATION: peptide

<400> SEQUENCE: 165

Ser Val Val Lys Asp
1               5

<210> SEQ ID NO 166
<211> LENGTH: 5
<212> TYPE: PRT
<213> ORGANISM: Artificial Sequence
<220> FEATURE:
<223> OTHER INFORMATION: peptide

<400> SEQUENCE: 166

Ser Val Val Lys Trp
1               5

<210> SEQ ID NO 167
<211> LENGTH: 5
<212> TYPE: PRT
<213> ORGANISM: Artificial Sequence
<220> FEATURE:
<223> OTHER INFORMATION: peptide

<400> SEQUENCE: 167

Ser Val Val Lys Glu
1               5

<210> SEQ ID NO 168
<211> LENGTH: 5
<212> TYPE: PRT
<213> ORGANISM: Artificial Sequence
<220> FEATURE:
<223> OTHER INFORMATION: peptide

<400> SEQUENCE: 168

Ser Val Val Lys Val
1               5

<210> SEQ ID NO 169
<211> LENGTH: 5
<212> TYPE: PRT
<213> ORGANISM: Artificial Sequence
<220> FEATURE:
<223> OTHER INFORMATION: peptide

<400> SEQUENCE: 169

Ser Val Val Lys Met
1               5

<210> SEQ ID NO 170
<211> LENGTH: 5
<212> TYPE: PRT
<213> ORGANISM: Artificial Sequence
```

```
<220> FEATURE:
<223> OTHER INFORMATION: peptide

<400> SEQUENCE: 170

Ser Val Val Lys Ala
1               5

<210> SEQ ID NO 171
<211> LENGTH: 5
<212> TYPE: PRT
<213> ORGANISM: Artificial Sequence
<220> FEATURE:
<223> OTHER INFORMATION: peptide

<400> SEQUENCE: 171

Ser Val Val Lys Thr
1               5

<210> SEQ ID NO 172
<211> LENGTH: 5
<212> TYPE: PRT
<213> ORGANISM: Artificial Sequence
<220> FEATURE:
<223> OTHER INFORMATION: peptide

<400> SEQUENCE: 172

Ser Val Val Lys Pro
1               5

<210> SEQ ID NO 173
<211> LENGTH: 5
<212> TYPE: PRT
<213> ORGANISM: Artificial Sequence
<220> FEATURE:
<223> OTHER INFORMATION: peptide

<400> SEQUENCE: 173

Ser Asp Tyr Lys Gln
1               5

<210> SEQ ID NO 174
<211> LENGTH: 5
<212> TYPE: PRT
<213> ORGANISM: Artificial Sequence
<220> FEATURE:
<223> OTHER INFORMATION: peptide

<400> SEQUENCE: 174

Ser Asp Tyr Lys Phe
1               5

<210> SEQ ID NO 175
<211> LENGTH: 5
<212> TYPE: PRT
<213> ORGANISM: Artificial Sequence
<220> FEATURE:
<223> OTHER INFORMATION: peptide

<400> SEQUENCE: 175

Ser Asp Tyr Lys His
1               5

<210> SEQ ID NO 176
<211> LENGTH: 5
<212> TYPE: PRT
<213> ORGANISM: Artificial Sequence
<220> FEATURE:
```

```
<223> OTHER INFORMATION: peptide

<400> SEQUENCE: 176

Ser Asp Tyr Lys Arg
1               5

<210> SEQ ID NO 177
<211> LENGTH: 5
<212> TYPE: PRT
<213> ORGANISM: Artificial Sequence
<220> FEATURE:
<223> OTHER INFORMATION: peptide

<400> SEQUENCE: 177

Ser Asp Tyr Lys Lys
1               5

<210> SEQ ID NO 178
<211> LENGTH: 5
<212> TYPE: PRT
<213> ORGANISM: Artificial Sequence
<220> FEATURE:
<223> OTHER INFORMATION: peptide

<400> SEQUENCE: 178

Ser Asp Tyr Lys Cys
1               5

<210> SEQ ID NO 179
<211> LENGTH: 5
<212> TYPE: PRT
<213> ORGANISM: Artificial Sequence
<220> FEATURE:
<223> OTHER INFORMATION: peptide

<400> SEQUENCE: 179

Ser Asp Tyr Lys Leu
1               5

<210> SEQ ID NO 180
<211> LENGTH: 5
<212> TYPE: PRT
<213> ORGANISM: Artificial Sequence
<220> FEATURE:
<223> OTHER INFORMATION: peptide

<400> SEQUENCE: 180

Ser Asp Tyr Lys Tyr
1               5

<210> SEQ ID NO 181
<211> LENGTH: 5
<212> TYPE: PRT
<213> ORGANISM: Artificial Sequence
<220> FEATURE:
<223> OTHER INFORMATION: peptide

<400> SEQUENCE: 181

Ser Asp Tyr Lys Asn
1               5

<210> SEQ ID NO 182
<211> LENGTH: 5
<212> TYPE: PRT
<213> ORGANISM: Artificial Sequence
<220> FEATURE:
<223> OTHER INFORMATION: peptide
```

```
<400> SEQUENCE: 182

Ser Asp Tyr Lys Ile
1               5

<210> SEQ ID NO 183
<211> LENGTH: 5
<212> TYPE: PRT
<213> ORGANISM: Artificial Sequence
<220> FEATURE:
<223> OTHER INFORMATION: peptide

<400> SEQUENCE: 183

Ser Asp Tyr Lys Asp
1               5

<210> SEQ ID NO 184
<211> LENGTH: 5
<212> TYPE: PRT
<213> ORGANISM: Artificial Sequence
<220> FEATURE:
<223> OTHER INFORMATION: peptide

<400> SEQUENCE: 184

Ser Asp Tyr Lys Trp
1               5

<210> SEQ ID NO 185
<211> LENGTH: 5
<212> TYPE: PRT
<213> ORGANISM: Artificial Sequence
<220> FEATURE:
<223> OTHER INFORMATION: peptide

<400> SEQUENCE: 185

Ser Asp Tyr Lys Glu
1               5

<210> SEQ ID NO 186
<211> LENGTH: 5
<212> TYPE: PRT
<213> ORGANISM: Artificial Sequence
<220> FEATURE:
<223> OTHER INFORMATION: peptide

<400> SEQUENCE: 186

Ser Asp Tyr Lys Val
1               5

<210> SEQ ID NO 187
<211> LENGTH: 5
<212> TYPE: PRT
<213> ORGANISM: Artificial Sequence
<220> FEATURE:
<223> OTHER INFORMATION: peptide

<400> SEQUENCE: 187

Ser Asp Tyr Lys Met
1               5

<210> SEQ ID NO 188
<211> LENGTH: 5
<212> TYPE: PRT
<213> ORGANISM: Artificial Sequence
<220> FEATURE:
<223> OTHER INFORMATION: peptide
```

```
<400> SEQUENCE: 188

Ser Asp Tyr Lys Ala
1               5

<210> SEQ ID NO 189
<211> LENGTH: 5
<212> TYPE: PRT
<213> ORGANISM: Artificial Sequence
<220> FEATURE:
<223> OTHER INFORMATION: peptide

<400> SEQUENCE: 189

Ser Asp Tyr Lys Thr
1               5

<210> SEQ ID NO 190
<211> LENGTH: 5
<212> TYPE: PRT
<213> ORGANISM: Artificial Sequence
<220> FEATURE:
<223> OTHER INFORMATION: peptide

<400> SEQUENCE: 190

Ser Asp Tyr Lys Pro
1               5

<210> SEQ ID NO 191
<211> LENGTH: 5
<212> TYPE: PRT
<213> ORGANISM: Artificial Sequence
<220> FEATURE:
<223> OTHER INFORMATION: peptide

<400> SEQUENCE: 191

Ser Val Arg Lys Gln
1               5

<210> SEQ ID NO 192
<211> LENGTH: 5
<212> TYPE: PRT
<213> ORGANISM: Artificial Sequence
<220> FEATURE:
<223> OTHER INFORMATION: peptide

<400> SEQUENCE: 192

Ser Val Arg Lys Phe
1               5

<210> SEQ ID NO 193
<211> LENGTH: 5
<212> TYPE: PRT
<213> ORGANISM: Artificial Sequence
<220> FEATURE:
<223> OTHER INFORMATION: peptide

<400> SEQUENCE: 193

Ser Val Arg Lys His
1               5

<210> SEQ ID NO 194
<211> LENGTH: 5
<212> TYPE: PRT
<213> ORGANISM: Artificial Sequence
<220> FEATURE:
<223> OTHER INFORMATION: peptide

<400> SEQUENCE: 194
```

```
Ser Val Arg Lys Arg
1               5

<210> SEQ ID NO 195
<211> LENGTH: 5
<212> TYPE: PRT
<213> ORGANISM: Artificial Sequence
<220> FEATURE:
<223> OTHER INFORMATION: peptide

<400> SEQUENCE: 195

Ser Val Arg Lys Lys
1               5

<210> SEQ ID NO 196
<211> LENGTH: 5
<212> TYPE: PRT
<213> ORGANISM: Artificial Sequence
<220> FEATURE:
<223> OTHER INFORMATION: peptide

<400> SEQUENCE: 196

Ser Val Arg Lys Cys
1               5

<210> SEQ ID NO 197
<211> LENGTH: 5
<212> TYPE: PRT
<213> ORGANISM: Artificial Sequence
<220> FEATURE:
<223> OTHER INFORMATION: peptide

<400> SEQUENCE: 197

Ser Val Arg Lys Leu
1               5

<210> SEQ ID NO 198
<211> LENGTH: 5
<212> TYPE: PRT
<213> ORGANISM: Artificial Sequence
<220> FEATURE:
<223> OTHER INFORMATION: peptide

<400> SEQUENCE: 198

Ser Val Arg Lys Tyr
1               5

<210> SEQ ID NO 199
<211> LENGTH: 5
<212> TYPE: PRT
<213> ORGANISM: Artificial Sequence
<220> FEATURE:
<223> OTHER INFORMATION: peptide

<400> SEQUENCE: 199

Ser Val Arg Lys Asn
1               5

<210> SEQ ID NO 200
<211> LENGTH: 5
<212> TYPE: PRT
<213> ORGANISM: Artificial Sequence
<220> FEATURE:
<223> OTHER INFORMATION: peptide

<400> SEQUENCE: 200
```

Ser Val Arg Lys Ile
1               5

<210> SEQ ID NO 201
<211> LENGTH: 5
<212> TYPE: PRT
<213> ORGANISM: Artificial Sequence
<220> FEATURE:
<223> OTHER INFORMATION: peptide

<400> SEQUENCE: 201

Ser Val Arg Lys Asp
1               5

<210> SEQ ID NO 202
<211> LENGTH: 5
<212> TYPE: PRT
<213> ORGANISM: Artificial Sequence
<220> FEATURE:
<223> OTHER INFORMATION: peptide

<400> SEQUENCE: 202

Ser Val Arg Lys Trp
1               5

<210> SEQ ID NO 203
<211> LENGTH: 5
<212> TYPE: PRT
<213> ORGANISM: Artificial Sequence
<220> FEATURE:
<223> OTHER INFORMATION: peptide

<400> SEQUENCE: 203

Ser Val Arg Lys Glu
1               5

<210> SEQ ID NO 204
<211> LENGTH: 5
<212> TYPE: PRT
<213> ORGANISM: Artificial Sequence
<220> FEATURE:
<223> OTHER INFORMATION: peptide

<400> SEQUENCE: 204

Ser Val Arg Lys Val
1               5

<210> SEQ ID NO 205
<211> LENGTH: 5
<212> TYPE: PRT
<213> ORGANISM: Artificial Sequence
<220> FEATURE:
<223> OTHER INFORMATION: peptide

<400> SEQUENCE: 205

Ser Val Arg Lys Met
1               5

<210> SEQ ID NO 206
<211> LENGTH: 5
<212> TYPE: PRT
<213> ORGANISM: Artificial Sequence
<220> FEATURE:
<223> OTHER INFORMATION: peptide

<400> SEQUENCE: 206

Ser Val Arg Lys Ala

```
1               5

<210> SEQ ID NO 207
<211> LENGTH: 5
<212> TYPE: PRT
<213> ORGANISM: Artificial Sequence
<220> FEATURE:
<223> OTHER INFORMATION: peptide

<400> SEQUENCE: 207

Ser Val Arg Lys Thr
1               5

<210> SEQ ID NO 208
<211> LENGTH: 5
<212> TYPE: PRT
<213> ORGANISM: Artificial Sequence
<220> FEATURE:
<223> OTHER INFORMATION: peptide

<400> SEQUENCE: 208

Ser Val Arg Lys Pro
1               5

<210> SEQ ID NO 209
<211> LENGTH: 5
<212> TYPE: PRT
<213> ORGANISM: Artificial Sequence
<220> FEATURE:
<223> OTHER INFORMATION: peptide

<400> SEQUENCE: 209

Ser Pro Arg Arg Gln
1               5

<210> SEQ ID NO 210
<211> LENGTH: 5
<212> TYPE: PRT
<213> ORGANISM: Artificial Sequence
<220> FEATURE:
<223> OTHER INFORMATION: peptide

<400> SEQUENCE: 210

Ser Pro Arg Arg Phe
1               5

<210> SEQ ID NO 211
<211> LENGTH: 5
<212> TYPE: PRT
<213> ORGANISM: Artificial Sequence
<220> FEATURE:
<223> OTHER INFORMATION: peptide

<400> SEQUENCE: 211

Ser Pro Arg Arg His
1               5

<210> SEQ ID NO 212
<211> LENGTH: 5
<212> TYPE: PRT
<213> ORGANISM: Artificial Sequence
<220> FEATURE:
<223> OTHER INFORMATION: peptide

<400> SEQUENCE: 212

Ser Pro Arg Arg Arg
1               5
```

<210> SEQ ID NO 213
<211> LENGTH: 5
<212> TYPE: PRT
<213> ORGANISM: Artificial Sequence
<220> FEATURE:
<223> OTHER INFORMATION: peptide

<400> SEQUENCE: 213

Ser Pro Arg Arg Lys
1               5

<210> SEQ ID NO 214
<211> LENGTH: 5
<212> TYPE: PRT
<213> ORGANISM: Artificial Sequence
<220> FEATURE:
<223> OTHER INFORMATION: peptide

<400> SEQUENCE: 214

Ser Pro Arg Arg Cys
1               5

<210> SEQ ID NO 215
<211> LENGTH: 5
<212> TYPE: PRT
<213> ORGANISM: Artificial Sequence
<220> FEATURE:
<223> OTHER INFORMATION: peptide

<400> SEQUENCE: 215

Ser Pro Arg Arg Leu
1               5

<210> SEQ ID NO 216
<211> LENGTH: 5
<212> TYPE: PRT
<213> ORGANISM: Artificial Sequence
<220> FEATURE:
<223> OTHER INFORMATION: peptide

<400> SEQUENCE: 216

Ser Pro Arg Arg Tyr
1               5

<210> SEQ ID NO 217
<211> LENGTH: 5
<212> TYPE: PRT
<213> ORGANISM: Artificial Sequence
<220> FEATURE:
<223> OTHER INFORMATION: peptide

<400> SEQUENCE: 217

Ser Pro Arg Arg Asn
1               5

<210> SEQ ID NO 218
<211> LENGTH: 5
<212> TYPE: PRT
<213> ORGANISM: Artificial Sequence
<220> FEATURE:
<223> OTHER INFORMATION: peptide

<400> SEQUENCE: 218

Ser Pro Arg Arg Ile
1               5

```
<210> SEQ ID NO 219
<211> LENGTH: 5
<212> TYPE: PRT
<213> ORGANISM: Artificial Sequence
<220> FEATURE:
<223> OTHER INFORMATION: peptide

<400> SEQUENCE: 219

Ser Pro Arg Arg Asp
1               5

<210> SEQ ID NO 220
<211> LENGTH: 5
<212> TYPE: PRT
<213> ORGANISM: Artificial Sequence
<220> FEATURE:
<223> OTHER INFORMATION: peptide

<400> SEQUENCE: 220

Ser Pro Arg Arg Trp
1               5

<210> SEQ ID NO 221
<211> LENGTH: 5
<212> TYPE: PRT
<213> ORGANISM: Artificial Sequence
<220> FEATURE:
<223> OTHER INFORMATION: peptide

<400> SEQUENCE: 221

Ser Pro Arg Arg Glu
1               5

<210> SEQ ID NO 222
<211> LENGTH: 5
<212> TYPE: PRT
<213> ORGANISM: Artificial Sequence
<220> FEATURE:
<223> OTHER INFORMATION: peptide

<400> SEQUENCE: 222

Ser Pro Arg Arg Val
1               5

<210> SEQ ID NO 223
<211> LENGTH: 5
<212> TYPE: PRT
<213> ORGANISM: Artificial Sequence
<220> FEATURE:
<223> OTHER INFORMATION: peptide

<400> SEQUENCE: 223

Ser Pro Arg Arg Met
1               5

<210> SEQ ID NO 224
<211> LENGTH: 5
<212> TYPE: PRT
<213> ORGANISM: Artificial Sequence
<220> FEATURE:
<223> OTHER INFORMATION: peptide

<400> SEQUENCE: 224

Ser Pro Arg Arg Ala
1               5
```

```
<210> SEQ ID NO 225
<211> LENGTH: 5
<212> TYPE: PRT
<213> ORGANISM: Artificial Sequence
<220> FEATURE:
<223> OTHER INFORMATION: peptide

<400> SEQUENCE: 225

Ser Pro Arg Arg Thr
1               5

<210> SEQ ID NO 226
<211> LENGTH: 5
<212> TYPE: PRT
<213> ORGANISM: Artificial Sequence
<220> FEATURE:
<223> OTHER INFORMATION: peptide

<400> SEQUENCE: 226

Ser Pro Arg Arg Pro
1               5

<210> SEQ ID NO 227
<211> LENGTH: 5
<212> TYPE: PRT
<213> ORGANISM: Artificial Sequence
<220> FEATURE:
<223> OTHER INFORMATION: peptide

<400> SEQUENCE: 227

Ser Met Asp Arg Gln
1               5

<210> SEQ ID NO 228
<211> LENGTH: 5
<212> TYPE: PRT
<213> ORGANISM: Artificial Sequence
<220> FEATURE:
<223> OTHER INFORMATION: peptide

<400> SEQUENCE: 228

Ser Met Asp Arg Phe
1               5

<210> SEQ ID NO 229
<211> LENGTH: 5
<212> TYPE: PRT
<213> ORGANISM: Artificial Sequence
<220> FEATURE:
<223> OTHER INFORMATION: peptide

<400> SEQUENCE: 229

Ser Met Asp Arg His
1               5

<210> SEQ ID NO 230
<211> LENGTH: 5
<212> TYPE: PRT
<213> ORGANISM: Artificial Sequence
<220> FEATURE:
<223> OTHER INFORMATION: peptide

<400> SEQUENCE: 230

Ser Met Asp Arg Arg
1               5

<210> SEQ ID NO 231
```

```
<211> LENGTH: 5
<212> TYPE: PRT
<213> ORGANISM: Artificial Sequence
<220> FEATURE:
<223> OTHER INFORMATION: peptide

<400> SEQUENCE: 231

Ser Met Asp Arg Lys
1               5

<210> SEQ ID NO 232
<211> LENGTH: 5
<212> TYPE: PRT
<213> ORGANISM: Artificial Sequence
<220> FEATURE:
<223> OTHER INFORMATION: peptide

<400> SEQUENCE: 232

Ser Met Asp Arg Cys
1               5

<210> SEQ ID NO 233
<211> LENGTH: 5
<212> TYPE: PRT
<213> ORGANISM: Artificial Sequence
<220> FEATURE:
<223> OTHER INFORMATION: peptide

<400> SEQUENCE: 233

Ser Met Asp Arg Leu
1               5

<210> SEQ ID NO 234
<211> LENGTH: 5
<212> TYPE: PRT
<213> ORGANISM: Artificial Sequence
<220> FEATURE:
<223> OTHER INFORMATION: peptide

<400> SEQUENCE: 234

Ser Met Asp Arg Tyr
1               5

<210> SEQ ID NO 235
<211> LENGTH: 5
<212> TYPE: PRT
<213> ORGANISM: Artificial Sequence
<220> FEATURE:
<223> OTHER INFORMATION: peptide

<400> SEQUENCE: 235

Ser Met Asp Arg Asn
1               5

<210> SEQ ID NO 236
<211> LENGTH: 5
<212> TYPE: PRT
<213> ORGANISM: Artificial Sequence
<220> FEATURE:
<223> OTHER INFORMATION: peptide

<400> SEQUENCE: 236

Ser Met Asp Arg Ile
1               5

<210> SEQ ID NO 237
<211> LENGTH: 5
```

```
<212> TYPE: PRT
<213> ORGANISM: Artificial Sequence
<220> FEATURE:
<223> OTHER INFORMATION: peptide

<400> SEQUENCE: 237

Ser Met Asp Arg Asp
1               5

<210> SEQ ID NO 238
<211> LENGTH: 5
<212> TYPE: PRT
<213> ORGANISM: Artificial Sequence
<220> FEATURE:
<223> OTHER INFORMATION: peptide

<400> SEQUENCE: 238

Ser Met Asp Arg Trp
1               5

<210> SEQ ID NO 239
<211> LENGTH: 5
<212> TYPE: PRT
<213> ORGANISM: Artificial Sequence
<220> FEATURE:
<223> OTHER INFORMATION: peptide

<400> SEQUENCE: 239

Ser Met Asp Arg Glu
1               5

<210> SEQ ID NO 240
<211> LENGTH: 5
<212> TYPE: PRT
<213> ORGANISM: Artificial Sequence
<220> FEATURE:
<223> OTHER INFORMATION: peptide

<400> SEQUENCE: 240

Ser Met Asp Arg Val
1               5

<210> SEQ ID NO 241
<211> LENGTH: 5
<212> TYPE: PRT
<213> ORGANISM: Artificial Sequence
<220> FEATURE:
<223> OTHER INFORMATION: peptide

<400> SEQUENCE: 241

Ser Met Asp Arg Met
1               5

<210> SEQ ID NO 242
<211> LENGTH: 5
<212> TYPE: PRT
<213> ORGANISM: Artificial Sequence
<220> FEATURE:
<223> OTHER INFORMATION: peptide

<400> SEQUENCE: 242

Ser Met Asp Arg Ala
1               5

<210> SEQ ID NO 243
<211> LENGTH: 5
<212> TYPE: PRT
```

```
<213> ORGANISM: Artificial Sequence
<220> FEATURE:
<223> OTHER INFORMATION: peptide

<400> SEQUENCE: 243

Ser Met Asp Arg Thr
1               5

<210> SEQ ID NO 244
<211> LENGTH: 5
<212> TYPE: PRT
<213> ORGANISM: Artificial Sequence
<220> FEATURE:
<223> OTHER INFORMATION: peptide

<400> SEQUENCE: 244

Ser Met Asp Arg Pro
1               5

<210> SEQ ID NO 245
<211> LENGTH: 5
<212> TYPE: PRT
<213> ORGANISM: Artificial Sequence
<220> FEATURE:
<223> OTHER INFORMATION: peptide

<400> SEQUENCE: 245

Ser Leu Gly Arg Gln
1               5

<210> SEQ ID NO 246
<211> LENGTH: 5
<212> TYPE: PRT
<213> ORGANISM: Artificial Sequence
<220> FEATURE:
<223> OTHER INFORMATION: peptide

<400> SEQUENCE: 246

Ser Leu Gly Arg Phe
1               5

<210> SEQ ID NO 247
<211> LENGTH: 5
<212> TYPE: PRT
<213> ORGANISM: Artificial Sequence
<220> FEATURE:
<223> OTHER INFORMATION: peptide

<400> SEQUENCE: 247

Ser Leu Gly Arg His
1               5

<210> SEQ ID NO 248
<211> LENGTH: 5
<212> TYPE: PRT
<213> ORGANISM: Artificial Sequence
<220> FEATURE:
<223> OTHER INFORMATION: peptide

<400> SEQUENCE: 248

Ser Leu Gly Arg Arg
1               5

<210> SEQ ID NO 249
<211> LENGTH: 5
<212> TYPE: PRT
<213> ORGANISM: Artificial Sequence
```

```
<220> FEATURE:
<223> OTHER INFORMATION: peptide

<400> SEQUENCE: 249

Ser Leu Gly Arg Lys
1               5

<210> SEQ ID NO 250
<211> LENGTH: 5
<212> TYPE: PRT
<213> ORGANISM: Artificial Sequence
<220> FEATURE:
<223> OTHER INFORMATION: peptide

<400> SEQUENCE: 250

Ser Leu Gly Arg Cys
1               5

<210> SEQ ID NO 251
<211> LENGTH: 5
<212> TYPE: PRT
<213> ORGANISM: Artificial Sequence
<220> FEATURE:
<223> OTHER INFORMATION: peptide

<400> SEQUENCE: 251

Ser Leu Gly Arg Leu
1               5

<210> SEQ ID NO 252
<211> LENGTH: 5
<212> TYPE: PRT
<213> ORGANISM: Artificial Sequence
<220> FEATURE:
<223> OTHER INFORMATION: peptide

<400> SEQUENCE: 252

Ser Leu Gly Arg Tyr
1               5

<210> SEQ ID NO 253
<211> LENGTH: 5
<212> TYPE: PRT
<213> ORGANISM: Artificial Sequence
<220> FEATURE:
<223> OTHER INFORMATION: peptide

<400> SEQUENCE: 253

Ser Leu Gly Arg Asn
1               5

<210> SEQ ID NO 254
<211> LENGTH: 5
<212> TYPE: PRT
<213> ORGANISM: Artificial Sequence
<220> FEATURE:
<223> OTHER INFORMATION: peptide

<400> SEQUENCE: 254

Ser Leu Gly Arg Ile
1               5

<210> SEQ ID NO 255
<211> LENGTH: 5
<212> TYPE: PRT
<213> ORGANISM: Artificial Sequence
<220> FEATURE:
```

<223> OTHER INFORMATION: peptide

<400> SEQUENCE: 255

Ser Leu Gly Arg Asp
1               5

<210> SEQ ID NO 256
<211> LENGTH: 5
<212> TYPE: PRT
<213> ORGANISM: Artificial Sequence
<220> FEATURE:
<223> OTHER INFORMATION: peptide

<400> SEQUENCE: 256

Ser Leu Gly Arg Trp
1               5

<210> SEQ ID NO 257
<211> LENGTH: 5
<212> TYPE: PRT
<213> ORGANISM: Artificial Sequence
<220> FEATURE:
<223> OTHER INFORMATION: peptide

<400> SEQUENCE: 257

Ser Leu Gly Arg Glu
1               5

<210> SEQ ID NO 258
<211> LENGTH: 5
<212> TYPE: PRT
<213> ORGANISM: Artificial Sequence
<220> FEATURE:
<223> OTHER INFORMATION: peptide

<400> SEQUENCE: 258

Ser Leu Gly Arg Val
1               5

<210> SEQ ID NO 259
<211> LENGTH: 5
<212> TYPE: PRT
<213> ORGANISM: Artificial Sequence
<220> FEATURE:
<223> OTHER INFORMATION: peptide

<400> SEQUENCE: 259

Ser Leu Gly Arg Met
1               5

<210> SEQ ID NO 260
<211> LENGTH: 5
<212> TYPE: PRT
<213> ORGANISM: Artificial Sequence
<220> FEATURE:
<223> OTHER INFORMATION: peptide

<400> SEQUENCE: 260

Ser Leu Gly Arg Ala
1               5

<210> SEQ ID NO 261
<211> LENGTH: 5
<212> TYPE: PRT
<213> ORGANISM: Artificial Sequence
<220> FEATURE:
<223> OTHER INFORMATION: peptide

```
<400> SEQUENCE: 261

Ser Leu Gly Arg Thr
1               5

<210> SEQ ID NO 262
<211> LENGTH: 5
<212> TYPE: PRT
<213> ORGANISM: Artificial Sequence
<220> FEATURE:
<223> OTHER INFORMATION: peptide

<400> SEQUENCE: 262

Ser Leu Gly Arg Pro
1               5

<210> SEQ ID NO 263
<211> LENGTH: 5
<212> TYPE: PRT
<213> ORGANISM: Artificial Sequence
<220> FEATURE:
<223> OTHER INFORMATION: peptide

<400> SEQUENCE: 263

Ser Lys Gly Arg Gln
1               5

<210> SEQ ID NO 264
<211> LENGTH: 5
<212> TYPE: PRT
<213> ORGANISM: Artificial Sequence
<220> FEATURE:
<223> OTHER INFORMATION: peptide

<400> SEQUENCE: 264

Ser Lys Gly Arg Phe
1               5

<210> SEQ ID NO 265
<211> LENGTH: 5
<212> TYPE: PRT
<213> ORGANISM: Artificial Sequence
<220> FEATURE:
<223> OTHER INFORMATION: peptide

<400> SEQUENCE: 265

Ser Lys Gly Arg His
1               5

<210> SEQ ID NO 266
<211> LENGTH: 5
<212> TYPE: PRT
<213> ORGANISM: Artificial Sequence
<220> FEATURE:
<223> OTHER INFORMATION: peptide

<400> SEQUENCE: 266

Ser Lys Gly Arg Arg
1               5

<210> SEQ ID NO 267
<211> LENGTH: 5
<212> TYPE: PRT
<213> ORGANISM: Artificial Sequence
<220> FEATURE:
<223> OTHER INFORMATION: peptide
```

```
<400> SEQUENCE: 267

Ser Lys Gly Arg Lys
1               5

<210> SEQ ID NO 268
<211> LENGTH: 5
<212> TYPE: PRT
<213> ORGANISM: Artificial Sequence
<220> FEATURE:
<223> OTHER INFORMATION: peptide

<400> SEQUENCE: 268

Ser Lys Gly Arg Cys
1               5

<210> SEQ ID NO 269
<211> LENGTH: 5
<212> TYPE: PRT
<213> ORGANISM: Artificial Sequence
<220> FEATURE:
<223> OTHER INFORMATION: peptide

<400> SEQUENCE: 269

Ser Lys Gly Arg Leu
1               5

<210> SEQ ID NO 270
<211> LENGTH: 5
<212> TYPE: PRT
<213> ORGANISM: Artificial Sequence
<220> FEATURE:
<223> OTHER INFORMATION: peptide

<400> SEQUENCE: 270

Ser Lys Gly Arg Tyr
1               5

<210> SEQ ID NO 271
<211> LENGTH: 5
<212> TYPE: PRT
<213> ORGANISM: Artificial Sequence
<220> FEATURE:
<223> OTHER INFORMATION: peptide

<400> SEQUENCE: 271

Ser Lys Gly Arg Asn
1               5

<210> SEQ ID NO 272
<211> LENGTH: 5
<212> TYPE: PRT
<213> ORGANISM: Artificial Sequence
<220> FEATURE:
<223> OTHER INFORMATION: peptide

<400> SEQUENCE: 272

Ser Lys Gly Arg Ile
1               5

<210> SEQ ID NO 273
<211> LENGTH: 5
<212> TYPE: PRT
<213> ORGANISM: Artificial Sequence
<220> FEATURE:
<223> OTHER INFORMATION: peptide

<400> SEQUENCE: 273
```

```
Ser Lys Gly Arg Asp
1               5

<210> SEQ ID NO 274
<211> LENGTH: 5
<212> TYPE: PRT
<213> ORGANISM: Artificial Sequence
<220> FEATURE:
<223> OTHER INFORMATION: peptide

<400> SEQUENCE: 274

Ser Lys Gly Arg Trp
1               5

<210> SEQ ID NO 275
<211> LENGTH: 5
<212> TYPE: PRT
<213> ORGANISM: Artificial Sequence
<220> FEATURE:
<223> OTHER INFORMATION: peptide

<400> SEQUENCE: 275

Ser Lys Gly Arg Glu
1               5

<210> SEQ ID NO 276
<211> LENGTH: 5
<212> TYPE: PRT
<213> ORGANISM: Artificial Sequence
<220> FEATURE:
<223> OTHER INFORMATION: peptide

<400> SEQUENCE: 276

Ser Lys Gly Arg Val
1               5

<210> SEQ ID NO 277
<211> LENGTH: 5
<212> TYPE: PRT
<213> ORGANISM: Artificial Sequence
<220> FEATURE:
<223> OTHER INFORMATION: peptide

<400> SEQUENCE: 277

Ser Lys Gly Arg Met
1               5

<210> SEQ ID NO 278
<211> LENGTH: 5
<212> TYPE: PRT
<213> ORGANISM: Artificial Sequence
<220> FEATURE:
<223> OTHER INFORMATION: peptide

<400> SEQUENCE: 278

Ser Lys Gly Arg Ala
1               5

<210> SEQ ID NO 279
<211> LENGTH: 5
<212> TYPE: PRT
<213> ORGANISM: Artificial Sequence
<220> FEATURE:
<223> OTHER INFORMATION: peptide

<400> SEQUENCE: 279
```

```
Ser Lys Gly Arg Thr
1               5

<210> SEQ ID NO 280
<211> LENGTH: 5
<212> TYPE: PRT
<213> ORGANISM: Artificial Sequence
<220> FEATURE:
<223> OTHER INFORMATION: peptide

<400> SEQUENCE: 280

Ser Lys Gly Arg Pro
1               5

<210> SEQ ID NO 281
<211> LENGTH: 5
<212> TYPE: PRT
<213> ORGANISM: Artificial Sequence
<220> FEATURE:
<223> OTHER INFORMATION: peptide

<400> SEQUENCE: 281

Ser Gly Asn Arg Gln
1               5

<210> SEQ ID NO 282
<211> LENGTH: 5
<212> TYPE: PRT
<213> ORGANISM: Artificial Sequence
<220> FEATURE:
<223> OTHER INFORMATION: peptide

<400> SEQUENCE: 282

Ser Gly Asn Arg Phe
1               5

<210> SEQ ID NO 283
<211> LENGTH: 5
<212> TYPE: PRT
<213> ORGANISM: Artificial Sequence
<220> FEATURE:
<223> OTHER INFORMATION: peptide

<400> SEQUENCE: 283

Ser Gly Asn Arg His
1               5

<210> SEQ ID NO 284
<211> LENGTH: 5
<212> TYPE: PRT
<213> ORGANISM: Artificial Sequence
<220> FEATURE:
<223> OTHER INFORMATION: peptide

<400> SEQUENCE: 284

Ser Gly Asn Arg Arg
1               5

<210> SEQ ID NO 285
<211> LENGTH: 5
<212> TYPE: PRT
<213> ORGANISM: Artificial Sequence
<220> FEATURE:
<223> OTHER INFORMATION: peptide

<400> SEQUENCE: 285

Ser Gly Asn Arg Lys
```

```
1               5

<210> SEQ ID NO 286
<211> LENGTH: 5
<212> TYPE: PRT
<213> ORGANISM: Artificial Sequence
<220> FEATURE:
<223> OTHER INFORMATION: peptide

<400> SEQUENCE: 286

Ser Gly Asn Arg Cys
1               5

<210> SEQ ID NO 287
<211> LENGTH: 5
<212> TYPE: PRT
<213> ORGANISM: Artificial Sequence
<220> FEATURE:
<223> OTHER INFORMATION: peptide

<400> SEQUENCE: 287

Ser Gly Asn Arg Leu
1               5

<210> SEQ ID NO 288
<211> LENGTH: 5
<212> TYPE: PRT
<213> ORGANISM: Artificial Sequence
<220> FEATURE:
<223> OTHER INFORMATION: peptide

<400> SEQUENCE: 288

Ser Gly Asn Arg Tyr
1               5

<210> SEQ ID NO 289
<211> LENGTH: 5
<212> TYPE: PRT
<213> ORGANISM: Artificial Sequence
<220> FEATURE:
<223> OTHER INFORMATION: peptide

<400> SEQUENCE: 289

Ser Gly Asn Arg Asn
1               5

<210> SEQ ID NO 290
<211> LENGTH: 5
<212> TYPE: PRT
<213> ORGANISM: Artificial Sequence
<220> FEATURE:
<223> OTHER INFORMATION: peptide

<400> SEQUENCE: 290

Ser Gly Asn Arg Ile
1               5

<210> SEQ ID NO 291
<211> LENGTH: 5
<212> TYPE: PRT
<213> ORGANISM: Artificial Sequence
<220> FEATURE:
<223> OTHER INFORMATION: peptide

<400> SEQUENCE: 291

Ser Gly Asn Arg Asp
1               5
```

```
<210> SEQ ID NO 292
<211> LENGTH: 5
<212> TYPE: PRT
<213> ORGANISM: Artificial Sequence
<220> FEATURE:
<223> OTHER INFORMATION: peptide

<400> SEQUENCE: 292

Ser Gly Asn Arg Trp
1               5

<210> SEQ ID NO 293
<211> LENGTH: 5
<212> TYPE: PRT
<213> ORGANISM: Artificial Sequence
<220> FEATURE:
<223> OTHER INFORMATION: peptide

<400> SEQUENCE: 293

Ser Gly Asn Arg Glu
1               5

<210> SEQ ID NO 294
<211> LENGTH: 5
<212> TYPE: PRT
<213> ORGANISM: Artificial Sequence
<220> FEATURE:
<223> OTHER INFORMATION: peptide

<400> SEQUENCE: 294

Ser Gly Asn Arg Val
1               5

<210> SEQ ID NO 295
<211> LENGTH: 5
<212> TYPE: PRT
<213> ORGANISM: Artificial Sequence
<220> FEATURE:
<223> OTHER INFORMATION: peptide

<400> SEQUENCE: 295

Ser Gly Asn Arg Met
1               5

<210> SEQ ID NO 296
<211> LENGTH: 5
<212> TYPE: PRT
<213> ORGANISM: Artificial Sequence
<220> FEATURE:
<223> OTHER INFORMATION: peptide

<400> SEQUENCE: 296

Ser Gly Asn Arg Ala
1               5

<210> SEQ ID NO 297
<211> LENGTH: 5
<212> TYPE: PRT
<213> ORGANISM: Artificial Sequence
<220> FEATURE:
<223> OTHER INFORMATION: peptide

<400> SEQUENCE: 297

Ser Gly Asn Arg Thr
1               5
```

```
<210> SEQ ID NO 298
<211> LENGTH: 5
<212> TYPE: PRT
<213> ORGANISM: Artificial Sequence
<220> FEATURE:
<223> OTHER INFORMATION: peptide

<400> SEQUENCE: 298

Ser Gly Asn Arg Pro
1               5

<210> SEQ ID NO 299
<211> LENGTH: 5
<212> TYPE: PRT
<213> ORGANISM: Artificial Sequence
<220> FEATURE:
<223> OTHER INFORMATION: peptide

<400> SEQUENCE: 299

Ser Met His Arg Gln
1               5

<210> SEQ ID NO 300
<211> LENGTH: 5
<212> TYPE: PRT
<213> ORGANISM: Artificial Sequence
<220> FEATURE:
<223> OTHER INFORMATION: peptide

<400> SEQUENCE: 300

Ser Met His Arg Phe
1               5

<210> SEQ ID NO 301
<211> LENGTH: 5
<212> TYPE: PRT
<213> ORGANISM: Artificial Sequence
<220> FEATURE:
<223> OTHER INFORMATION: peptide

<400> SEQUENCE: 301

Ser Met His Arg His
1               5

<210> SEQ ID NO 302
<211> LENGTH: 5
<212> TYPE: PRT
<213> ORGANISM: Artificial Sequence
<220> FEATURE:
<223> OTHER INFORMATION: peptide

<400> SEQUENCE: 302

Ser Met His Arg Arg
1               5

<210> SEQ ID NO 303
<211> LENGTH: 5
<212> TYPE: PRT
<213> ORGANISM: Artificial Sequence
<220> FEATURE:
<223> OTHER INFORMATION: peptide

<400> SEQUENCE: 303

Ser Met His Arg Lys
1               5
```

```
<210> SEQ ID NO 304
<211> LENGTH: 5
<212> TYPE: PRT
<213> ORGANISM: Artificial Sequence
<220> FEATURE:
<223> OTHER INFORMATION: peptide

<400> SEQUENCE: 304

Ser Met His Arg Cys
1               5

<210> SEQ ID NO 305
<211> LENGTH: 5
<212> TYPE: PRT
<213> ORGANISM: Artificial Sequence
<220> FEATURE:
<223> OTHER INFORMATION: peptide

<400> SEQUENCE: 305

Ser Met His Arg Leu
1               5

<210> SEQ ID NO 306
<211> LENGTH: 5
<212> TYPE: PRT
<213> ORGANISM: Artificial Sequence
<220> FEATURE:
<223> OTHER INFORMATION: peptide

<400> SEQUENCE: 306

Ser Met His Arg Tyr
1               5

<210> SEQ ID NO 307
<211> LENGTH: 5
<212> TYPE: PRT
<213> ORGANISM: Artificial Sequence
<220> FEATURE:
<223> OTHER INFORMATION: peptide

<400> SEQUENCE: 307

Ser Met His Arg Asn
1               5

<210> SEQ ID NO 308
<211> LENGTH: 5
<212> TYPE: PRT
<213> ORGANISM: Artificial Sequence
<220> FEATURE:
<223> OTHER INFORMATION: peptide

<400> SEQUENCE: 308

Ser Met His Arg Ile
1               5

<210> SEQ ID NO 309
<211> LENGTH: 5
<212> TYPE: PRT
<213> ORGANISM: Artificial Sequence
<220> FEATURE:
<223> OTHER INFORMATION: peptide

<400> SEQUENCE: 309

Ser Met His Arg Asp
1               5

<210> SEQ ID NO 310
```

```
<211> LENGTH: 5
<212> TYPE: PRT
<213> ORGANISM: Artificial Sequence
<220> FEATURE:
<223> OTHER INFORMATION: peptide

<400> SEQUENCE: 310

Ser Met His Arg Trp
1               5

<210> SEQ ID NO 311
<211> LENGTH: 5
<212> TYPE: PRT
<213> ORGANISM: Artificial Sequence
<220> FEATURE:
<223> OTHER INFORMATION: peptide

<400> SEQUENCE: 311

Ser Met His Arg Glu
1               5

<210> SEQ ID NO 312
<211> LENGTH: 5
<212> TYPE: PRT
<213> ORGANISM: Artificial Sequence
<220> FEATURE:
<223> OTHER INFORMATION: peptide

<400> SEQUENCE: 312

Ser Met His Arg Val
1               5

<210> SEQ ID NO 313
<211> LENGTH: 5
<212> TYPE: PRT
<213> ORGANISM: Artificial Sequence
<220> FEATURE:
<223> OTHER INFORMATION: peptide

<400> SEQUENCE: 313

Ser Met His Arg Met
1               5

<210> SEQ ID NO 314
<211> LENGTH: 5
<212> TYPE: PRT
<213> ORGANISM: Artificial Sequence
<220> FEATURE:
<223> OTHER INFORMATION: peptide

<400> SEQUENCE: 314

Ser Met His Arg Ala
1               5

<210> SEQ ID NO 315
<211> LENGTH: 5
<212> TYPE: PRT
<213> ORGANISM: Artificial Sequence
<220> FEATURE:
<223> OTHER INFORMATION: peptide

<400> SEQUENCE: 315

Ser Met His Arg Thr
1               5

<210> SEQ ID NO 316
<211> LENGTH: 5
```

```
<212> TYPE: PRT
<213> ORGANISM: Artificial Sequence
<220> FEATURE:
<223> OTHER INFORMATION: peptide

<400> SEQUENCE: 316

Ser Met His Arg Pro
1               5

<210> SEQ ID NO 317
<211> LENGTH: 5
<212> TYPE: PRT
<213> ORGANISM: Artificial Sequence
<220> FEATURE:
<223> OTHER INFORMATION: peptide

<400> SEQUENCE: 317

Ser Leu Leu Arg Gln
1               5

<210> SEQ ID NO 318
<211> LENGTH: 5
<212> TYPE: PRT
<213> ORGANISM: Artificial Sequence
<220> FEATURE:
<223> OTHER INFORMATION: peptide

<400> SEQUENCE: 318

Ser Leu Leu Arg Phe
1               5

<210> SEQ ID NO 319
<211> LENGTH: 5
<212> TYPE: PRT
<213> ORGANISM: Artificial Sequence
<220> FEATURE:
<223> OTHER INFORMATION: peptide

<400> SEQUENCE: 319

Ser Leu Leu Arg His
1               5

<210> SEQ ID NO 320
<211> LENGTH: 5
<212> TYPE: PRT
<213> ORGANISM: Artificial Sequence
<220> FEATURE:
<223> OTHER INFORMATION: peptide

<400> SEQUENCE: 320

Ser Leu Leu Arg Arg
1               5

<210> SEQ ID NO 321
<211> LENGTH: 5
<212> TYPE: PRT
<213> ORGANISM: Artificial Sequence
<220> FEATURE:
<223> OTHER INFORMATION: peptide

<400> SEQUENCE: 321

Ser Leu Leu Arg Lys
1               5

<210> SEQ ID NO 322
<211> LENGTH: 5
<212> TYPE: PRT
```

```
<213> ORGANISM: Artificial Sequence
<220> FEATURE:
<223> OTHER INFORMATION: peptide

<400> SEQUENCE: 322

Ser Leu Leu Arg Cys
1               5

<210> SEQ ID NO 323
<211> LENGTH: 5
<212> TYPE: PRT
<213> ORGANISM: Artificial Sequence
<220> FEATURE:
<223> OTHER INFORMATION: peptide

<400> SEQUENCE: 323

Ser Leu Leu Arg Leu
1               5

<210> SEQ ID NO 324
<211> LENGTH: 5
<212> TYPE: PRT
<213> ORGANISM: Artificial Sequence
<220> FEATURE:
<223> OTHER INFORMATION: peptide

<400> SEQUENCE: 324

Ser Leu Leu Arg Tyr
1               5

<210> SEQ ID NO 325
<211> LENGTH: 5
<212> TYPE: PRT
<213> ORGANISM: Artificial Sequence
<220> FEATURE:
<223> OTHER INFORMATION: peptide

<400> SEQUENCE: 325

Ser Leu Leu Arg Asn
1               5

<210> SEQ ID NO 326
<211> LENGTH: 5
<212> TYPE: PRT
<213> ORGANISM: Artificial Sequence
<220> FEATURE:
<223> OTHER INFORMATION: peptide

<400> SEQUENCE: 326

Ser Leu Leu Arg Ile
1               5

<210> SEQ ID NO 327
<211> LENGTH: 5
<212> TYPE: PRT
<213> ORGANISM: Artificial Sequence
<220> FEATURE:
<223> OTHER INFORMATION: peptide

<400> SEQUENCE: 327

Ser Leu Leu Arg Asp
1               5

<210> SEQ ID NO 328
<211> LENGTH: 5
<212> TYPE: PRT
<213> ORGANISM: Artificial Sequence
```

```
<220> FEATURE:
<223> OTHER INFORMATION: peptide

<400> SEQUENCE: 328

Ser Leu Leu Arg Trp
1               5

<210> SEQ ID NO 329
<211> LENGTH: 5
<212> TYPE: PRT
<213> ORGANISM: Artificial Sequence
<220> FEATURE:
<223> OTHER INFORMATION: peptide

<400> SEQUENCE: 329

Ser Leu Leu Arg Glu
1               5

<210> SEQ ID NO 330
<211> LENGTH: 5
<212> TYPE: PRT
<213> ORGANISM: Artificial Sequence
<220> FEATURE:
<223> OTHER INFORMATION: peptide

<400> SEQUENCE: 330

Ser Leu Leu Arg Val
1               5

<210> SEQ ID NO 331
<211> LENGTH: 5
<212> TYPE: PRT
<213> ORGANISM: Artificial Sequence
<220> FEATURE:
<223> OTHER INFORMATION: peptide

<400> SEQUENCE: 331

Ser Leu Leu Arg Met
1               5

<210> SEQ ID NO 332
<211> LENGTH: 5
<212> TYPE: PRT
<213> ORGANISM: Artificial Sequence
<220> FEATURE:
<223> OTHER INFORMATION: peptide

<400> SEQUENCE: 332

Ser Leu Leu Arg Ala
1               5

<210> SEQ ID NO 333
<211> LENGTH: 5
<212> TYPE: PRT
<213> ORGANISM: Artificial Sequence
<220> FEATURE:
<223> OTHER INFORMATION: peptide

<400> SEQUENCE: 333

Ser Leu Leu Arg Thr
1               5

<210> SEQ ID NO 334
<211> LENGTH: 5
<212> TYPE: PRT
<213> ORGANISM: Artificial Sequence
<220> FEATURE:
```

<223> OTHER INFORMATION: peptide

<400> SEQUENCE: 334

Ser Leu Leu Arg Pro
1               5

<210> SEQ ID NO 335
<211> LENGTH: 8
<212> TYPE: PRT
<213> ORGANISM: Artificial Sequence
<220> FEATURE:
<223> OTHER INFORMATION: peptide

<400> SEQUENCE: 335

Ala Ile Pro Met Ser Ile Pro Pro
1               5

<210> SEQ ID NO 336
<211> LENGTH: 8
<212> TYPE: PRT
<213> ORGANISM: Artificial Sequence
<220> FEATURE:
<223> OTHER INFORMATION: peptide

<400> SEQUENCE: 336

Ala Ile Pro Arg Ser Ile Pro Pro
1               5

<210> SEQ ID NO 337
<211> LENGTH: 8
<212> TYPE: PRT
<213> ORGANISM: Artificial Sequence
<220> FEATURE:
<223> OTHER INFORMATION: peptide

<400> SEQUENCE: 337

Ala Ile Ala Arg Ser Ile Pro Pro
1               5

<210> SEQ ID NO 338
<211> LENGTH: 8
<212> TYPE: PRT
<213> ORGANISM: Artificial Sequence
<220> FEATURE:
<223> OTHER INFORMATION: peptide

<400> SEQUENCE: 338

Ser Met Thr Arg Ser Ile Pro Pro
1               5

<210> SEQ ID NO 339
<211> LENGTH: 8
<212> TYPE: PRT
<213> ORGANISM: Artificial Sequence
<220> FEATURE:
<223> OTHER INFORMATION: peptide

<400> SEQUENCE: 339

Ser Met Thr Arg Ser Ile Pro Pro
1               5

<210> SEQ ID NO 340
<211> LENGTH: 8
<212> TYPE: PRT
<213> ORGANISM: Artificial Sequence
<220> FEATURE:
<223> OTHER INFORMATION: peptide

```
<400> SEQUENCE: 340

Ser Met Thr Arg Val Val Gly Gly
1               5

<210> SEQ ID NO 341
<211> LENGTH: 8
<212> TYPE: PRT
<213> ORGANISM: Artificial Sequence
<220> FEATURE:
<223> OTHER INFORMATION: peptide

<400> SEQUENCE: 341

Ser Met Thr Arg Gly Val Gly Gly
1               5

<210> SEQ ID NO 342
<211> LENGTH: 8
<212> TYPE: PRT
<213> ORGANISM: Artificial Sequence
<220> FEATURE:
<223> OTHER INFORMATION: peptide

<400> SEQUENCE: 342

Ser Gly Gln Arg Ser Ile Pro Pro
1               5

<210> SEQ ID NO 343
<211> LENGTH: 8
<212> TYPE: PRT
<213> ORGANISM: Artificial Sequence
<220> FEATURE:
<223> OTHER INFORMATION: peptide

<400> SEQUENCE: 343

Ser Val Thr Arg Ser Ile Pro Pro
1               5

<210> SEQ ID NO 344
<211> LENGTH: 8
<212> TYPE: PRT
<213> ORGANISM: Artificial Sequence
<220> FEATURE:
<223> OTHER INFORMATION: peptide

<400> SEQUENCE: 344

Ser Ala Thr Arg Ser Ile Pro Pro
1               5

<210> SEQ ID NO 345
<211> LENGTH: 8
<212> TYPE: PRT
<213> ORGANISM: Artificial Sequence
<220> FEATURE:
<223> OTHER INFORMATION: peptide

<400> SEQUENCE: 345

Ser Phe Asn Arg Ser Ile Pro Pro
1               5

<210> SEQ ID NO 346
<211> LENGTH: 8
<212> TYPE: PRT
<213> ORGANISM: Artificial Sequence
<220> FEATURE:
<223> OTHER INFORMATION: peptide
```

```
<400> SEQUENCE: 346

Ser Trp Lys Lys Ser Ile Pro Pro
1               5

<210> SEQ ID NO 347
<211> LENGTH: 8
<212> TYPE: PRT
<213> ORGANISM: Artificial Sequence
<220> FEATURE:
<223> OTHER INFORMATION: peptide

<400> SEQUENCE: 347

Ser Glu Ala Arg Ser Ile Pro Pro
1               5

<210> SEQ ID NO 348
<211> LENGTH: 8
<212> TYPE: PRT
<213> ORGANISM: Artificial Sequence
<220> FEATURE:
<223> OTHER INFORMATION: peptide

<400> SEQUENCE: 348

Ser Leu Leu Arg Ser Ile Pro Pro
1               5

<210> SEQ ID NO 349
<211> LENGTH: 8
<212> TYPE: PRT
<213> ORGANISM: Artificial Sequence
<220> FEATURE:
<223> OTHER INFORMATION: peptide

<400> SEQUENCE: 349

Ser Leu Leu Arg Val Ile Pro Pro
1               5

<210> SEQ ID NO 350
<211> LENGTH: 8
<212> TYPE: PRT
<213> ORGANISM: Artificial Sequence
<220> FEATURE:
<223> OTHER INFORMATION: peptide

<400> SEQUENCE: 350

Ser Leu Leu Arg Ile Ile Pro Pro
1               5

<210> SEQ ID NO 351
<211> LENGTH: 8
<212> TYPE: PRT
<213> ORGANISM: Artificial Sequence
<220> FEATURE:
<223> OTHER INFORMATION: peptide

<400> SEQUENCE: 351

Ser Val Val Lys Ser Ile Pro Pro
1               5

<210> SEQ ID NO 352
<211> LENGTH: 8
<212> TYPE: PRT
<213> ORGANISM: Artificial Sequence
<220> FEATURE:
<223> OTHER INFORMATION: peptide

<400> SEQUENCE: 352
```

```
Ser Asp Tyr Lys Ser Ile Pro Pro
1               5

<210> SEQ ID NO 353
<211> LENGTH: 8
<212> TYPE: PRT
<213> ORGANISM: Artificial Sequence
<220> FEATURE:
<223> OTHER INFORMATION: peptide

<400> SEQUENCE: 353

Ser Val Arg Lys Ser Ile Pro Pro
1               5

<210> SEQ ID NO 354
<211> LENGTH: 8
<212> TYPE: PRT
<213> ORGANISM: Artificial Sequence
<220> FEATURE:
<223> OTHER INFORMATION: peptide

<400> SEQUENCE: 354

Ser Pro Arg Arg Ser Ile Pro Pro
1               5

<210> SEQ ID NO 355
<211> LENGTH: 8
<212> TYPE: PRT
<213> ORGANISM: Artificial Sequence
<220> FEATURE:
<223> OTHER INFORMATION: peptide

<400> SEQUENCE: 355

Ser Met Asp Arg Ser Ile Pro Pro
1               5

<210> SEQ ID NO 356
<211> LENGTH: 8
<212> TYPE: PRT
<213> ORGANISM: Artificial Sequence
<220> FEATURE:
<223> OTHER INFORMATION: peptide

<400> SEQUENCE: 356

Ser Leu Gly Arg Ser Ile Pro Pro
1               5

<210> SEQ ID NO 357
<211> LENGTH: 8
<212> TYPE: PRT
<213> ORGANISM: Artificial Sequence
<220> FEATURE:
<223> OTHER INFORMATION: peptide

<400> SEQUENCE: 357

Ser Lys Gly Arg Ser Ile Pro Pro
1               5

<210> SEQ ID NO 358
<211> LENGTH: 8
<212> TYPE: PRT
<213> ORGANISM: Artificial Sequence
<220> FEATURE:
<223> OTHER INFORMATION: peptide

<400> SEQUENCE: 358
```

```
Ser Gly Trp Arg Ser Ile Pro Pro
1               5

<210> SEQ ID NO 359
<211> LENGTH: 8
<212> TYPE: PRT
<213> ORGANISM: Artificial Sequence
<220> FEATURE:
<223> OTHER INFORMATION: peptide

<400> SEQUENCE: 359

Ser Tyr Ala Arg Ser Ile Pro Pro
1               5

<210> SEQ ID NO 360
<211> LENGTH: 8
<212> TYPE: PRT
<213> ORGANISM: Artificial Sequence
<220> FEATURE:
<223> OTHER INFORMATION: peptide

<400> SEQUENCE: 360

Ser Met His Arg Ser Ile Pro Pro
1               5

<210> SEQ ID NO 361
<211> LENGTH: 8
<212> TYPE: PRT
<213> ORGANISM: Artificial Sequence
<220> FEATURE:
<223> OTHER INFORMATION: peptide

<400> SEQUENCE: 361

Ser Asn Ser Arg Ser Ile Pro Pro
1               5
```